(12) United States Patent
Vallino et al.

(10) Patent No.: US 12,213,904 B2
(45) Date of Patent: Feb. 4, 2025

(54) INTRAVENOUS EXTREMITY SUPPORT

(71) Applicant: I.V. House, Inc., Chesterfield, MO (US)

(72) Inventors: Lisa Vallino, St. Louis, MO (US);
Jennifer Marusich, Sanger, TX (US);
Betty Rozier, Chesterfield, MO (US)

(*) Notice: Subject to any disclaimer, the term of this patent is extended or adjusted under 35 U.S.C. 154(b) by 0 days.

(21) Appl. No.: 13/973,800

(22) Filed: Aug. 22, 2013

(65) Prior Publication Data
US 2014/0060547 A1 Mar. 6, 2014

Related U.S. Application Data

(60) Provisional application No. 61/692,120, filed on Aug. 22, 2012, provisional application No. 61/794,512, filed on Mar. 15, 2013.

(51) Int. Cl.
A61F 5/37 (2006.01)
A61F 5/058 (2006.01)
A61M 25/02 (2006.01)
A61M 25/06 (2006.01)

(52) U.S. Cl.
CPC ........ *A61F 5/3761* (2013.01); *A61F 5/05858* (2013.01); *A61M 25/06* (2013.01); *A61M 2025/0206* (2013.01); *A61M 2025/0213* (2013.01); *A61M 2025/026* (2013.01); *A61M 2025/028* (2013.01)

(58) Field of Classification Search
CPC ............ A61G 13/1245; A61G 13/1235; A61G 13/12; A61G 13/121; A47C 15/008; A61M 2025/0246; A61M 25/02; A61M 5/52; A61M 2025/0213; A61M 25/06; A61M 2025/026; A61M 2025/028; A61B 19/00; A61F 5/3761; A61F 5/05858
See application file for complete search history.

(56) References Cited

U.S. PATENT DOCUMENTS

| 1,389,741 A | | 9/1921 | Cotton |
| 2,318,864 A | * | 2/1940 | Jackson |
| 2,693,794 A | | 11/1954 | Neville |
| 3,196,870 A | * | 7/1965 | Sprecher ............ A61F 5/05858 128/877 |
| 3,295,518 A | | 1/1967 | Hazlewood et al. |
| 3,521,625 A | | 7/1970 | Mackey |

(Continued)

OTHER PUBLICATIONS

File History of U.S. Appl. No. 14/632,834, filed Feb. 26, 2015 and entitled: "Easy Chart Tagged Devices" (access is obtained through the USPTO records).

*Primary Examiner* — Ophelia A Hawthorne
(74) *Attorney, Agent, or Firm* — Mayer Brown LLP

(57) ABSTRACT

Embodiments for intravenous extremity supports for pediatric and adult patients that allow health care workers to visually assess and/or palpate an extremity during IV therapy without removing the extremity support are disclosed. Embodiments of extremity supports comprise a stabilizer and at least one window. In one embodiment, the window is a transparent portion of the stabilizer. In another embodiment, the window is an opening in the extremity support. In yet another embodiment, a window is an area of the extremity support that does not impede a health care worker's view of the lower part of an extremity.

19 Claims, 58 Drawing Sheets

(56) References Cited

U.S. PATENT DOCUMENTS

| | | | | |
|---|---|---|---|---|
| 3,719,187 A | * | 3/1973 | Ulansey | A61F 5/05866 602/6 |
| 3,724,456 A | | 4/1973 | Waxman | |
| 3,896,799 A | | 7/1975 | Seeley | |
| 3,901,227 A | | 8/1975 | Klatskin | |
| 3,976,066 A | * | 8/1976 | McCartney | A61F 15/008 128/879 |
| 4,043,330 A | | 8/1977 | Bansal | |
| D263,423 S | | 3/1982 | Aslanian | |
| 4,503,849 A | * | 3/1985 | Morgan | A61M 5/52 128/877 |
| 4,563,177 A | * | 1/1986 | Kamen | A61M 5/158 128/DIG. 26 |
| 4,782,825 A | | 11/1988 | Lonardo | |
| 4,870,976 A | | 10/1989 | Denny | |
| 1,919,150 A | | 4/1990 | Grant | |
| 4,928,677 A | * | 5/1990 | Barber | A61F 5/05866 2/11 |
| 4,982,744 A | | 1/1991 | Stanec | |
| 5,020,515 A | | 6/1991 | Mann et al. | |
| 5,025,801 A | | 6/1991 | Callaway | |
| 5,083,575 A | | 1/1992 | Jones | |
| 5,131,412 A | | 7/1992 | Rankin | |
| 5,339,834 A | * | 8/1994 | Marcelli | A61F 5/3761 128/877 |
| 5,577,516 A | * | 11/1996 | Schaeffer | A61F 5/05866 128/858 |
| 5,601,597 A | | 2/1997 | Arrowood et al. | |
| 5,728,053 A | * | 3/1998 | Calvert | A61F 5/05858 128/877 |
| 5,832,928 A | | 11/1998 | Padilla, Jr. | |
| 5,845,643 A | | 12/1998 | Vergano et al. | |
| 6,113,577 A | * | 9/2000 | Hakky | A61M 5/425 128/DIG. 26 |
| 6,257,240 B1 | * | 7/2001 | Shesol | A61M 25/02 128/877 |
| 6,328,706 B1 | * | 12/2001 | Yattavong | A61F 5/05866 128/878 |
| 6,443,918 B1 | | 9/2002 | Wang | |
| 6,500,154 B1 | * | 12/2002 | Hakky | A61M 25/02 604/174 |
| 6,540,710 B1 | * | 4/2003 | Cruz | A61F 5/0118 128/878 |
| 6,723,061 B2 | * | 4/2004 | Williams | A61F 5/0118 602/16 |
| 7,033,330 B2 | * | 4/2006 | de Lint | A61F 5/013 602/16 |
| D541,934 S | | 5/2007 | Gomez | |
| 7,406,967 B2 | | 8/2008 | Callaway | |
| 7,837,641 B2 | | 11/2010 | Hoffman | |
| 8,277,419 B1 | * | 10/2012 | Spitaleri | A61M 25/02 604/179 |
| 2002/0147390 A1 | | 10/2002 | Markis et al. | |
| 2003/0055382 A1 | * | 3/2003 | Schaeffer | A61M 25/02 604/179 |
| 2005/0076921 A1 | * | 4/2005 | Rozier | A61M 25/02 128/877 |
| 2007/0187478 A1 | | 8/2007 | Durrell et al. | |
| 2012/0016312 A1 | * | 1/2012 | Brown | A61M 25/02 604/174 |
| 2012/0116277 A1 | * | 5/2012 | Mantilla | A61F 5/0118 602/21 |
| 2013/0178777 A1 | * | 7/2013 | DiLorenzo | A61F 5/048 602/36 |

* cited by examiner

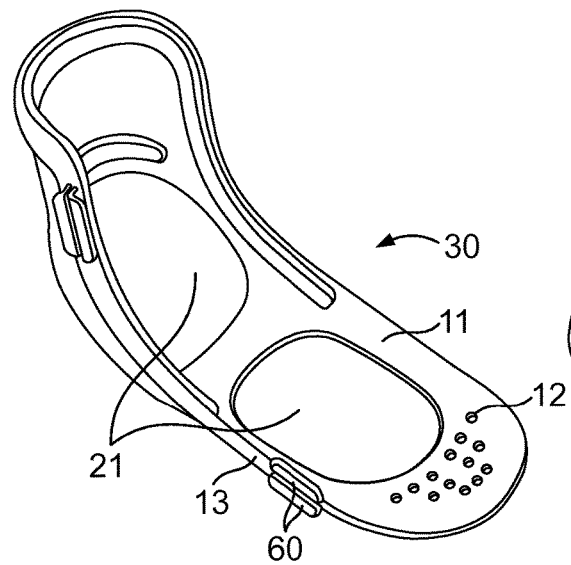
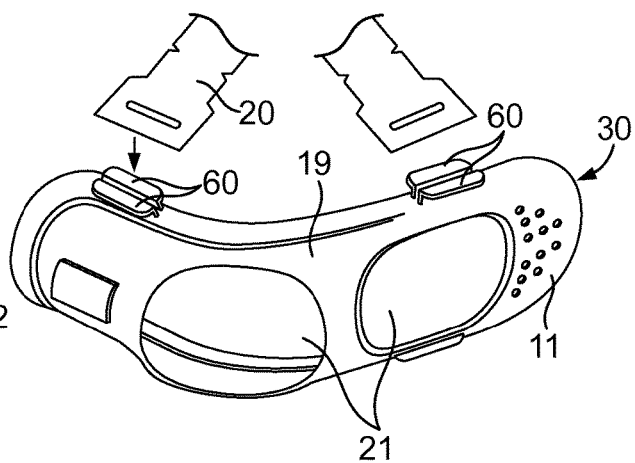
FIG. 19A
FIG. 19B
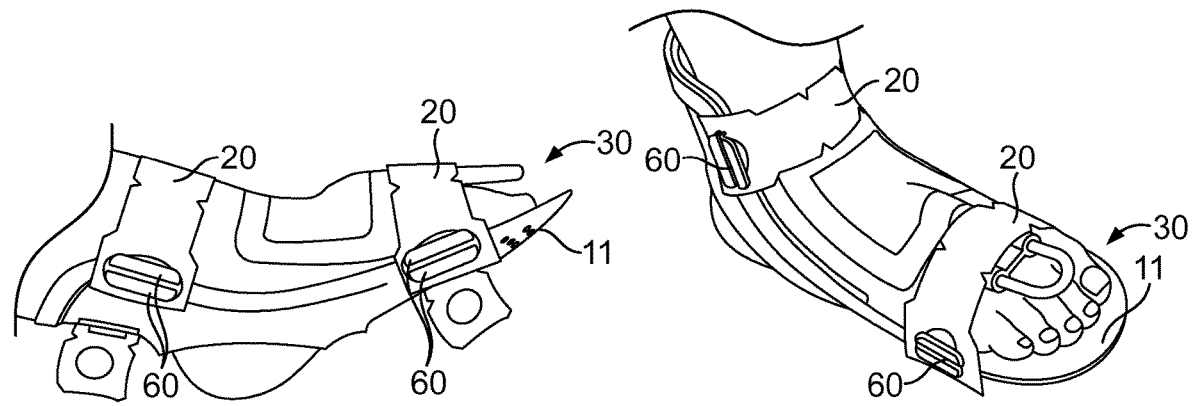
FIG. 19C
FIG. 19D

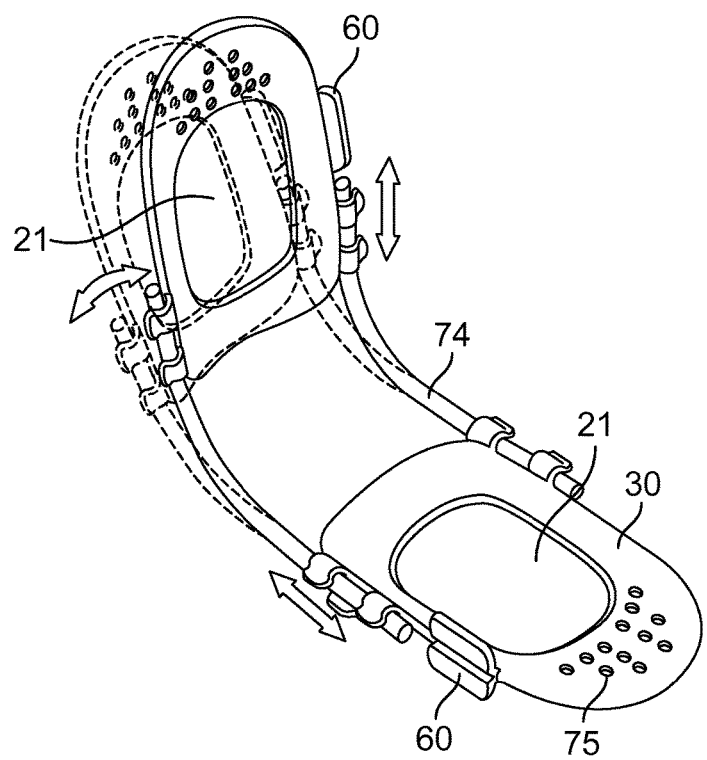
FIG. 19E
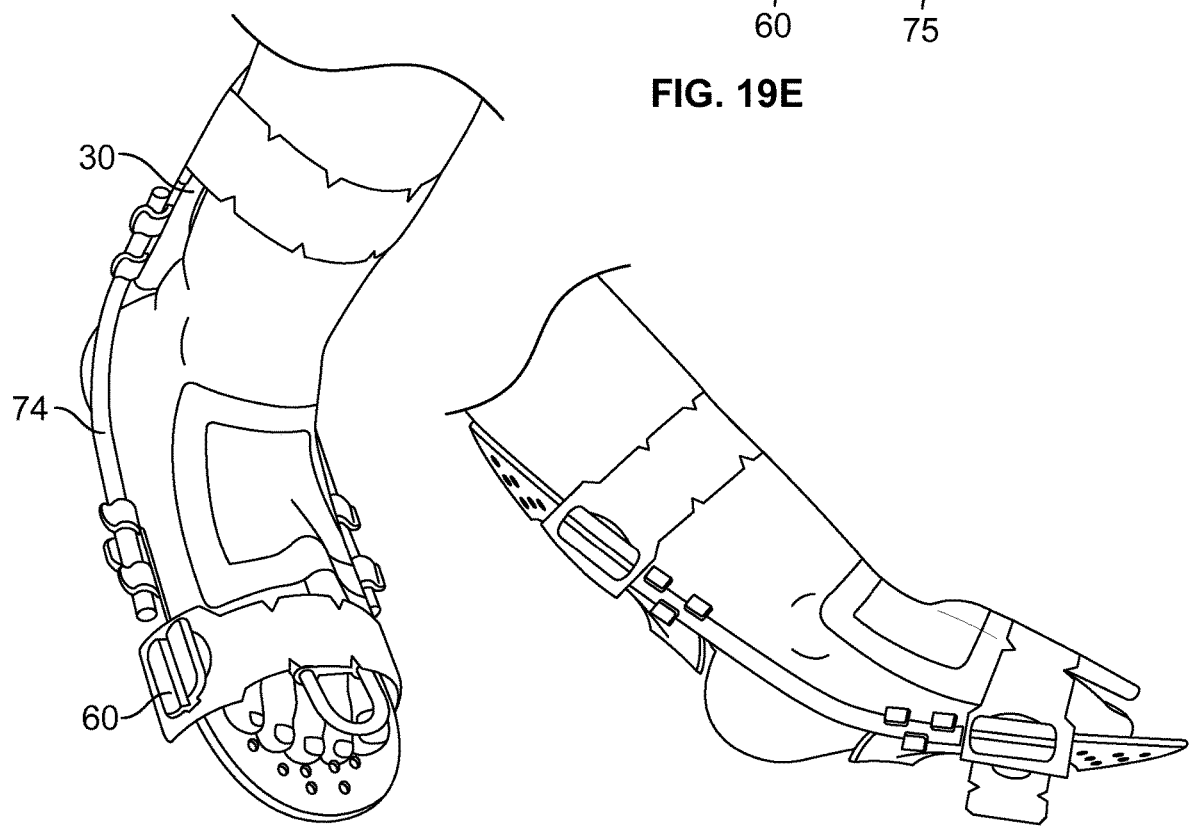
FIG. 19F
FIG. 19G

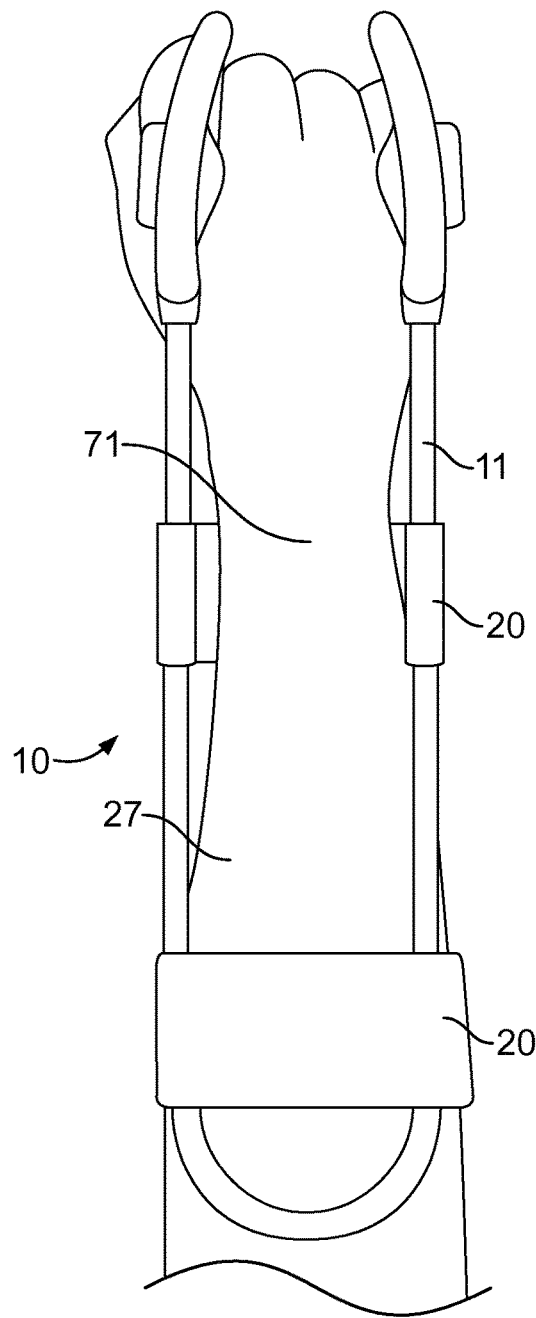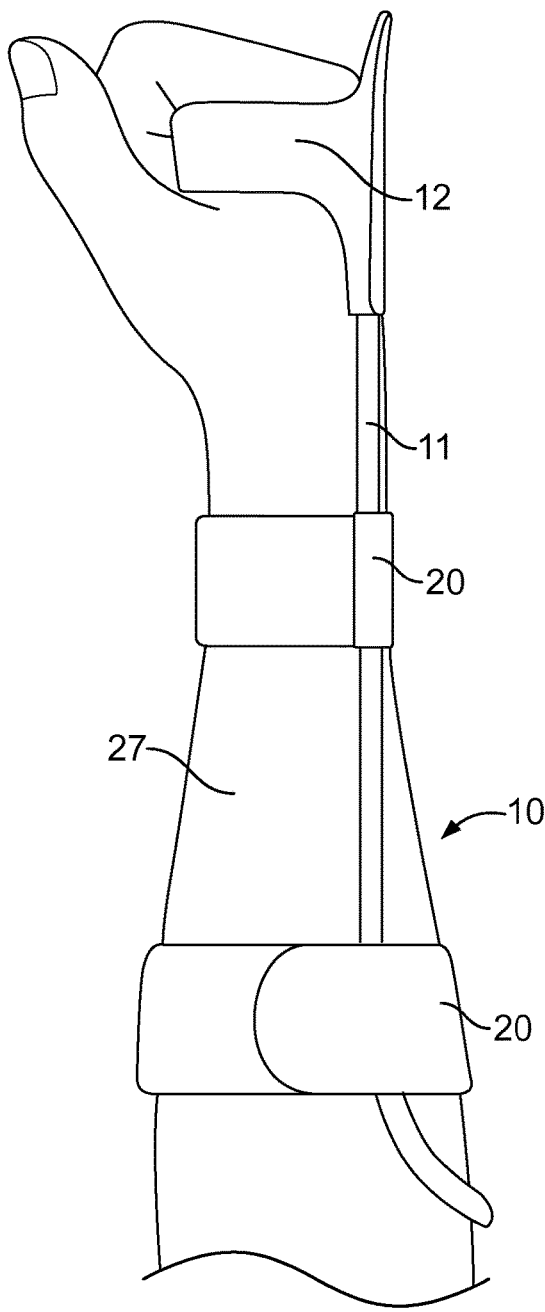
FIG. 27A  FIG. 27B

INTRAVENOUS EXTREMITY SUPPORT

RELATED CASES

This application claims priority to U.S. Provisional Application No. 61/692,120 filed on Aug. 22, 2012 and U.S. Provisional Application No. 61/794,512 filed on Mar. 15, 2013, which are incorporated herein by reference in their entirety to the full extent permitted by law.

FIELD

These embodiments relate to an extremity support which allows health care workers to assess the entire extremity, dorsal surface or back of hand, and volar surface or palmar/front surface, when the arms are at the patient's sides with the palms facing forward so the little finger is medial, next to body, and the thumb is lateral, away from body, for signs of infiltration and extravasation during peripheral intravenous (IV) therapy without removing the support.

BACKGROUND

Parenteral administration of therapy is a common and often life-saving medical intervention. Perhaps its most common form is peripheral intravenous (PIV) infusion, a high-volume, high-risk, high-cost therapy that affects virtually all patient populations in all health care settings. In this procedure, an over-the-catheter needle breaks a patient's skin and enters a vein. The needle is then removed, and the catheter remains in the vein. The catheter, along with additional equipment, delivers therapeutic infusates, such as antibiotics, hydration fluids, hyperalimentation, pain management drugs, chemotherapy drugs, indigestible drugs, or blood products into the body. Patients may receive IV or other parenteral therapy for a few hours, a few days, a few weeks, a few months, or even years.

On the human body, there are a number of possible venipuncture sites. The scalp, upper extremities, and lower extremities contain many peripheral venipuncture sites. The major superficial veins of the scalp are the frontal, superficial temporal, posterior auricular, supraorbital, occipital, and posterior facial. In the upper extremity, superficial venipuncture sites include the digital, cephalic, basilic, and median basilic veins located in the antecubital or elbow area of the arm, as well as the dorsal venous arch and dorsal metacarpals. The saphenous veins, the median marginal veins, and the veins of the dorsal arch of the lower extremities are also used.

The selection of an IV site depends on a host of considerations, including the age of the patient, condition of the patient, what kind of fluid is to be infused, rate at which the fluid is to be infused, and so forth. In general, if the patient is an adult, the best venipuncture sites, in order of preference, are the lower arm and hand, the upper arm, and the antecubital fossa. If the patient is an infant the possible IV sites include the hand, the lower arm, the upper arm, and the antecubital fossa. Additionally, a foot or leg, saphenous vein, provided the patient is not walking, or a scalp vein may be used when other peripheral attempts have failed.

Needles and catheters of various sorts are used for IV infusions. In the past, the same needle used to puncture the vein was also used for infusing the fluid. Present practice, however, is to infuse the fluid through a catheter that is planted with a needle, which is then withdrawn. Currently, there are two major types of catheters—namely, over-the-needle catheters and through the-needle catheters. A third type, steel butterfly needles, formerly used in treating children, has been superseded by over-the-needle catheters and the Infusion Nurse Society ("INS") does not recommend use of steel butterfly needles.

Although IV therapy offers patients many benefits, it poses a severe danger if not properly monitored. Of course, the insertion procedure itself and the constant presence within the vein of the needle or catheter bear a risk of injury to the patient. But these injuries become vastly more dangerous if they lead to infiltration or extravasation. Infiltration occurs when non-vesicant drugs or fluids are inadvertently administered into the subcutaneous tissue. In close relation, extravasation occurs when vesicant drugs or fluids are inadvertently administered into the subcutaneous tissue. Causes of infiltration and extravasation include: needle or catheter puncture of the posterior wall during insertion or caused by the needle, catheter, or patient movement, which erodes the vein wall; widening of the gaps between the cells of the vein wall due to inflammation of the insertion site; and venous blood flow restriction proximal to the insertion site. Infusion of a vesicant can cause vessel damage, which increases risk for extravasation.

Infiltration and extravasation may severely injure the patient. The fluid may fill many small compartments within an extremity and result in compartment syndrome. Pressure from the excess fluid can damage nerves, arteries, and muscles. Within as little as four hours a patient may experience irreversible nerve damage. Infiltration and extravasation can also cause complex regional pain syndrome (CRPS), as well as tissue damage that may require surgical intervention.

Phlebitis or inflammation of the vein may also severely injure the patient if not treated immediately and properly. Vein trauma during insertion, using a vein that is too small, using a catheter that is too big, and prolonged use of the IV sites are all contributing factors to the development of phlebitis. Additionally, irritating drugs, with very high pH or very low pH, can cause the onset of phlebitis after one infusion.

To minimize the risk of needle and/or catheter injuries to the vein, health care providers use extremity supports to stabilize the limb during IV therapy. These supports are used near joints to maintain the extremity and the catheter in a safe, functional position. For example, because of the common use of the lower arm and hand, health care providers often use arm supports. Leg supports are also commonly used extremity supports. Further, it has been an INS standard to use support such as IV boards at areas of flexion. Historically, nurses assembled arm supports with a short board and gauze or tape. But these restraints proved uncomfortable. For that reason, various suggestions for arm support improvements emerged. These suggestions focused on contouring the board to the arm, palm, or a combination thereof, or layering the board with a soft cushioned material to improve patient comfort. However, these arm supports prevent proper assessment of the extremity and may cause severe injury to the patient. Specifically, merely viewing the injection site fails to reduce the risk of infiltration and extravasation because the IV site often faces up, and the fluid follows gravity's pull and travels down to pool in the lower portion of the extremity. For example, infiltration or extravasation during IV therapy through the arm or the back of the hand can settle in a patient's palm or forearm. Consequently, any health care worker who merely inspects the injection and infusion site of a patient, whose palm and forearm are blocked by an arm support, may fail to detect early infiltration.

Assessment of the extremity receiving IV therapy can prevent severe patient injuries caused by infiltration and extravasation. Early signs and symptoms of infiltration and extravasation include local edema, redness or skin blanching, warmth or coolness of skin, leakage at the puncture site, pain, and feelings of tightness. Touch-Look-Compare is one program designed to bring awareness of the dangers of IV therapy and assist in the early detection of the signs and symptoms of infiltration and extravasation. To that end, Touch-Look-Compare stresses that health care workers should check the extremity receiving IV therapy hourly. Similarly, the INS has taken the position that health care workers should assess the insertion site during infusion at least every four hours, and every hour for neonatal or pediatric patients. Thus, both the Infusion Nurses Society and the Touch-Look-Compare program emphasize the importance for health care workers to view and palpate the extremity to detect infiltration or extravasation early to prevent severe patient injury.

However, currently marketed extremity supports amplify the dangers of infiltration and extravasation. Particularly, current extremity supports make assessment and inspection of the extremity a tedious process because health care workers cannot view or palpate the extremity in its entirety while the patient wears these supports. Instead, health care workers must remove and replace the extremity support multiple times a day (including up to 24 times a day for a pediatric patient), causing the patient anxiety, and consuming extensive amounts of the health care worker's time.

Yet, this practice of removing an extremity support is currently not being performed by many busy health care workers. For instance, many nurses do not have the time to unwrap a heavily taped IV site every hour for inspection. Hourly inspection of the top of a patient's hand is demanding enough. There is a significant need to improve functionality of the extremity supports to allow overall assessment of the extremity in a quick and efficient manner.

In view of the above, there is a continuing need for extremity supports to stabilize joints during IV therapy. However, current extremity supports prevent complete visualization and palpation by health care workers of much of the extremity. The present embodiments seek to solve that problem.

SUMMARY

Described herein are embodiments of an IV extremity support that allow health care workers to view an extremity during IV therapy without removing the support. Additionally, the embodiments will avoid patient discomfort and annoyance at the hourly removal and reapplication of the extremity support. In all, the easy assessment of the extremity will provide greater safety over current extremity supports by making health care workers' assessment easier and the patient more comfortable.

In one embodiment, the extremity support is an arm support. In another embodiment, the extremity support is a leg support. Embodiments of the extremity support comprise a stabilizer and a window. In one embodiment, the window is an opening in the stabilizer. In another embodiment, the window is a transparent portion of the stabilizer. In yet another embodiment, the window is an area of the extremity support that does not impede or impair visualization of the extremity.

A further embodiment of an extremity support comprises a stabilizer, at least one strap and a means for closing the strap around a patient, where the strap braces the extremity against the stabilizer. Another embodiment of an extremity support comprises at least one strap, a means for affixing the strap to the stabilizer, and a means for closing the strap around a patient, where the strap braces the extremity against the stabilizer.

In an additional embodiment, the extremity support comprises a stabilizer, a slit, a channel, or an opening, allowing at least one strap to go through the stabilizer to help reduce movement of the stabilizer and/or the strap. In yet another embodiment, the extremity support comprises a stabilizer that contains at least one tab, hook, button, anchor, knob, or protrusion, and at least one strap, wherein the strap is affixed, secured, place, and/or attached to the at least one tab, hook, anchor, knob, or protrusion.

In another embodiment, the extremity support for use in intravenous therapy comprises a stabilizer and at least one window, wherein the extremity support does not prevent visualization of the extremity when affixed to a patient in need thereof. In still a further embodiment, the extremity support for use in intravenous therapy comprises a stabilizer, at least one window, and at least one strap; wherein when the extremity support is affixed to a patent's extremity, the window allows for visualization of the extremity without removal of the extremity support; and wherein the strap secures the extremity support to the patient's extremity.

In still another embodiment, an arm support for use in intravenous therapy comprises a stabilizer, at least two windows, and at least one strap; wherein the stabilizer further comprises at least one opening to accommodate the strap and at least one anchor; wherein the strap is affixed to the anchor; and wherein when the extremity support is affixed to a patient's extremity, the windows allow for visualization of the patient's extremity without the removal of the extremity support.

BRIEF DESCRIPTION OF THE FIGURES

The accompanying drawings illustrate various embodiments of an extremity support. Corresponding reference characters refer to corresponding parts throughout the several views of the drawings, and in which:

FIGS. 19A-19D are embodiments to a leg support embodiment, where the stabilizer comprises at least one anchor to assist in securing the strap to the stabilizer.

FIGS. 19E-19J are embodiments to an adjustable leg support embodiment, where the stabilizer comprises two wires which slide into the stabilizers, making the foot support adjustable.

FIG. 26B is a close-up view of a slit or guide in an embodiment of an arm support embodiment. FIGS. 26C-26E are close-up views of anchors in embodiments of an arm support embodiment.

FIG. 27A is a plan view of the top of an arm support, where the support is closed around a patient.

FIG. 27B is a plan view of the side of the arm support, where the support is closed around a patient.

DETAILED DESCRIPTION

A. Definitions and General Information

Figure 1A:
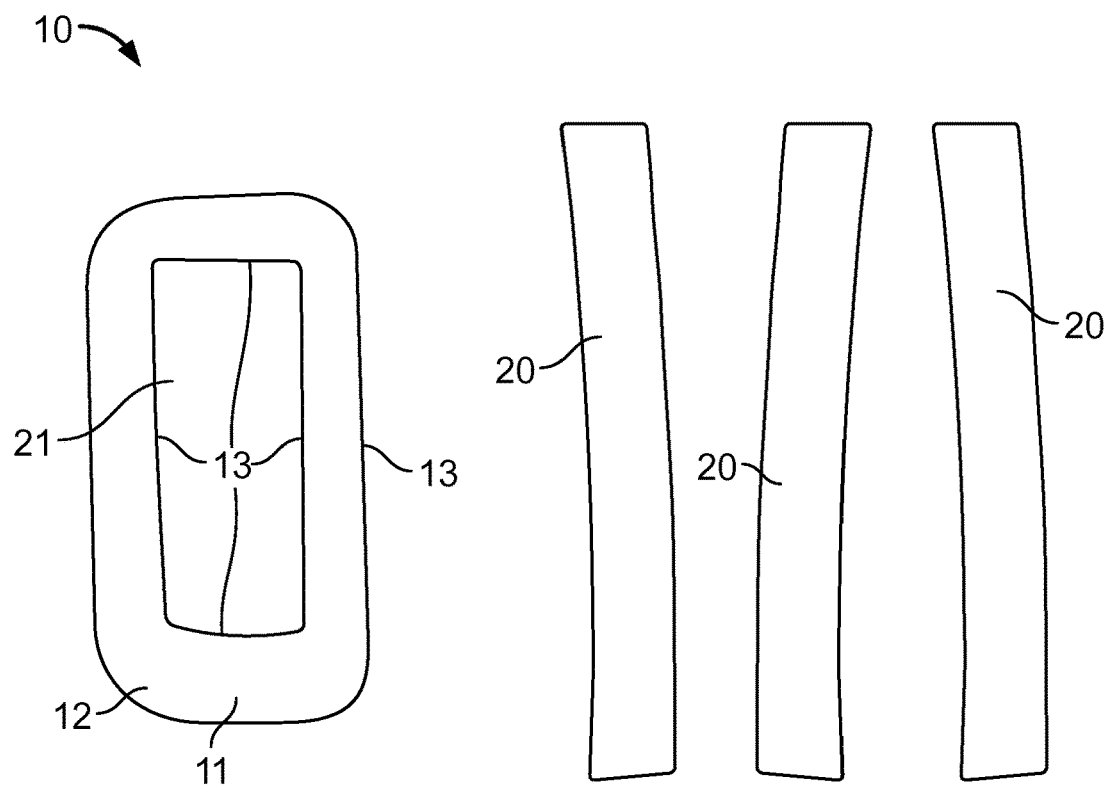
FIG. 1A is a plan view of the top of an arm support embodiment, where the straps are not permanently affixed to the stabilizer.
Figure 1B:
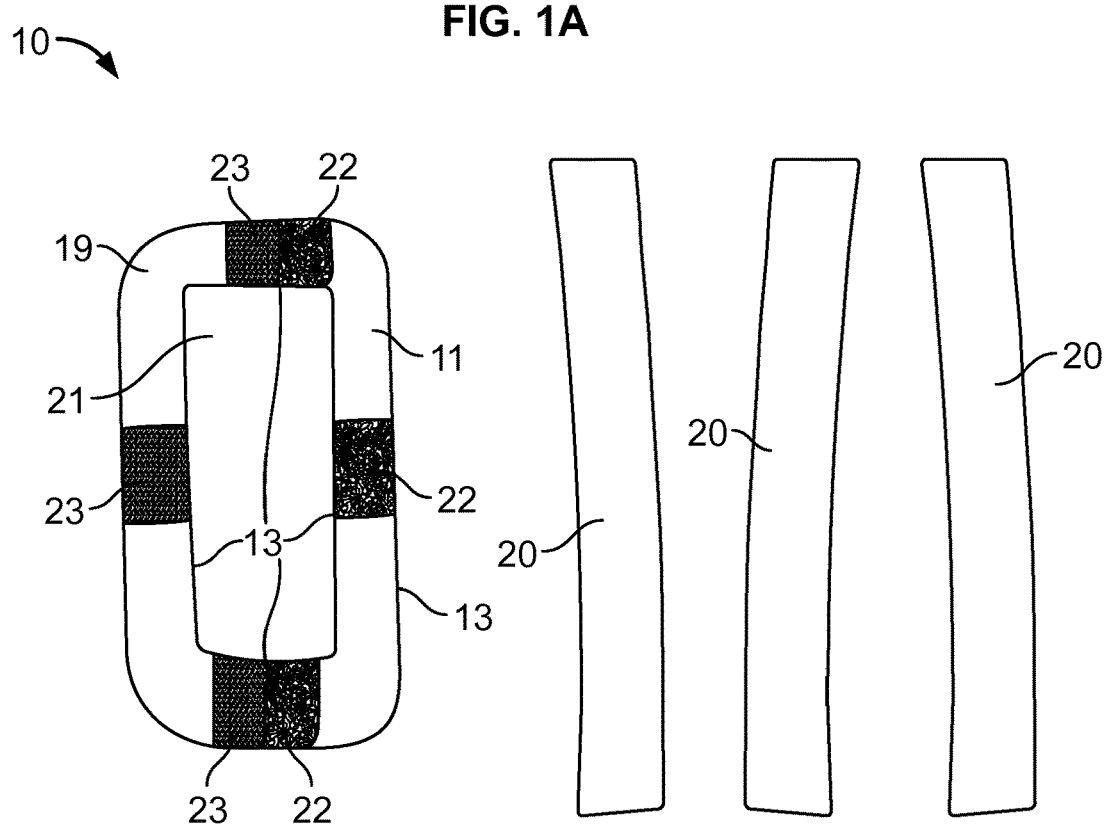
FIG. 1B is a plan view of the bottom of the arm support embodiment, where the straps are not permanently affixed to the stabilizer.
Figure 1C:
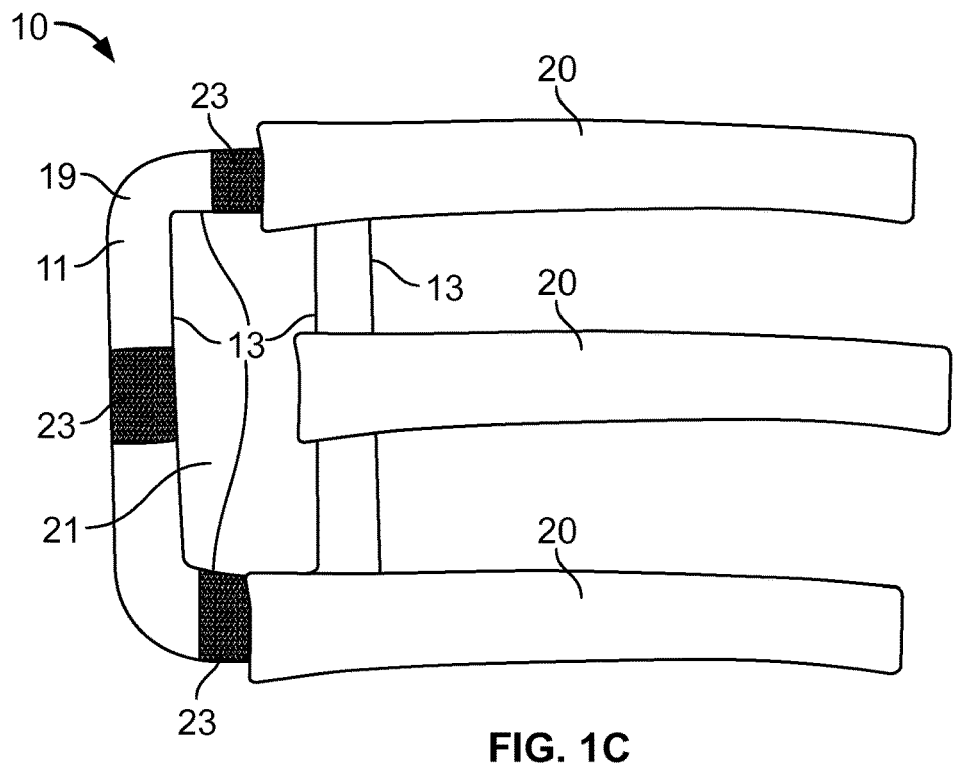
FIG. 1C is a plan view of the bottom of the arm support embodiment, where the straps are affixed to the bottom of the stabilizer.

The use of the terms "a," "an," and "the" and similar references in the context of this disclosure (especially in the context of the following claims) are to be construed to cover both the singular and the plural, unless otherwise indicated herein or clearly contradicted by context. All methods and individual method steps described herein can be performed in any suitable order or simultaneously, unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope, or range of equivalents, to which the appended claims are entitled. No language in the specification should be construed as indicating any non-claimed element as essential to the practice of the present disclosure.

All references, including printed publications, patent applications, and patents, cited herein are hereby incorporated by reference to the same extent as if each reference were individually and specifically indicated to be incorporated by reference and were set forth in its entirety herein.

Alternative embodiments of the claimed disclosure are described herein. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the embodiments to be practiced otherwise than as specifically described herein.

Accordingly, the embodiments include all modifications and equivalents of the subject matter recited in the claims appended hereto as permitted by applicable law. Moreover, any combination of the elements disclosed herein in all possible variations thereof is encompassed by this disclosure, unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately," when referring to a numerical value, shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors that may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios, and ranges of ratios that can be formed by, or derived from, any of the data disclosed herein represent further embodiments of the present disclosure and are included as a part of the disclosure as though they were explicitly set forth. This includes ranges that can be formed that do or do not include a finite upper and/or lower boundary. Accordingly, a person of ordinary skill in the art most closely related to a particular range, ratio, or range of ratios will appreciate that such values are unambiguously derivable from the data presented herein.

"Affixing means," as used herein, includes, but is not limited to, methods and/or materials for attaching one object or thing to another.

"Anchor" as used herein, includes, but is not limited to, any material, object, or device that binds, secures, holds, or grasps a strap or other object to the stabilizer. For example, as used herein, an anchor may include a tab, hook, button, cleat, strip, knob, projection, or other protrusion.

"Bottom," as used herein to refer to the stabilizer, includes, but is not limited to, the surface of the stabilizer that faces away from the extremity.

"Closure means," as used herein, includes, but is not limited to, a method and/or material to attach an extremity support to a patient.

"Contoured," as used herein, includes, but is not limited to, molded or shaped to fit a certain configuration. "Contoured" additionally includes, but is not limited to, any shape that provides comfort to a patient. "Contoured" further includes, but is not limited to, bendable or shaped to fit a patient at the time of application.

"Corner," as used herein, includes, but is not limited to, a place where two converging sides meet at the vertex of an angle.

"Extravasation," as used herein, includes the inadvertent administration of a vesicant fluid or medication into surrounding tissue.

"Extremity," as used herein, includes, but is not limited to, a limb or portion of a limb, such as a leg, ankle, foot, toe, arm, wrist, hand, finger, thumb, neck, head, wing, tail, claw, paw, hoof, or fin.

"Extremity support surface," as used herein, includes, but is not limited to, the surface of the stabilizer that faces an extremity. "Extremity support surface" additionally includes the surface of the stabilizer that contacts the patient.

"Forearm," as used herein, includes, but is not limited to, the ventral part of the arm between the elbow and the wrist. As used herein, "the side of the forearm" includes, but is not limited to, the part of the arm that is between the center of the forearm, between the radius and ulna, and the dorsal side of the forearm.

"Infiltration," as used herein, includes, but is not limited to, the inadvertent administration of a non-vesicant fluid or medication into surrounding tissue.

"Infusion site," as used herein, includes, but is not limited to, the area of fluid delivery, which is proximal to the insertion site.

"Insertion site," as used herein, includes, but is not limited to, any wound, opening, or lesion in the skin, or more than one wound, opening, or lesion, such as those made by needles and/or those made for peripheral or midline catheters, central venipuncture venous access catheters, or peripherally inserted central catheter (PICC) line. "Insertion site" may also include accompanying equipment—for instance, equipment present at an intravenous site, such as an IV catheter, extension tubing, Luer-Lok™ tubing, a loop of tubing, a catheter, locking mechanism (e.g., Luer-Lok™), extension tubing, transparent dressing, securement devices, tape, or wound, opening, and lesion dressing materials such as gauze.

"Knuckle rest," as used herein, includes, but is not limited to, a part of the extremity support surface in an arm support embodiment that supports the palm side knuckles.

"Leg support," as used herein, includes, but is not limited to, a device that stabilizes the leg and/or the foot.

"Lower part of an extremity," as used herein, includes, but is not limited to, the portion of the extremity closest to the ground when the patient is positioned for IV infusion.

"Means for closing," as used herein, includes, but is not limited to, a method and/or material to fasten objects together.

"Padding," as used herein, includes, but is not limited to, a lining, cushion, soft plastic, soft porous cloth, gauze, stretch wrap, foam tape, foam of varying thicknesses, or other suitable substance.

"Palm," as used herein, includes, but is not limited to, the part of the ventral surface of the hand that extends from the wrist to the bases of the fingers.

"Palpate," as used herein, includes, but is not limited to, to examine by touch.

"Patient," as used herein, includes, but is not limited to, a human or other animal that needs to have an extremity stabilized.

"Plastic," as used herein, includes, but is not limited to, polystyrene, polycarbonate, acrylics, silicone rubber, polyethylene, polypropylene, polyester, polyimide, and synthetic rubbers. "Plastic," as used herein, also includes plastic resins, for example, polypropylene homopolymer. Further, as used herein, "polypropylene" includes, but is not limited to, oriented polypropylene and biaxial oriented polypropylene. As used herein, "polycarbonate" includes, but is not limited to, brands such as Lexan®, Makrolon®, or Makroclear®. As used herein, "polystyrene" includes, but is not limited to, Styrofoam®. As used herein, "acrylics" include, but are not limited to, those sold under trade names such as Lucite®, Optix®, Perspex®, Altuglas®, or Plexiglass®. As used herein, "polyethylene" includes, but is not limited to, high-density polyethylene, low-density polyethylene, ethylene vinyl acetate, or polyvinyl chloride. As used herein, "polyester" includes, but is not limited to, semi-crystalline polyethylene terephthalate, amorphous polyethylene terephthalate, recycled polyethylene terephthalate, or polyethylene terephthalate glycol. As used herein, "synthetic rubbers" include, but are not limited to, polychloroprene or polyisoprene.

"Rectangular," as used herein, includes, but is not limited to, a polygon with four sides and four corners. "Rectangular" additionally includes, but is not limited to, one to four rounded corners and/or one to four rounded sides.

"Rounded corner," as used herein, includes, but is not limited to, a side that bends without an angle. "Rounded corner" additionally excludes a vertex where straight sides meet.

"Rounded side," as used herein, includes, but is not limited to, a side that does not form a straight line. "Rounded side" additionally includes, but is not limited to, a side that is concave, convex, a mixture thereof, or straight, concave, and/or convex.

"Side of a leg," as used herein, includes, but is not limited to, the part of a leg that is not anterior or posterior.

"Sides," as used herein in reference to the stabilizer, includes, but is not limited to, the surface of the stabilizer that connects the extremity support surface and the bottom.

"Stabilizer," as used herein, includes, but is not limited to, any material or object that an extremity may be braced against, so as to inhibit the extremity's movement.

"Strap," as used herein, includes, but is not limited to, one or more pieces of material that brace or secure a stabilizer to an extremity.

"Toe rest," as used herein, includes, but is not limited to, a part of the extremity support surface in a leg support embodiment that supports the patient's toes.

"Transparent," as used herein, includes, but is not limited to, any material or object that transmits rays of light through its substance so that bodies situated beyond or behind can be distinctly seen. "Transparent" also includes, but is not limited to, easily seen through. Further, "transparent," as used herein, includes, but is not limited to, any material or object wherein a portion of that object is see-through, regardless of whether the remaining portion of that object or material is cloudy or opaque.

"Vesicant," as used herein, includes, but is not limited to, an agent capable of causing vein damage, blistering, tissue sloughing, or necrosis when administered into tissue surrounding the insertion site.

"Window," as used herein, includes, but is not limited to, one or more openings in the stabilizer that allow visualization and/or palpation of the extremity through the stabilizer. A "window" further includes at least one transparent portion of the stabilizer. Additionally, a "window" includes one or more areas where the stabilizer does not impede visualization and/or palpation of the extremity.

B. Description

Because embodiments may take various forms, the description below of several embodiments is made with the understanding that the present disclosure is to be considered as an exemplification of the claimed subject matter, and is not intended to limit the claims to the specific embodiments illustrated and/or described. The headings used throughout this disclosure are provided for convenience only and are not to be construed to limit the claims in any way. Embodiments illustrated under any heading may be combined with embodiments illustrated under any other heading.

The various embodiments disclosed and described herein present extremity supports that comprise a stabilizer 11 and at least one window 21. In some embodiments, the stabilizer 11 has an extremity support surface 12, a bottom 19, and sides 13. In other embodiments, the stabilizer 11 has two extremity support surfaces 12 and sides 13. In yet another embodiment, the stabilizer 11 has an extremity support surface 12 and a bottom 19. Still other embodiments of extremity supports further comprise at least one strap 20, a means for affixing 22 the strap 20 to the stabilizer 11, and a means for closing 23 the strap 20 around a patient. Yet other embodiments further comprise at least one strap 20 and a means for closing 23 the strap 20 around a patient.

A stabilizer 11 can be made from any material. Materials can include, but are not limited to, metal, plastic, wire, or wood. A stabilizer 11 can also be made of mixtures of metal, plastic, wire, or wood. In one embodiment, the stabilizer 11 is made of metals, including but not limited to aluminum, transparent aluminum, stainless steel, titanium or titanium alloys, or a mixture thereof. In another embodiment, the stabilizer 11 is made of wood, such as solid wood or compressed wood. In yet another embodiment, the stabilizer 11 is made of plastic. In a further embodiment, the stabilizer 11 is made of wire. In still another embodiment, the stabilizer is made of wire and plastic. In still another embodiment the stabilizer is made from metal and plastic. In another embodiment, the stabilizer 11 is a single piece. In a further embodiment, the stabilizer 11 comprises multiple pieces.

In one embodiment, the stabilizer 11 is solid. In another embodiment, the stabilizer 11 is hollow. In still another embodiment, the stabilizer 11 is rigid. In a further embodiment, the stabilizer 11 is bendable. In yet another embodiment, the stabilizer 11 has both bendable and rigid portions or properties.

A stabilizer 11 can be of any size necessary to fit a patient and stabilize an extremity. In one embodiment, the stabilizer 11 will fit an infant. In another embodiment, the stabilizer 11 will fit a toddler. In still another embodiment, the stabilizer 11 will fit a child. In a further another embodiment, the stabilizer 11 will fit a teenager. In yet another embodiment, the stabilizer 11 will fit an adult.

The stabilizer may, or may not, be transparent. In one embodiment, the stabilizer 11 is transparent. In still another embodiment, the stabilizer 11 is opaque. In yet another embodiment, the stabilizer 11 is translucent. In a further embodiment, a portion of the stabilizer 11 is opaque and a portion of the stabilizer 11 is transparent. The stabilizer may or may not be colored. In one embodiment the stabilizer is a color. For example, in one embodiment, the stabilizer is any color selected from the group consisting of blue, orange, white, red, yellow, green, purple, pink, black, brown, teal, fuchsia, silver, or gold.

A stabilizer 11 can be any shape. In one embodiment, the stabilizer 11 is a polygon. In a further embodiment, the stabilizer 11 is a rectangle. In yet another embodiment, the stabilizer 11 is a triangle. In a further embodiment, the stabilizer 11 is a square. In still another embodiment, the stabilizer 11 is a circle. In another embodiment, the stabilizer 11 is an ellipse. In yet another embodiment, the stabilizer 11 is oval. In a further embodiment, the stabilizer 11 is shaped like an hourglass. In another embodiment, the stabilizer 11 is shaped like the letter "T." In still another embodiment, the stabilizer 11 is shaped like the letter "L." In yet another embodiment, the stabilizer 11 is shaped like the letter "J." In another embodiment, the stabilizer 11 is "Π" shaped. In still another embodiment, the stabilizer 11 is shaped like the letter "U." In yet another embodiment, the stabilizer 11 is spoon-shaped. In a further embodiment, the stabilizer 11 is shaped like the number eight.

An extremity support surface 12 may, or may not, be contoured to fit an extremity. In an arm support embodiment 10, the extremity support surface 12 is contoured to fit a right arm and/or a right hand. In another arm support embodiment 10, the extremity support surface 12 is contoured to fit a left arm and/or a left hand. In a further arm support embodiment 10, the extremity support surface 12 is contoured to fit a hand, and the extremity support has a knuckle rest. In yet another arm support embodiment 10, the knuckle rest protrudes from the stabilizer 11, allowing a patient to wrap his fingers around it. In yet another arm support embodiment, the extremity support surface 12 is contoured to fit the wrist. In an additional arm support embodiment, the extremity support surface 12 comprises slightly contoured sides that seem to cling to or hug the arm and/or slanted ends that allow neutral positioning of the hand and forearm. In a leg support embodiment 30, the extremity support surface 12 is contoured to fit a right leg and/or a right foot. In another leg support embodiment 30, the extremity support surface 12 is contoured to fit a left leg and/or a left foot.

The stabilizer's 11 sides 13 may be any height. In one embodiment, the sides 13 have a height between about 0.1 centimeter to about 10 centimeters. In another embodiment, the side's 13 height is about 0.25 centimeters to about 8 centimeters. In another embodiment, the side's 13 height is about 0.25 centimeters to about 3.0 centimeters. In still another embodiment, the side's height is about 0.3 centimeters to about 1.5 centimeters.

A stabilizer's 11 bottom 19 may be any shape or size. In one embodiment, the bottom 19 reflects the shape and size of the extremity support surface 12. In another embodiment, the bottom 19 is larger than the extremity support surface 12. In yet another embodiment, the bottom 19 is smaller than the extremity support surface 12. In still another embodiment, the bottom 19 is shaped different than the extremity support surface 12.

A stabilizer 11 may, or may not, have one or more straps 20 that are permanent or removable affixed to it by an affixing means 22. In one embodiment, the straps 20 are affixed to the extremity support surface 12. In another embodiment, the straps 20 are affixed to the bottom 19 of the stabilizer 11. In yet another embodiment, the straps 20 are affixed to the sides 13 of the stabilizer 11. In still another embodiment, the straps 20 are affixed to the sides 13, the bottom 19, and/or the extremity support surface 12 of the stabilizer 11. In a further embodiment, the straps may or may not have tape (e.g., single-sided tape or double-sided tape) applied to them to prevent movement of the straps and/or the extremity support on the patient's body.

In another embodiment, the stabilizer may or may not have one or more ventilation hole(s) or other opening(s). In these embodiments, the ventilation hole(s) or other opening(s) provide ventilation and/or air exposure to the extremity being supported. This ventilation or exposure to the air assists in preventing and/or reducing perspiration of the extremity, which assists in the patient's overall comfort and helps decrease or prevent the growth of bacteria on the extremity support.

Likewise, a stabilizer 11 may or may not be connected to the means for closing 23 the strap 20 around a patient. In one embodiment, the means for closing 23 the strap 20 around a patient are affixed to the extremity support surface 12. In another embodiment, the means for closing 23 the strap 20 around a patient are affixed to the bottom 19 of the stabilizer 11. In yet another embodiment, the means for closing 23 the strap 20 around a patient are affixed to the sides 13 of the stabilizer 11. In still another embodiment, the means for closing 23 the strap 20 around a patient are affixed to the strap 20 itself.

A stabilizer 11 may or may not have a method to attach straps built into the design. For example, in one embodiment, a stabilizer 11 comprises at least one anchor 60. The at least one anchor 60 may be on the bottom 19, sides 13, or surface 12 of the stabilizer 11. In another embodiment, the stabilizer 11 comprises at least two anchors 60, and in another embodiment, the stabilizer 11 comprises at least three anchors 60. In a further embodiment, the stabilizer 11 comprises more than three anchors 60. In yet another embodiment, the strap 20 attaches to the anchor 60, then the strap 20 wraps around the board. In another embodiment, the stabilizer 11 further comprises a slit 70 or an opening 70 to accommodate the strap 20. This slit 70 or opening 70 in the stabilizer 11 may be used to help hold the strap 20 in place on the anchor(s) 60. In yet another embodiment, the stabilizer 11 comprises multiple slits 70 or openings 70 to accommodate multiple straps 20 to prevent the straps 20 from slipping onto the stabilizer 11 and obstructing visualization of the palm, forearm, or palmar side of the arm. In still another embodiment, the stabilizer 11 comprises at least one notch(es) 80 or guide(s) 80 to accommodate the straps 20. In an additional embodiment, the at least one notch 80 or guide 80 may be on the bottom 19, sides 13, or surface 12 of the stabilizer 11. (See FIGS. 19A-19D; 25A-25D; and 26A-26F for examples of embodiments described in this paragraph.)

In another embodiment, the stabilizer 11, comprises grips, teeth, bumps or other texture on its surface 12 or bottom 19 to help prevent the strap 20 from slipping off of the stabilizer 11.

A stabilizer 11 may or may not be covered with padding. In one embodiment, the stabilizer 11 is at least partially covered with padding. In another embodiment, the stabilizer 11 is entirely covered with padding. In yet another embodiment, the padding is transparent.

In a further embodiment, the entire extremity support surface 12 is covered with padding. In one such embodiment, the extremity support may comprise a stabilizer 11 and at least one strap 20, wherein the entire extremity support surface 12 is covered with padding, and the at least one strap 20 is also covered with padding that is either permanently affixed thereto (e.g., the padding is sewn onto the strap or is bonded onto the strap with a glue or adhesive) or is removable. In another embodiment, the strap 20 provides sufficient padding without the need to affix additional padding thereto.

Extremity support embodiments may comprise one or more windows 21. In one embodiment, the window 21 is a transparent portion of the stabilizer 11 that allows for visualization of the extremity. In a further embodiment, the entire stabilizer 11 acts as a window 21, as the stabilizer 11 is transparent and allows for visualization of the extremity. In another embodiment, the window is a translucent portion of the stabilizer that allows for visualization of the extremity. In still another embodiment, the window 21 is an opening in the stabilizer 11 that allows for visualization and/or palpation of the extremity. In yet another embodiment, a window 21 is formed by the shape of the stabilizer, which exposes a portion of the extremity allowing for visualization and/or palpation. For example, an arm support embodiment wherein the stabilizer is shaped like the letter "T" forms a window on both sides of the vertical trunk of the "T," and may also comprise a window 21 above the horizontal cap of the "T," which allows for visualization and/or palpation of the forearm 27, palm 26, and fingers 29.

A window 21 may be square, round, rectangular, oval, elliptical, triangular, heart-shaped, star-shaped, "U-" or "X-" shaped, or any other useful or decorative shape. For example, in one embodiment, the window 21 is a polygon. In another embodiment, the window 21 is round. In yet another embodiment, the window 21 is rectangular. In a further embodiment, the window 21 is a triangle. In still another embodiment, the window 21 is a square. In another embodiment, the window 21 is a circle. In a further embodiment, the window 21 is an ellipse. In yet another embodiment, the window 21 is oval. In an additional embodiment, the window is a pentagon. In a further embodiment, the window is an octagon.

The window 21 may or may not be covered. In one embodiment, the window 21 is not covered. In another embodiment, one or more straps 20 cover the window 21. In still another embodiment, the window 21 is covered by a flap connected to the stabilizer 11. In a further embodiment, the window is covered by a flap connected to one or more straps 20. In yet another embodiment, a porous material covers the window 21. In a further embodiment, a translucent material covers the window 21. In yet another embodiment, an antimicrobial and/or antibacterial material covers the window. In a further embodiment, the window 21 may be covered with a material or object that is easily lifted or removed allowing for visualization and palpation of the site.

Arm support 10 embodiments may or may not have at least one window 21. In one embodiment of an arm support 10, the window 21 is adapted to provide a view of the palm and/or the forearm around the stabilizer 11. In another embodiment of an arm support 10, the window 21 is adapted to provide a view of the palm and/or the forearm through the stabilizer 11.

Leg support embodiments 30 may have at least one window 21. In one embodiment of a leg support 30, the window 21 is adapted to provide a view of a leg and/or a foot around the stabilizer 11. In another embodiment of a leg support 30, the window 21 is adapted to provide a view of the leg and/or the foot through the stabilizer 11.

In yet another embodiment, the leg support embodiment 30 comprises two stabilizers connected via two wires resulting in an adjustable leg support. Each piece has a window 21. In one embodiment, the length of the wire connecting the two stabilizers is between 9.0 and 20.0 cm. In another embodiment, the length of the wire is between 10.0 and 17.0 cm. In a preferred embodiment, the length of the wire is between 13.0 and 14.0 cm.

A strap 20 may be made of any material adapted to brace a stabilizer against an extremity. A strap 20 includes, but is not limited to, one or more pieces of any material, woven or nonwoven, preferably breathable, including, but not limited to, a tubular material such as a mesh, stretch wrap, burn net, gauze, cotton cloths or blends, latex-free materials, soft cloth, Lycra, nylon, single- or multiple-phase polymeric materials such as Tyvek or polypropylene and polytetrahydrofluoroethylene (PTFE, made by Gortex®), tape wrap, a porous mesh, a stretchy fabric, a transparent material such as certain plastics or nylons or blends. A strap 20 additionally includes combinations of these materials, as treatment of the material with porous polymers such as PTFE. A strap 20 may also be stretchable in one direction, in all directions, or may not stretch at all. Additionally, the straps 20 can be coated with a gripper elastic or stay-put silicon to prevent movement. Further, a strap 20 may contain double-coated tape that will affix to the strap 20 and the patient's skin or article of clothing to prevent movement of the strap 20 when affixed to the patient.

A strap 20 may be any shape so long as it secures the stabilizer to the patient. A strap 20 can be square, round, rectangular, tubular, "X"-shaped, or any other shape. In one embodiment, an "X"-shaped strap 20 crosses over and down to the opposite closure means. In another embodiment, one long strap 20 is used to secure the stabilizer 11 to the patient by making an X-shape with the strap 20 across the stabilizer 11. In use, a strap 20 with excess material may be cut to size after an extremity support 10 is applied to a patient.

One or more straps, 20 may secure the stabilizer 11 around a patient. In one embodiment, the extremity support has about one to about eight straps. In another embodiment, the extremity support has about one to about six straps. In still another embodiment, the extremity support has about one to about three straps. In yet another embodiment, the extremity support has about two straps. In a further embodiment, the extremity support has about one strap.

An affixing means 22 can attach the strap 20 to the stabilizer 11. An affixing means 22 may or may not be present. Affixing means 22 may include, but are not limited to, sewing, gluing with adhesives, ultrasonic welding, chemical bonding, or using other means, such as Velcro®, to affix one or more straps 20 onto the stabilizer 11. Adhesives that can be used to affix the straps 20 to the stabilizer 11 include, but are not limited to, acrylic-based adhesives, rubber-based and synthetic hot melt adhesives, silicone adhesives, heat-activated adhesives and thermoplastics, electrically conductive adhesives, medical grade and skin contact adhesives, direct and indirect food contact adhesives, removable adhesives, VHB and ultra-high adhesion adhesives, and low surface energy adhesives. In one embodiment, the stabilizer 11 affixes to the straps 20 by using gauze, flannel, or other soft breathable cloth cut on a bias, doubled with a pocket on the straps that the stabilizer can slide into. In another embodiment, the affixing means 22 is a hook fastener on the strap 20 and a loop material connected to the stabilizer 11. In yet another embodiment, the affixing means 22 is a loop fastener on the strap 20 and a hook material connected to the stabilizer 11. Strap(s) 20 can be affixed to the bottom 19, sides 13, or extremity support surface 12. Strap(s) 20 may also be ultrasonically welded to the stabilizer 11.

Means for closing 23 the strap 20 around a patient include, but are not limited to, tape and other adhesives, such as tape wrap, where fabric is against the skin and a peel-and-stick tape is on both ends, as well as nonadhesives, such as hook-and-loop fasteners (Velcro®), Velcro ONE-STRAPs®, hook-and-eye fasteners, ties, pins, clips, ultrasonic welding or glue, and other suitable products. Closure means 23 are not limited to one shape or size; for instance, Velcro® can take any form or shape, circle, square, or rectangle. In an embodiment, the closure means 23 is a hook fastener on a strap 20 and a loop material connected to the stabilizer 11. In another embodiment, the means for closure 23 is a loop fastener on a strap 20 and a loop material connected to the stabilizer 11. In yet another embodiment, the means for closing 23 is a strap 20 that affixes to itself with a hook-and-loop fastener. In a further embodiment, the means for closing 23 is an adhesive on a strap 20 that connects the strap 20 to the stabilizer 11. In another embodiment, the strap 20 may act as a loop fastener(s). For example, a strap 20 may be comprised on Veltex or Velstretch fabric, which can be used as the loop.

Padding may or may not be present on the stabilizer. Padding may be made of any material. Padding may be made of materials, such as, but not limited to, urethane foams, silicone foams, polyvinyl chloride foams, polyethylene foam, neoprene, santoprene, polyethylene foam, or a mixture thereof. In one embodiment, the stabilizer 11 is entirely covered with padding 24. In another embodiment, the stabilizer 11 is partially covered with padding 24. In yet another embodiment, the stabilizer 11 has no padding 24. In still another embodiment, the padding 24 is transparent. In yet another embodiment, the padding is translucent. In another embodiment, the padding 24 is opaque. In yet another embodiment, the padding 24 is partially transparent and partially opaque.

The extremity support may be adapted to work with an IV site guard, such as site guards sold under the trade name, I.V. House UltraDome® or I.V. House UltraDressing®.

In some embodiments, the extremity support for use in intravenous therapy comprises a stabilizer and at least one window, wherein the extremity support does not prevent visualization of the extremity when affixed to a patient in need thereof. In still a further embodiment, the extremity support for use in intravenous therapy comprises a stabilizer, at least one window, and at least one strap; wherein when the extremity support is affixed to a patent's extremity, the window allows for visualization of the extremity without removal of the extremity support; and wherein the strap secures the extremity support to the patient's extremity. The stabilizer may also comprise at least one slit to accommodate the strap. Moreover, the stabilizer may comprise at least one anchor and wherein the strap is affixed to the anchor.

In still another embodiment, an arm support for use in intravenous therapy comprises a stabilizer, at least two windows, and at least one strap; wherein the stabilizer further comprises at least one opening or slit to accommodate the strap and at least one anchor; wherein the strap is affixed to the anchor; and wherein when the extremity support is affixed to a patient's extremity, the windows allow for visualization of the patient's extremity without the removal of the arm support. In an additional embodiment, the arm support comprises more than one strap, wherein the straps are mesh, cloth, stretch warp, burn net, gauze, cotton cloths, or nylon. In yet another embodiment, the stabilizer is hourglass shaped and/or contoured to fit a patient's extremity (e.g., arm) and comprises ventilation holes. The stabilizer may also optionally comprise padding. Further, the stabilizer may be transparent. The stabilizer may also be made of plastic or wire.

In yet another embodiment, a leg support for use in intravenous therapy comprises a stabilizer, at least two windows, and at least one strap; wherein the stabilizer further comprises at least one opening to accommodate the strap and at least one anchor; wherein the strap is affixed to the anchor; and wherein when the leg support is affixed to a patient's extremity, the windows allow for visualization of the patient's extremity without the removal of the extremity support. In an additional embodiment, the leg support comprises more than one strap, wherein the straps are mesh, cloth, stretch warp, burn net, gauze, cotton cloths, or nylon. In yet another embodiment, the leg support further comprises two wires, which slide into the stabilizers, making the leg support adjustable to the size of the patient. In addition, these embodiments comprise at least one channel(s). This channel houses the wire and are adjustable to the patient's size and lock the wire into place once the appropriate size is determined. In another embodiment, the leg support comprises an opening to accommodate the heel of the patient's foot. The stabilizer may also optionally comprise padding. Further, the stabilizer may be transparent. The stabilizer may also be made of plastic or wire.

C. Examples

Figure 1D:
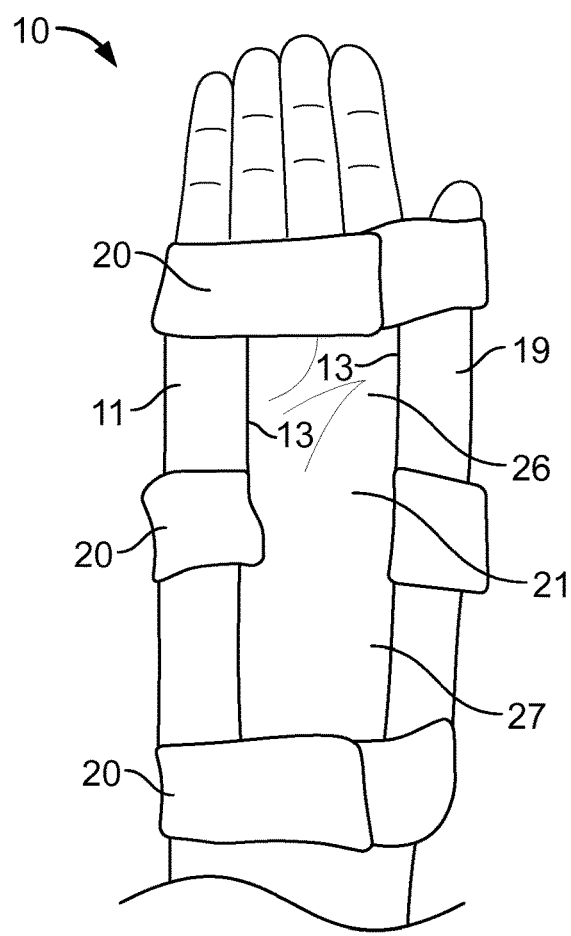
FIG. 1D is a plan view of the bottom of the arm support embodiment as shown in FIGS. 1A-1C, where the arm support is closed around a patient, and where the plan view shows the palm and the forearm through the stabilizer.
Figure 1E:
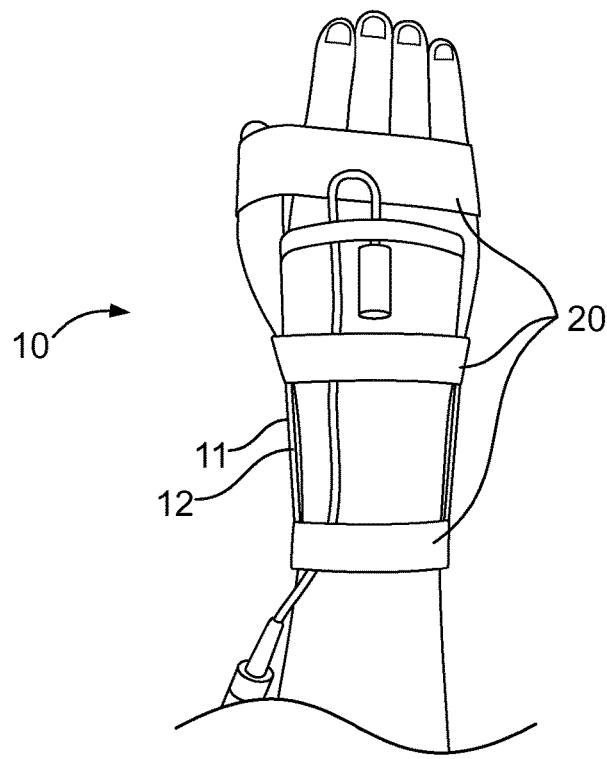
FIG. 1E is a plan view of the top of the arm support embodiment as shown in FIGS. 1A-1C, where the arm support is closed around a patient.
Figure 1F:
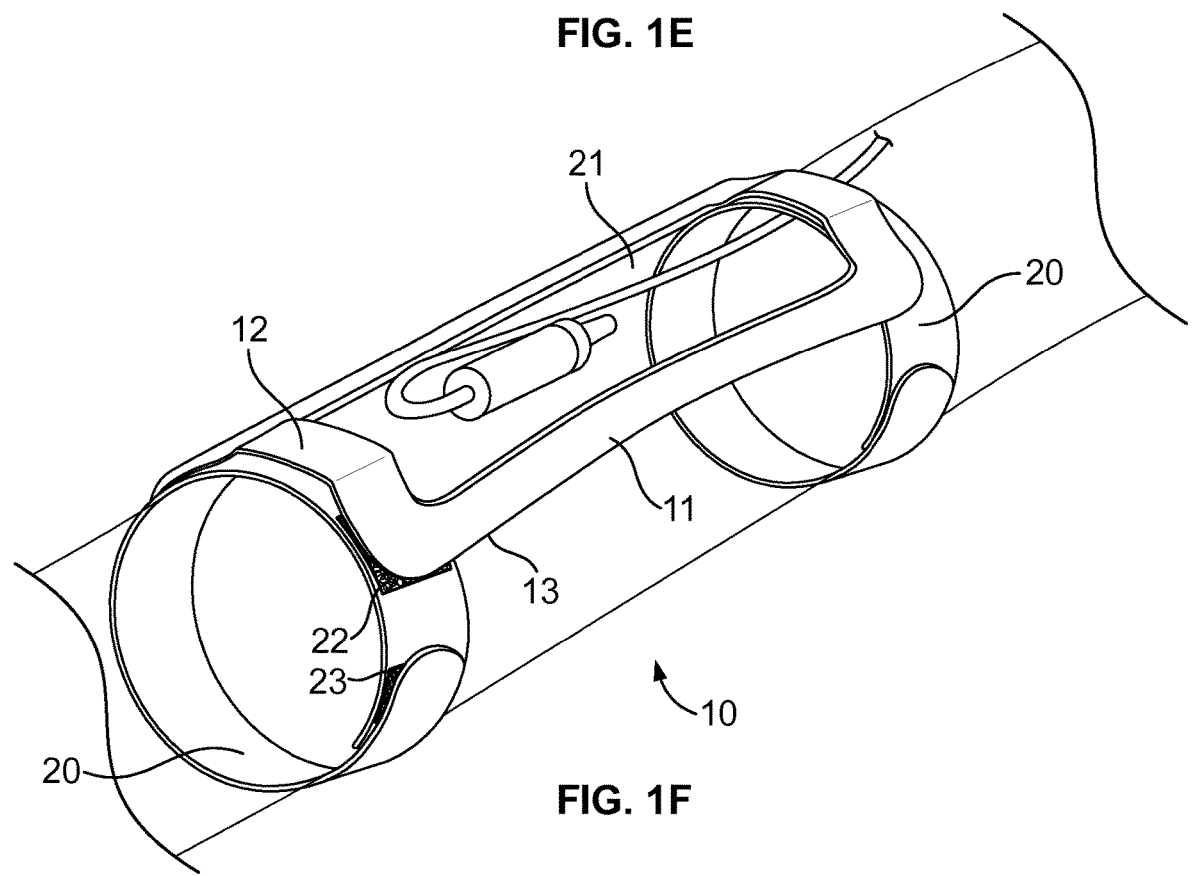
FIG. 1F is a perspective view of the top of the arm support embodiment, where the straps are affixed to the bottom of the stabilizer.

The accompanying drawings illustrate several embodiments of an extremity support. Arm supports 10 and leg supports 30 are exemplified. FIGS. 1A-1F disclose examples of an arm support embodiment 10 comprising a rectangular stabilizer 11 and a rectangular window 21. The stabilizer 11 has an extremity support surface 12, a bottom 19, and sides 13, and the window 21 is an opening through the stabilizer 11. The straps 20 are not permanently affixed to the stabilizer 11, but may be attached to the bottom 19, sides 13, or extremity support surface 12 of the stabilizer 11 with the affixing means 22 and the closure means 23. In the embodiment in FIGS. 1A-1F, hook-and-loop fasteners are used as the means for affixing 22 the straps 20 to the stabilizer 11 and as the means for closing 23 the extremity support 10 around a patient. The straps 20 are made of a stretchable material. FIG. 1D illustrates that a patient's palm 26 and forearm 27 may be viewed through the window 21 without removing the arm support 10.

Figure 2A:
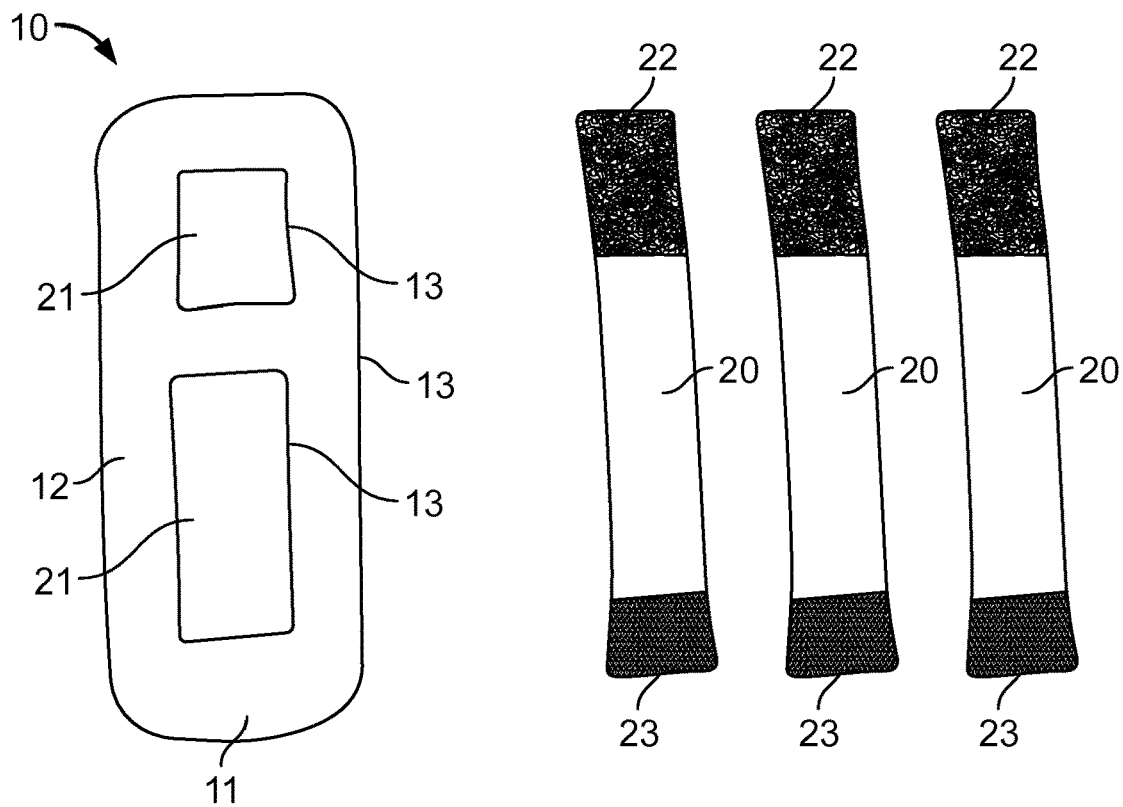
FIG. 2A is a plan view of the top of an arm support embodiment, where the straps are not permanently affixed to the stabilizer.
Figure 2B:
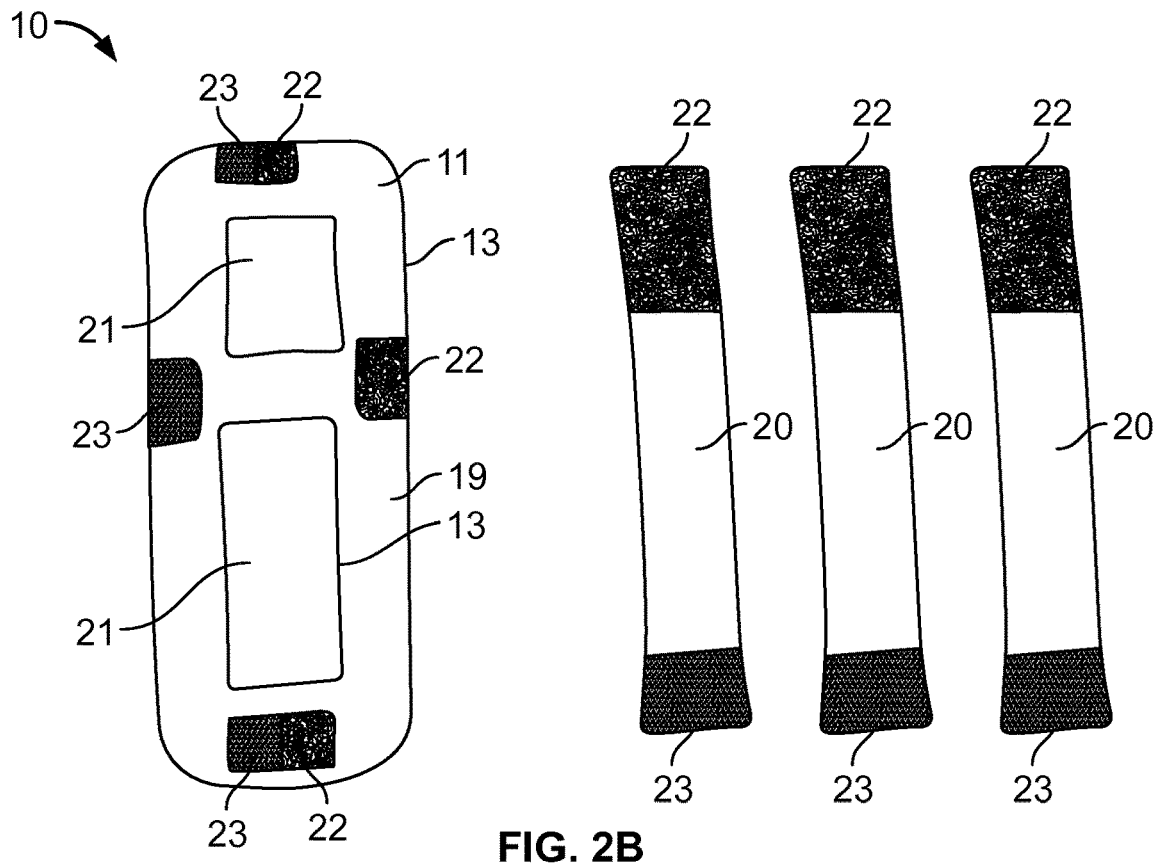
FIG. 2B is a plan view of the bottom of an arm support embodiment, where the straps are not permanently affixed to the stabilizer.
Figure 2C:
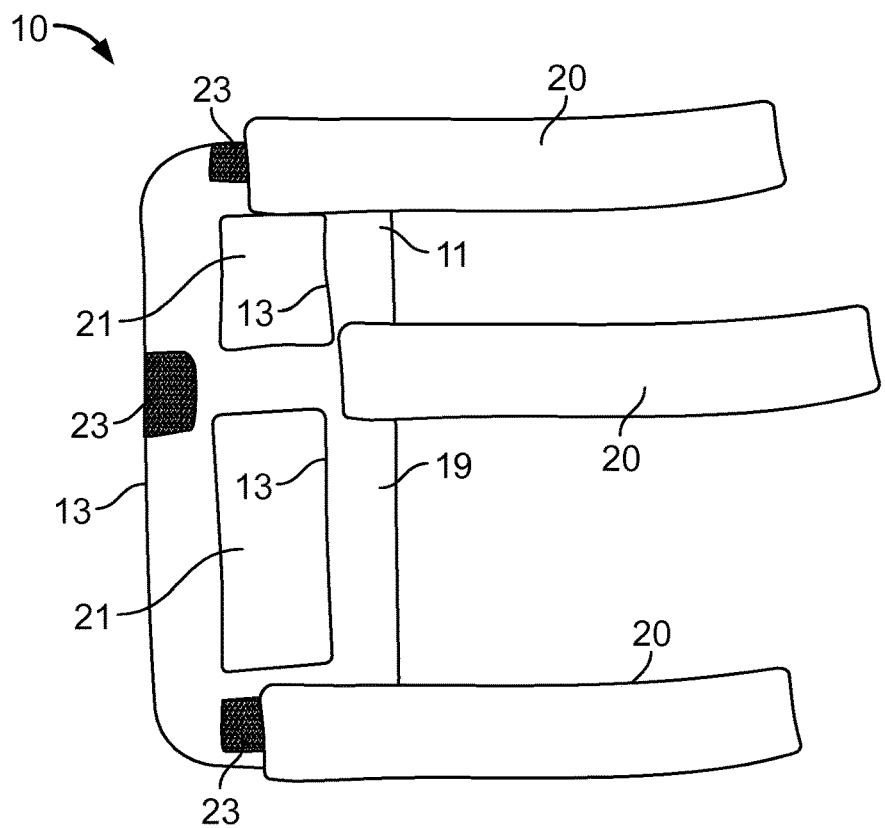
FIG. 2C is a plan view of the bottom of an arm support embodiment, where the straps are affixed to the bottom of the stabilizer.
Figure 2D:
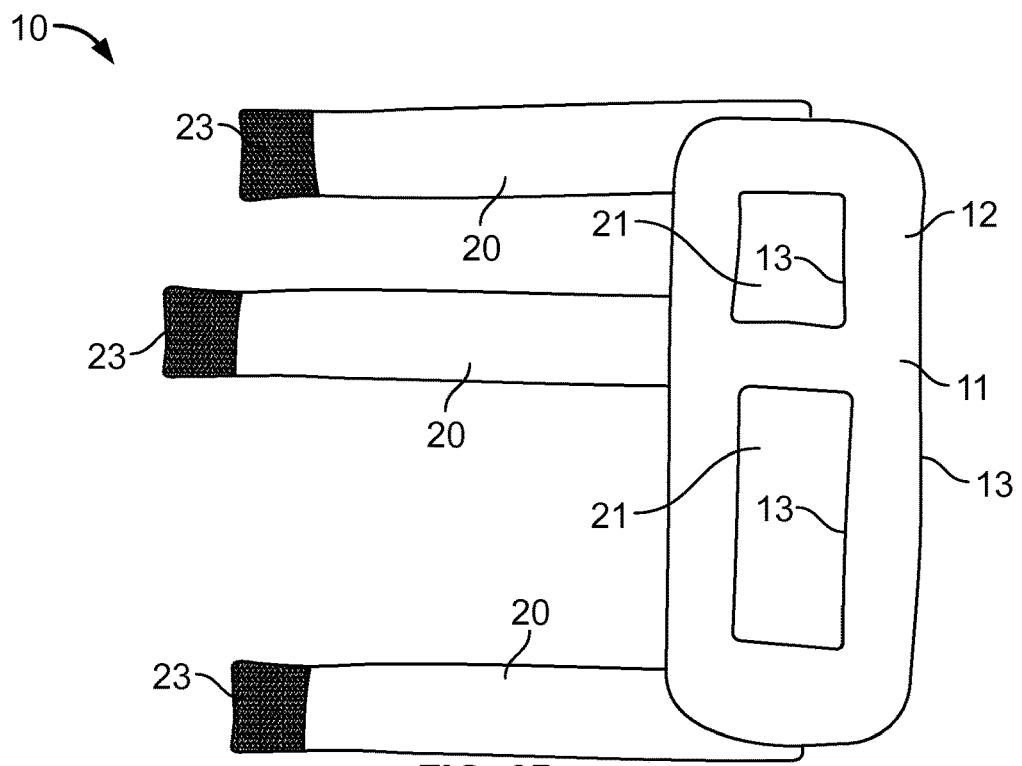
FIG. 2D is a plan view of the top of an arm support embodiment, where the straps are affixed to the bottom of the stabilizer.
Figure 2E:
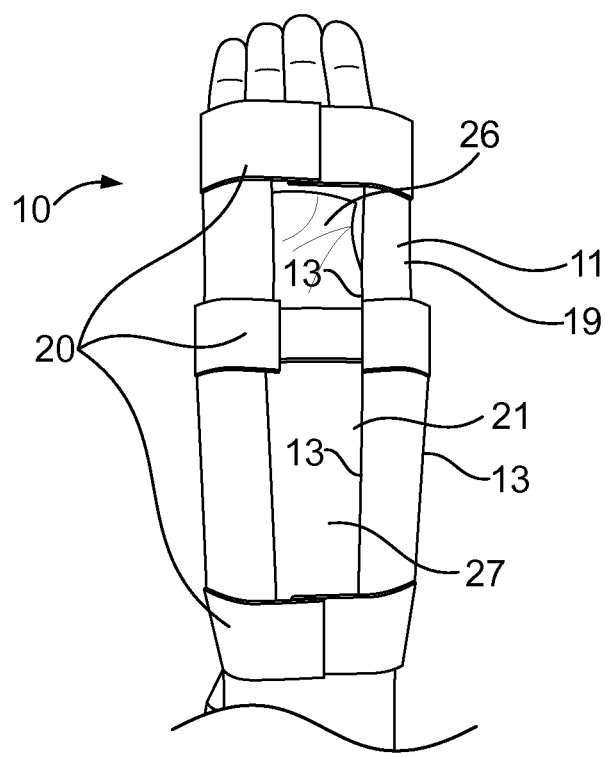
FIG. 2E is a plan view of the bottom of the arm support embodiment as shown in FIGS. 2A-2D, where the arm support is closed around a patient, and where the plan view shows the palm and the forearm through the stabilizer.
Figure 2F:
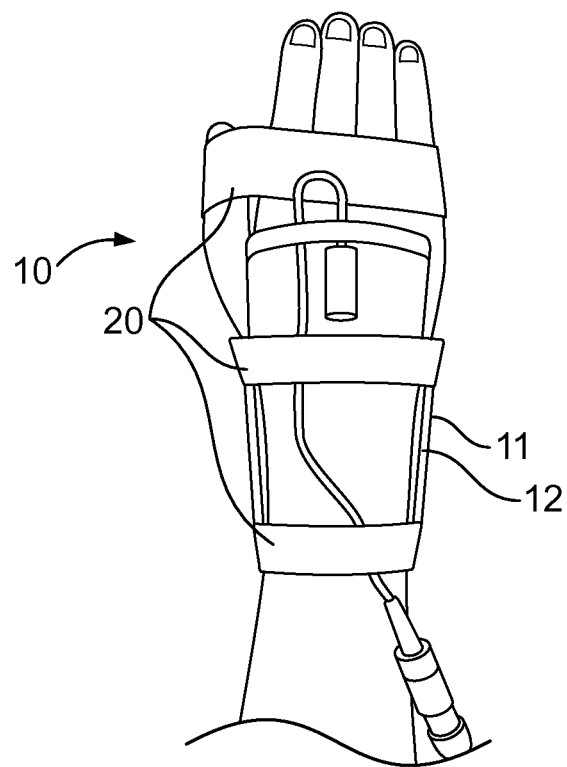
FIG. 2F is a plan view of the top of an arm support embodiment as shown in FIGS. 2A-2D, where the arm support is closed around a patient.
Figure 2G:
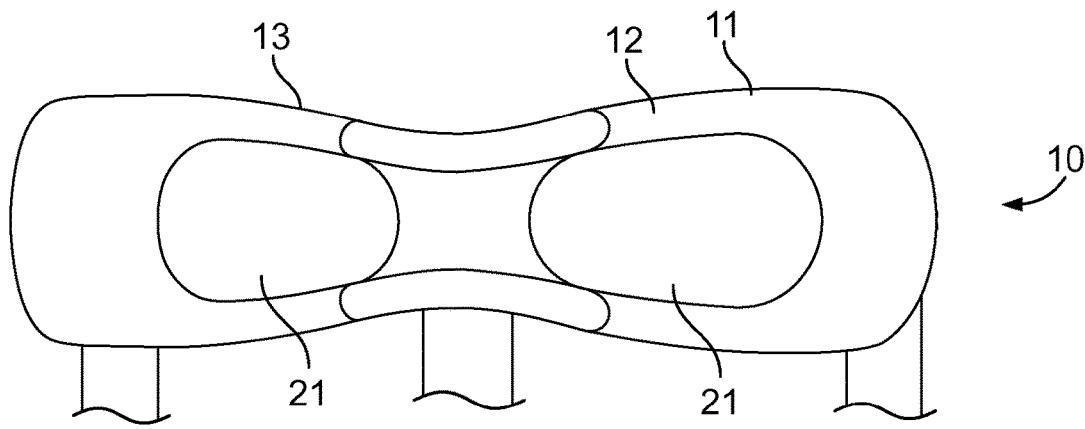
FIG. 2G is a plan view of the top of an arm support embodiment, where the straps are affixed to the stabilizer.
Figure 2H:
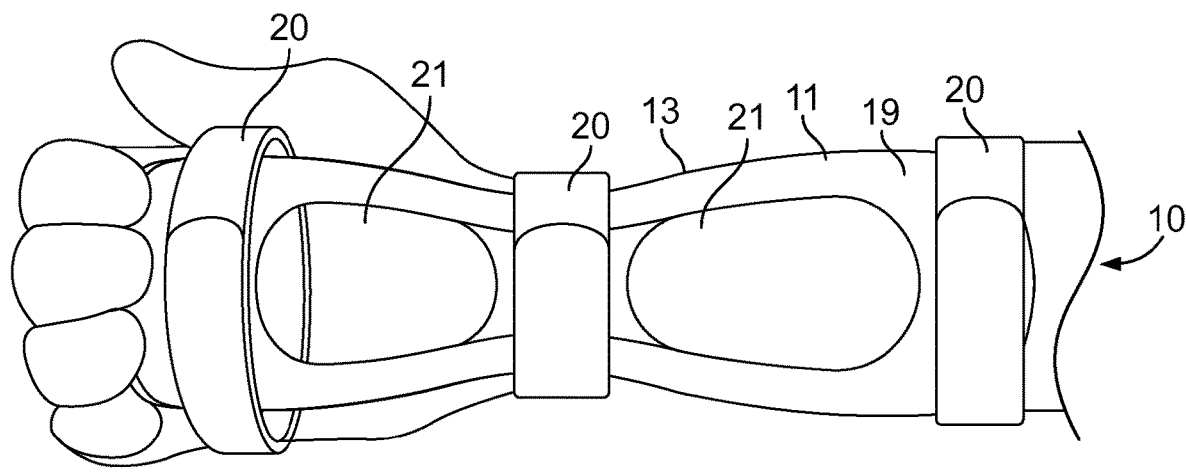
FIG. 2H is a bottom view of an arm support embodiment, where the arm support is closed around a patient.
Figure 2I:
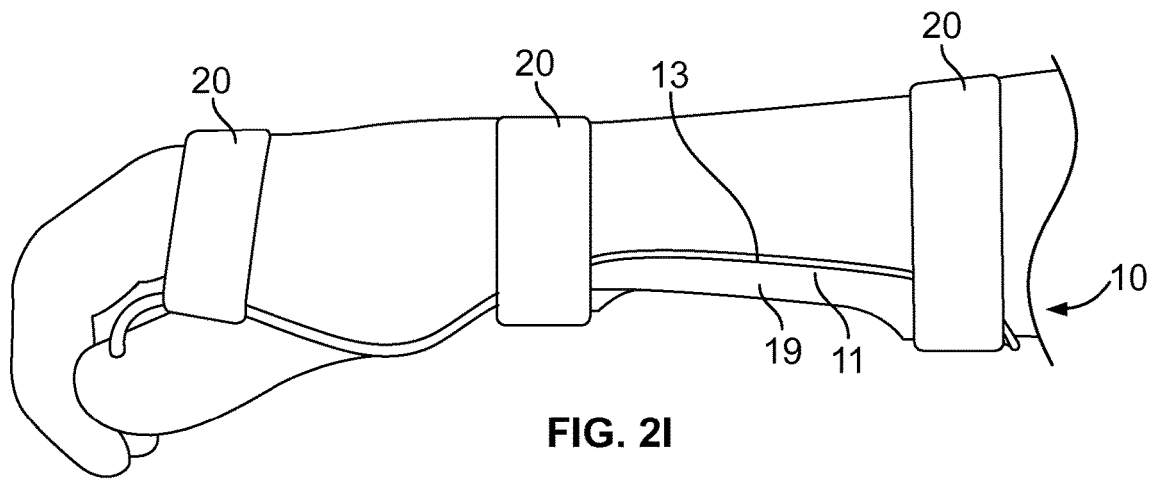
FIG. 2I is a side view of an arm support embodiment, where the arm support is closed around a patient.

FIGS. 2A-2I disclose examples of an arm support embodiment 10, comprising a rectangular stabilizer 11 and two rectangular windows 21. The stabilizer 11 has an extremity support surface 12, a bottom 19, and sides 13, and the two windows 21 are openings through the stabilizer 11. The straps 20 are not permanently affixed to the stabilizer 11, but may be attached to the bottom 19, sides 13, or extremity support surface 12 of the stabilizer 11 with the affixing means 22 and the closure means 23. Hook-and-loop fasteners are used as the means for affixing 22 the straps 20 to the stabilizer 11 and as the means for closing 23 the extremity support 10 around a patient. The straps 20 are made of a stretchable material. FIGS. 2E, and H illustrate that a patient's palm and forearm can be viewed with ease through the window 21 without removing the arm support 10.

Figure 2J:
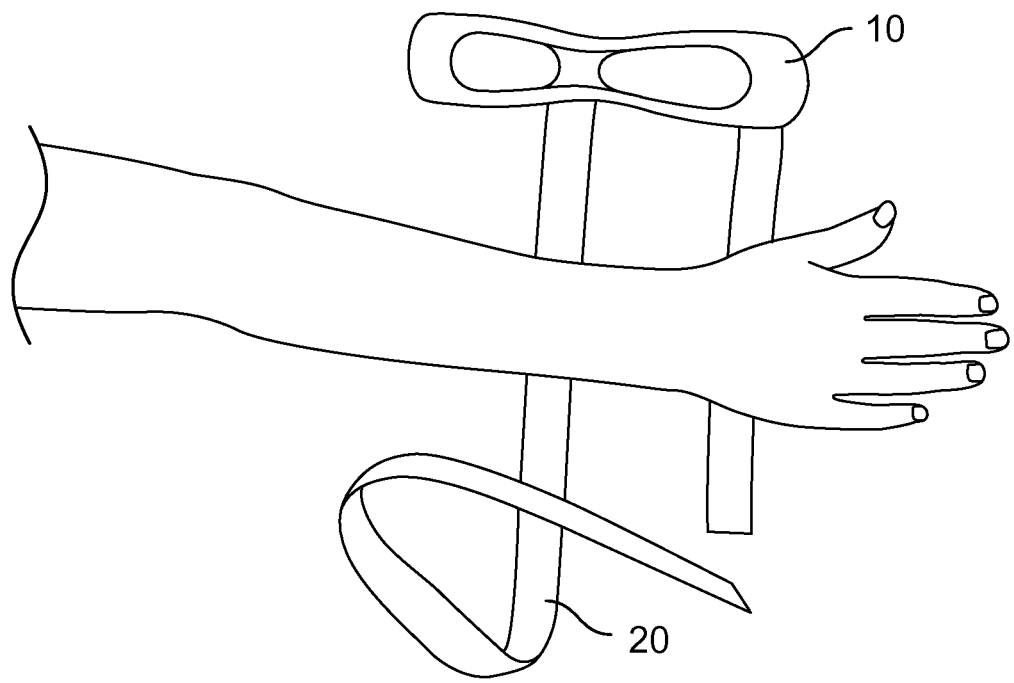
FIG. 2J is a plan view of the top of an arm support embodiment, where the arm support has an extra long strap.
Figure 2K:
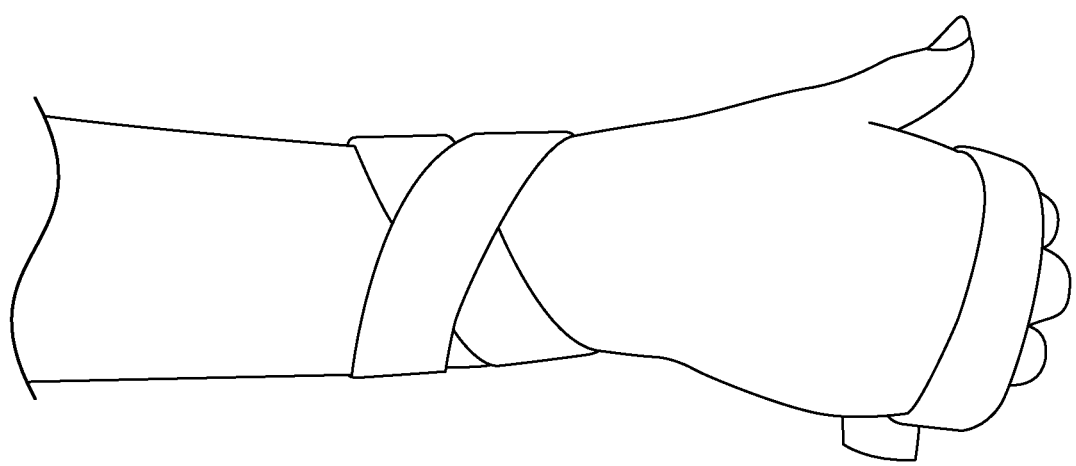
FIG. 2K is a plan view of the top of an arm support embodiment, where the extra long strap is wrapped in a criss-cross fashion around the arm of the patient.
Figure 2L:
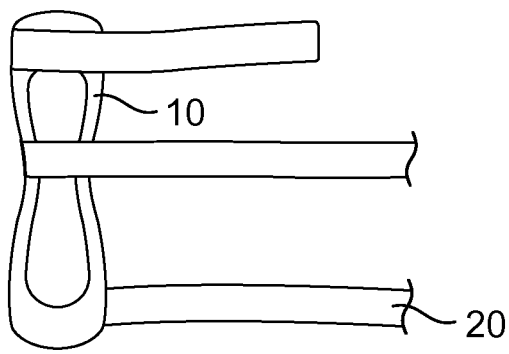
FIG. 2L is a plan view of the bottom of an arm support embodiment, where the straps are attached to the bottom of the stabilizer.
Figure 2M:
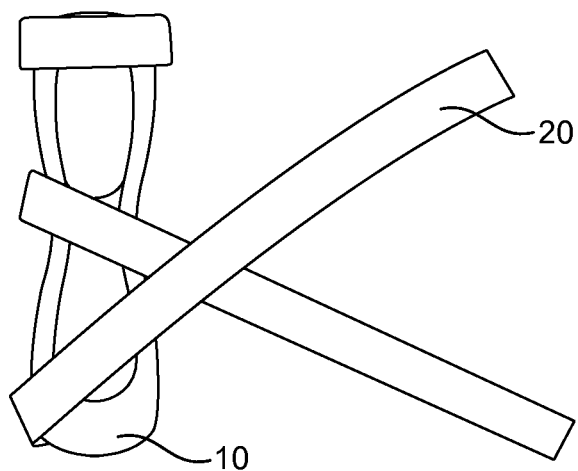
FIG. 2M is a plan view of the top of an arm support embodiment, where the straps are creating an "X" when wrapped around the board.
Figure 2N:
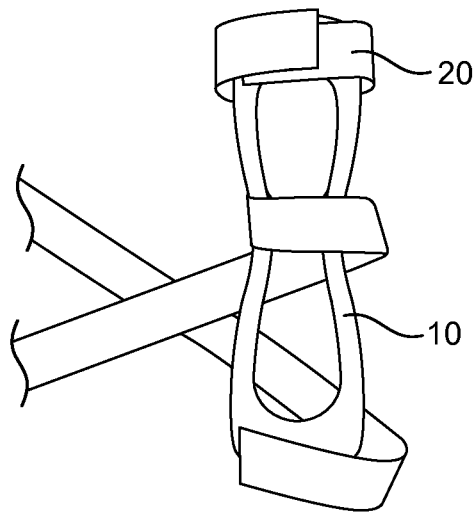
FIG. 2N is a plan view of the bottom of an arm support embodiment, where the straps are creating an "X" when wrapped around the board.
Figure 2O:
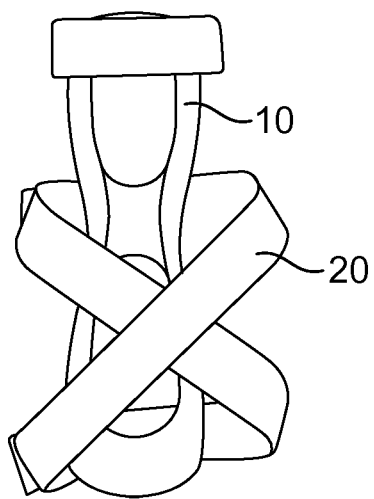
FIG. 2O is a plan view of the top of an arm support embodiment, where the strap ends are secured.
Figure 2P:
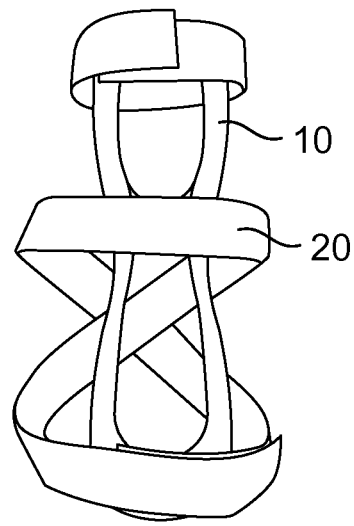
FIG. 2P is a plan view of the bottom of an arm support embodiment, where the strap ends are secured.

FIGS. 2J and 2K disclose an example of an arm support embodiment 10 comprising an extra long strap 20 on the middle of the arm board. The extra long strap 20 will be used to wrap around the arm in a criss-cross fashion and hold the device in place.

FIGS. 2L-2P disclose an example of an arm support embodiment 10 where the straps 20 are secured in an "X" fashion.

Figure 2Q:
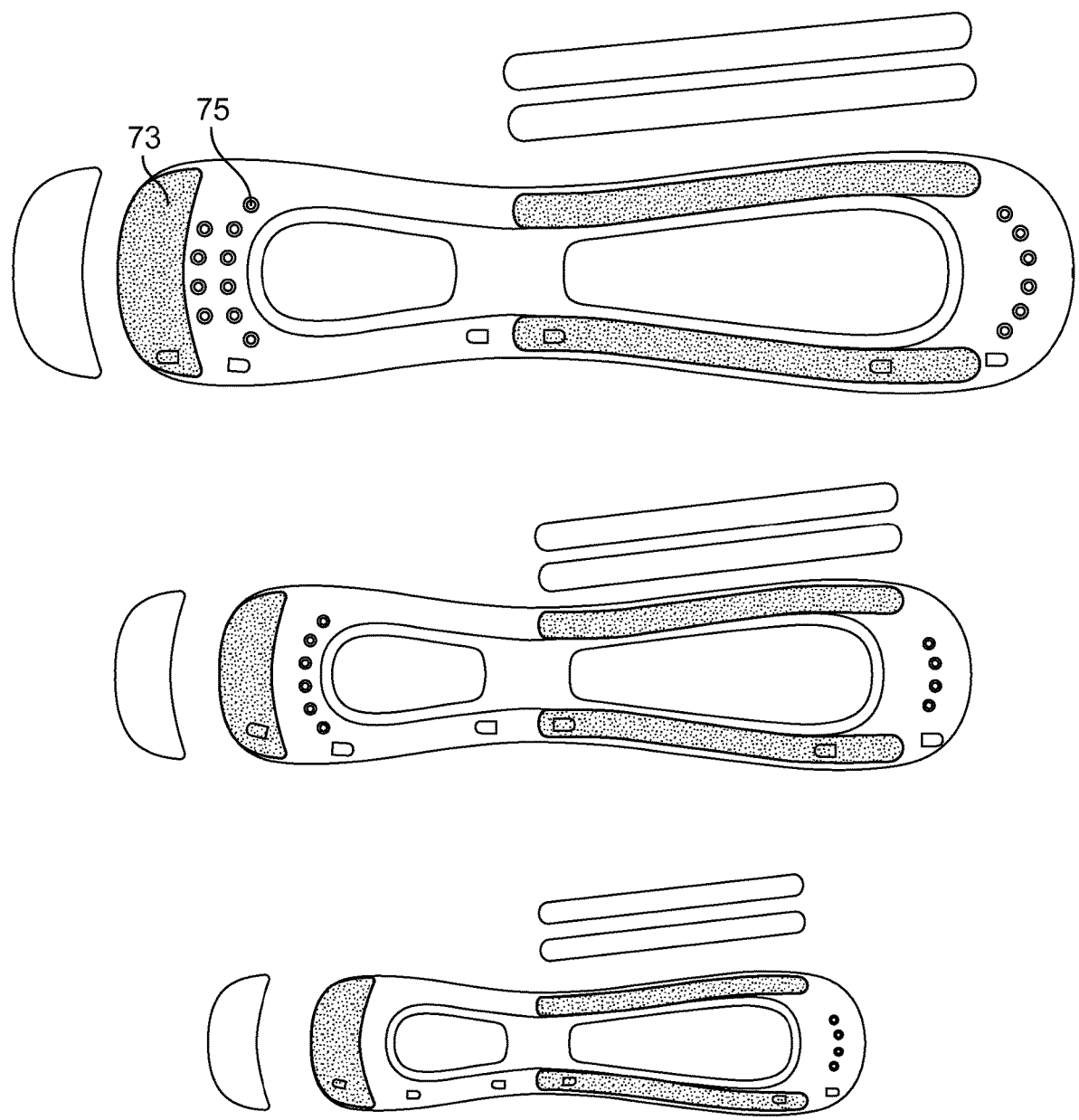
FIG. 2Q is a plan view of the top of an arm support embodiment, where the stabilizer further comprises foam padding.

FIG. 2Q is a plan view of the top of an arm support embodiment, where the stabilizer 11 comprises foam padding 73 and openings 75 for ventilation.

Figure 3A:
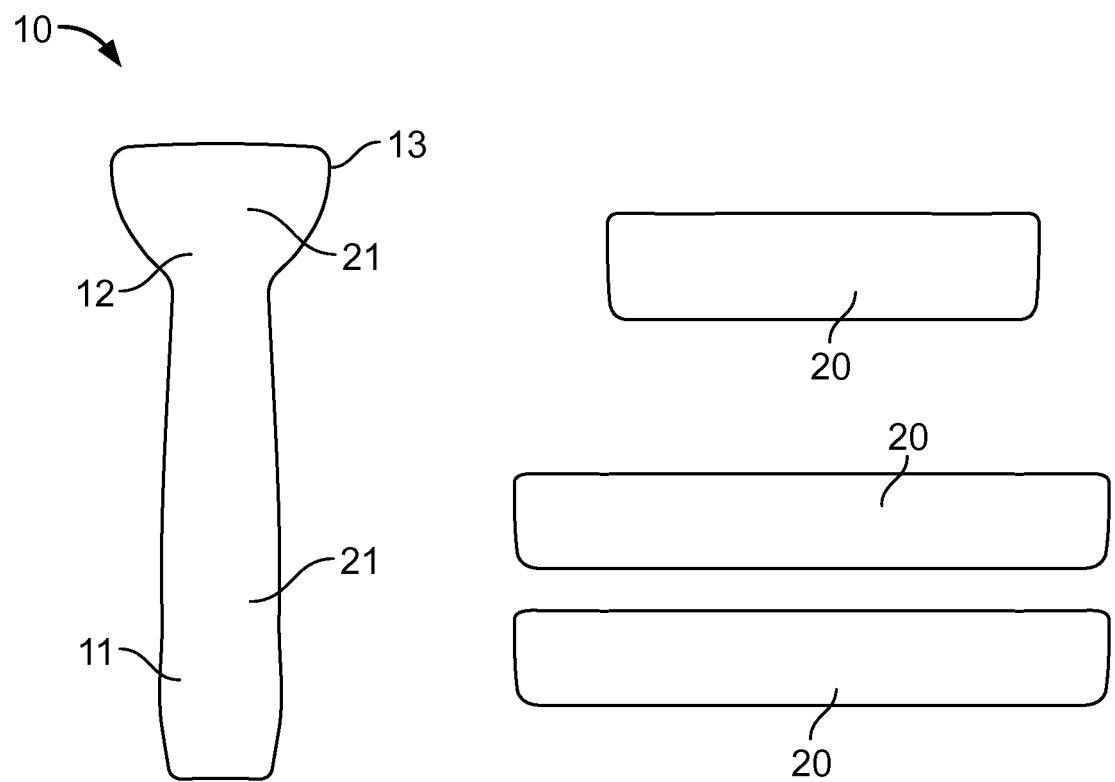
FIG. 3A is a plan view of the top of an arm support embodiment, where the stabilizer is transparent, and where the straps are not permanently affixed to the stabilizer.
Figure 3B:
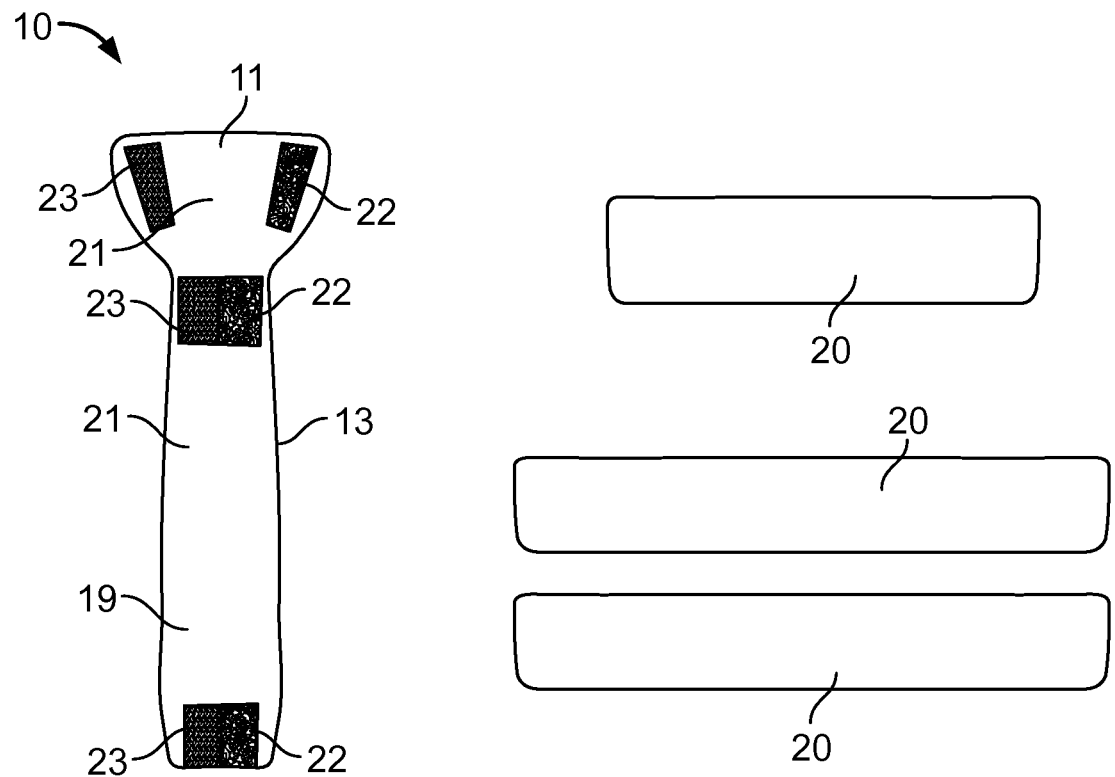
FIG. 3B is a plan view of the bottom of an arm support embodiment, where the stabilizer is transparent, and the straps are not permanently affixed to the stabilizer.
Figure 3C:
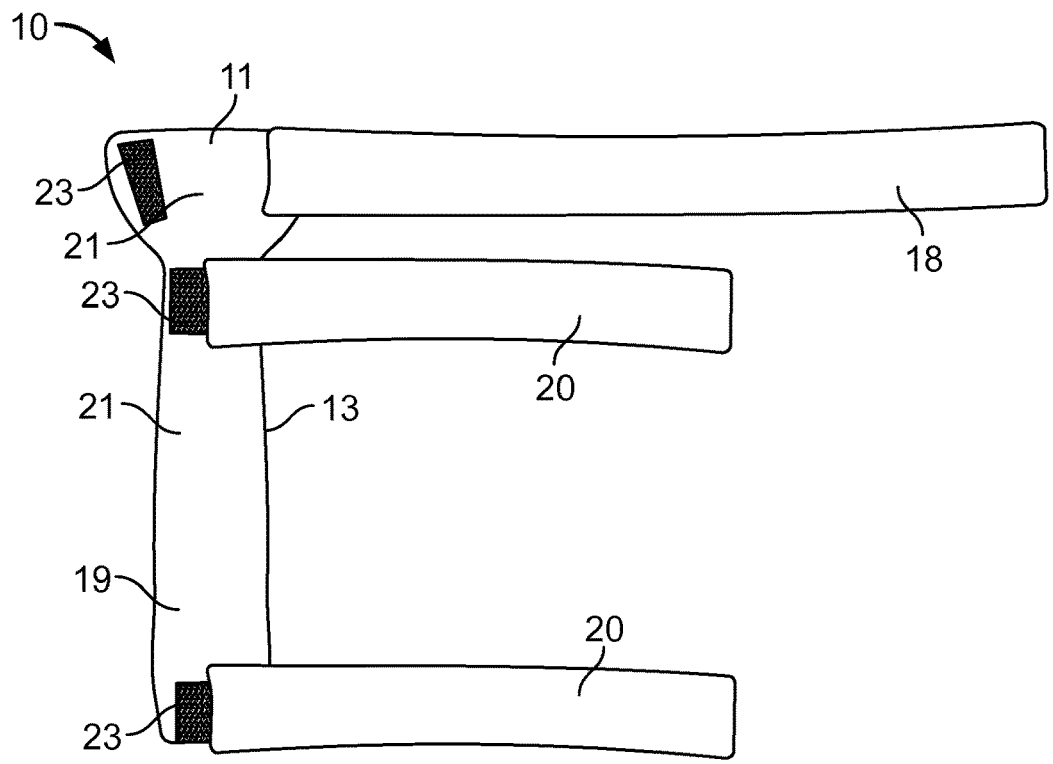
FIG. 3C is a plan view of the bottom of an arm support embodiment, where the entire stabilizer is transparent and the straps are affixed to the bottom of the stabilizer.
Figure 3D:
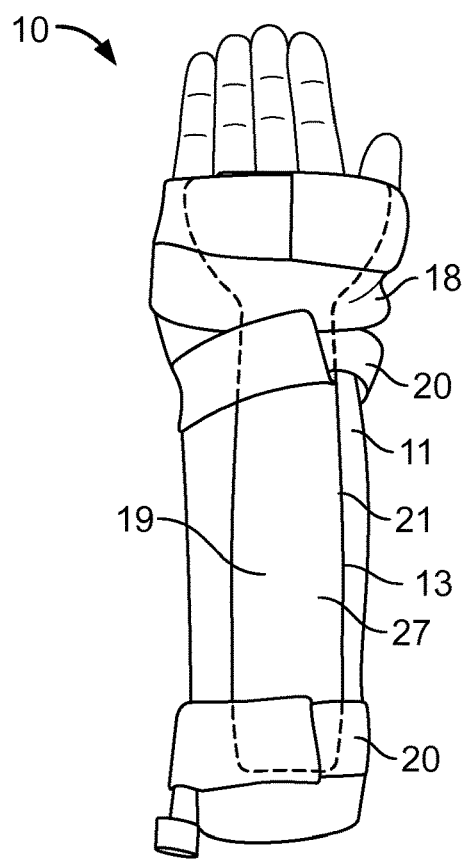
FIG. 3D is a plan view of the bottom of an arm support embodiment as shown in FIGS. 3A-3C, where the arm support is closed around a patient, and where the forearm is visible through the stabilizer.
Figure 3E:
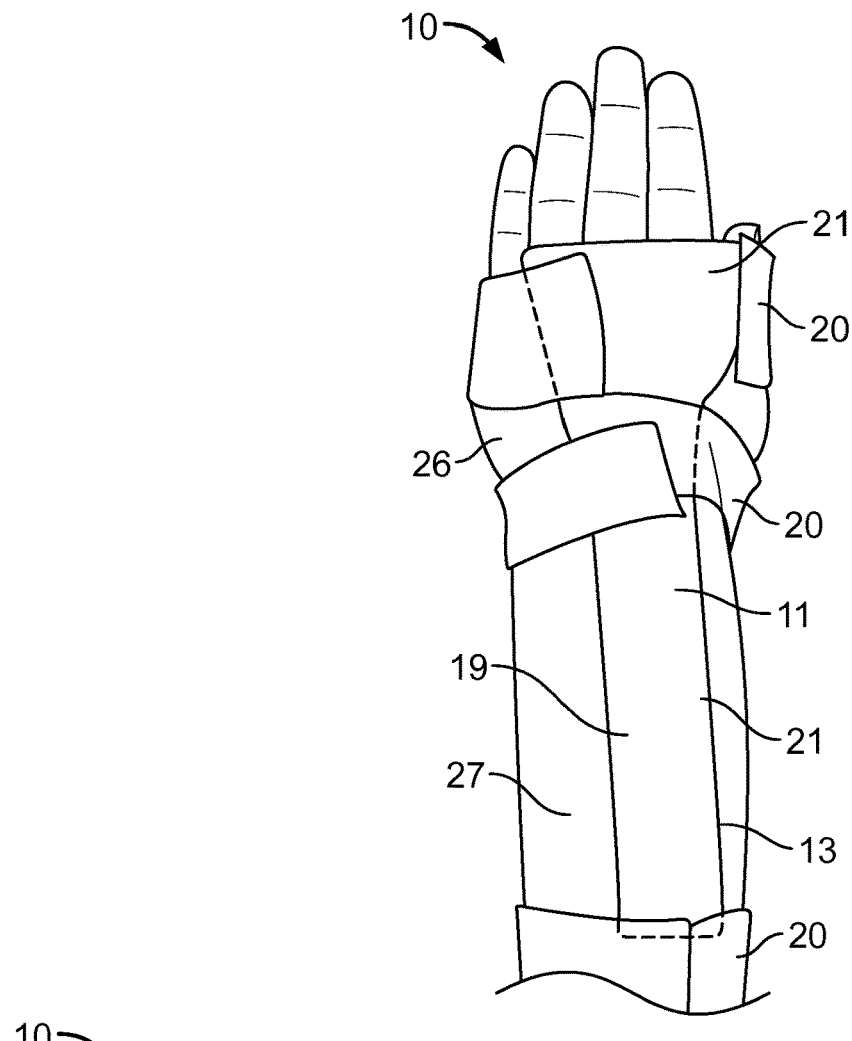
FIG. 3E is a plan view of the bottom of an arm support embodiment as shown in FIGS. 3A-3C, where the arm support is closed around a patient, and where the forearm and the palm are visible through the stabilizer.

FIGS. 3A-3E disclose examples of an arm support embodiment 10 comprising a stabilizer 11 and one window 21. The stabilizer 11 has an extremity support surface 12, a bottom 19, and sides 13, and the window 21 is the transparent stabilizer 11. In other words, the entire stabilizer is also a window as it is transparent. The straps 20 are not permanently affixed to the stabilizer 11, but may be attached to the bottom 19, sides 13, or extremity support surface 12 of the stabilizer 11 with the affixing means 22 and the closure means 23. Hook-and-loop fasteners are used as the means for affixing 22 the straps 20 to the stabilizer 11 and as the means for closing 23 the extremity support 10 around a patient. The straps 20 are made of a stretchable material. FIGS. 3C-3D show an optional long strap 18 that can wrap around the hand more than once. For example, the strap 20 may be wrapped around a patient's forearm at least twice. FIG. 3E shows that a patient's palm 26 and forearm 27 can be viewed with ease through the transparent stabilizer 11 without removing the arm support 10.

Figure 4:
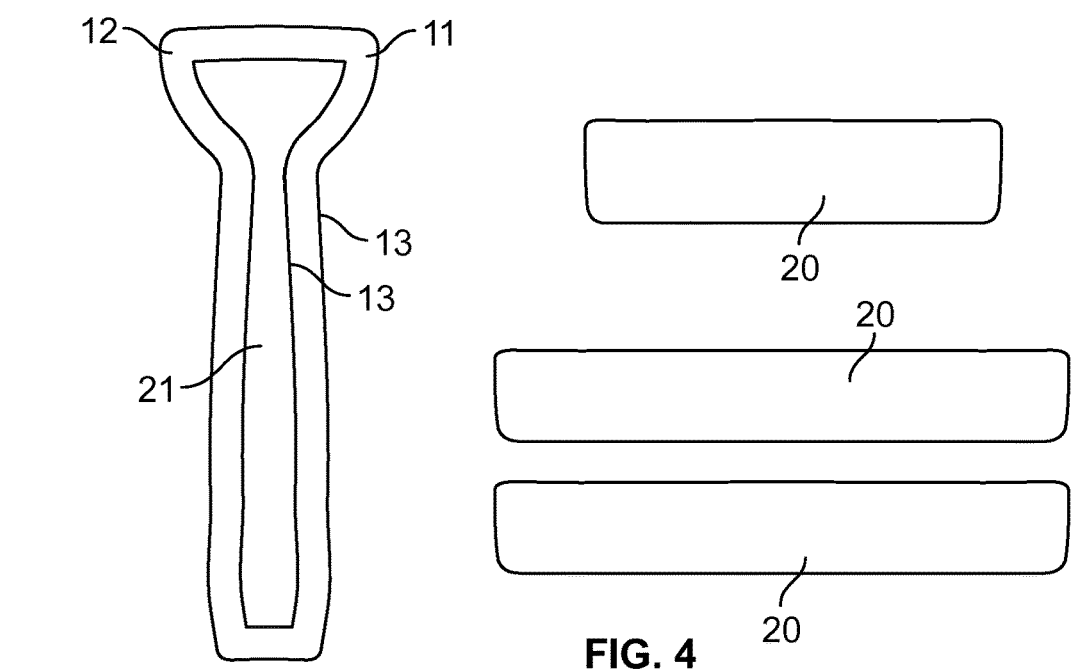
FIG. 4 is a plan view of the top of an arm support embodiment, where the embodiment comprises a hollow center, and where the straps are not permanently affixed to the stabilizer.

FIG. 4 illustrates an arm support embodiment 10 similar to the arm support embodiment 10 in FIGS. 3A-3E. However, in FIG. 4, the window 21 in the embodiment is an opening through the stabilizer, where the window 21 in the embodiment in FIG. 3A is the transparent stabilizer 11.

FIGS. 5A-5E disclose examples of an arm support embodiment 10 comprising a stabilizer 11 shaped like the number eight, and two windows 21. The stabilizer 11 has an extremity support surface 12, a bottom 19, and sides 13, and the windows 21 are openings in the stabilizer 11. One window 21 is oval-shaped, and the other window 21 is round. However, both windows 21 could be oval-shaped, or both windows 21 could be round. The window 21 can take on other shapes as well. The sides 13 may be bent to support the side of the arm so that the support surface is actually resting on the back of the hand and forearm and bent to wrap around the side of the hand and forearm, cradling both the hand and forearm.

Figure 5A:
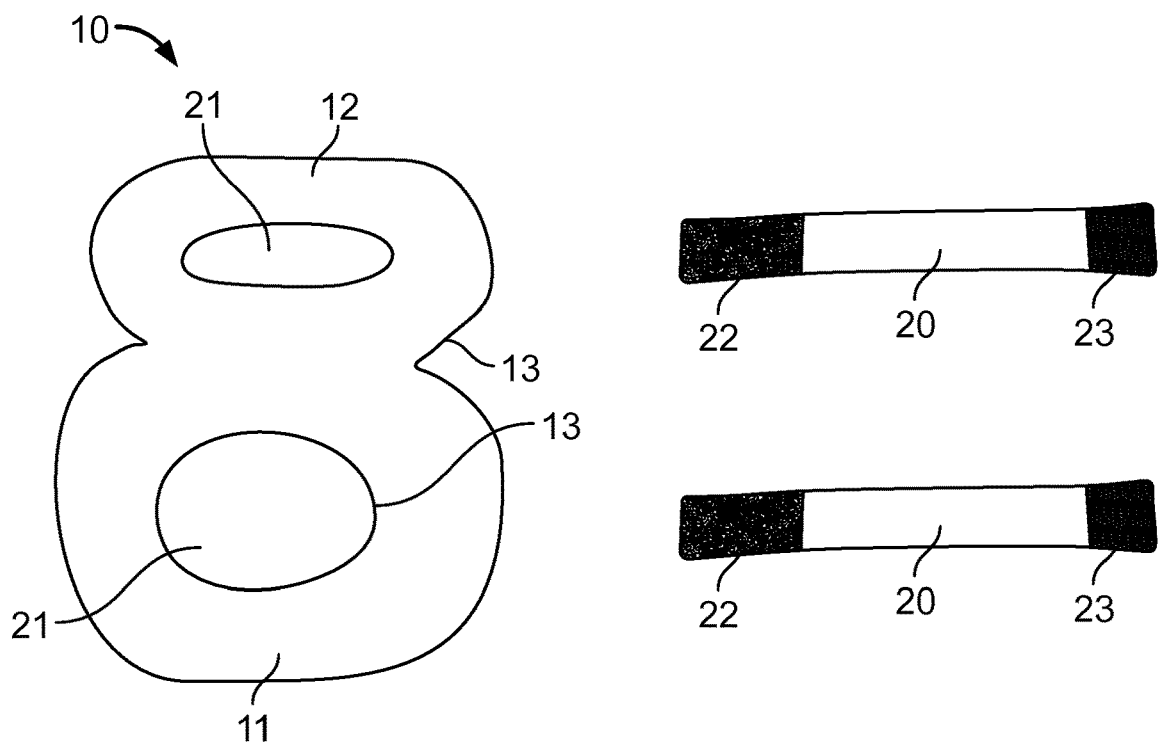
FIG. 5A is a plan view of the top of an arm support embodiment, where the straps are not permanently affixed to the stabilizer.
Figure 5B:
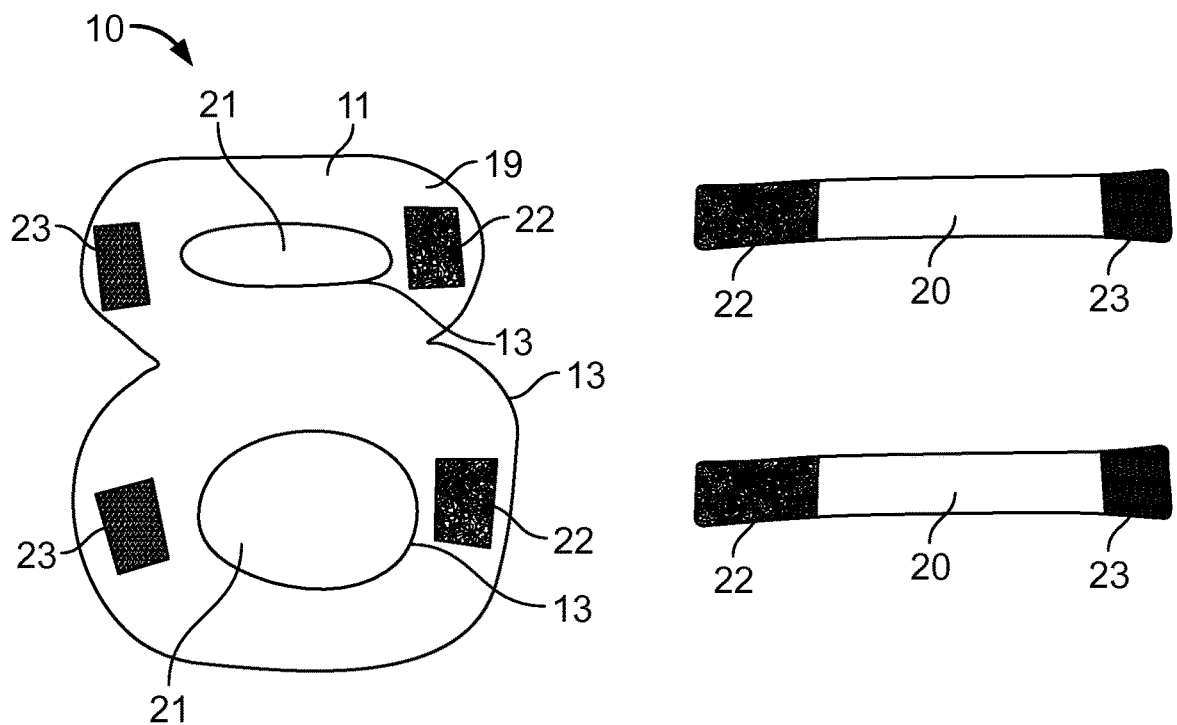
FIG. 5B is a plan view of the bottom of an arm support embodiment, where the straps are not permanently affixed to the stabilizer.
Figure 5C:
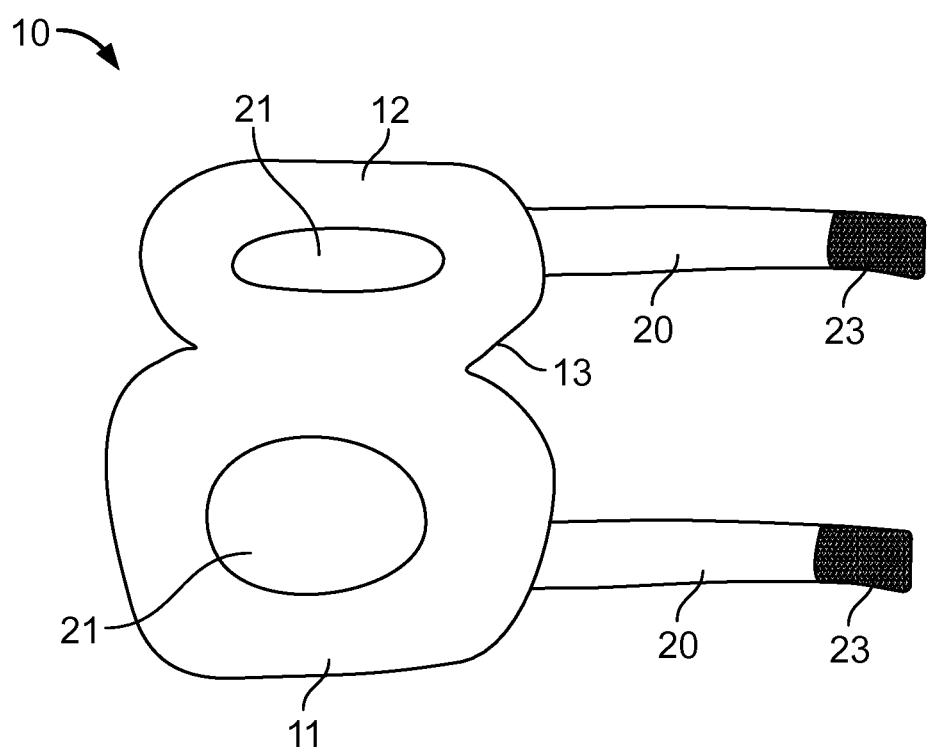
FIG. 5C is a plan view of the top of an arm support embodiment, where the straps are affixed to the bottom of the stabilizer.
Figure 5D:
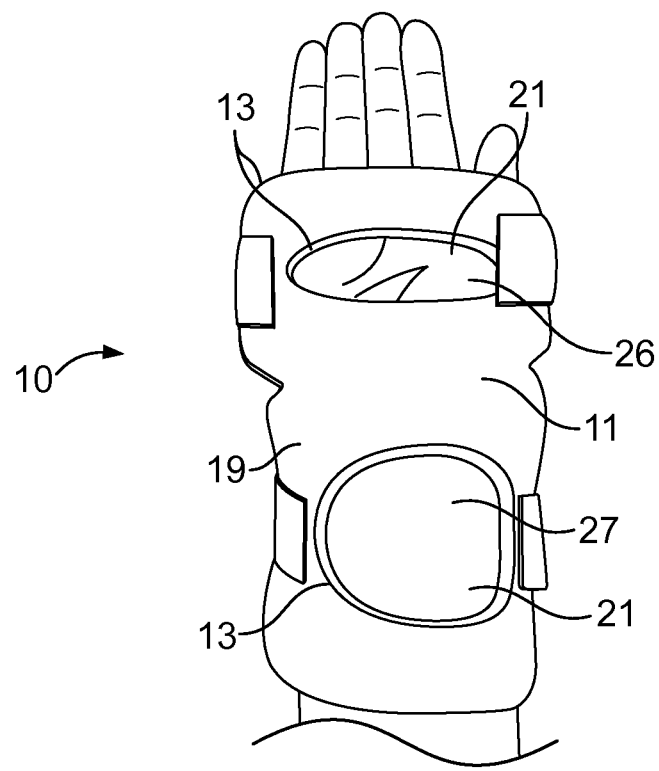
FIG. 5D is a plan view of the bottom of an arm support embodiment as shown in FIGS. 5A-5C, where the arm support is closed around a patient, and where the forearm and the palm are visible through the stabilizer.
Figure 5E:
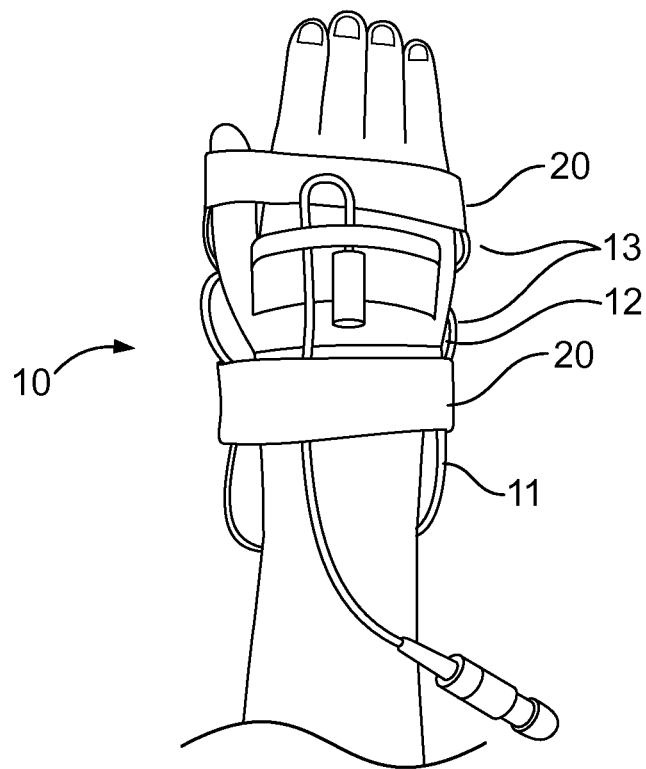
FIG. 5E is a plan view of the top of an arm support embodiment as shown in FIGS. 5A-5C, where the arm support is closed around a patient.

The two straps 20 are not permanently affixed to the stabilizer 11, but may be attached to the bottom 19, sides 13, or extremity support surface 12 of the stabilizer 11 with the affixing means 22 and the closure means 23. More than two straps may be used with this arm support. Hook-and-loop fasteners are used as the means for affixing 22 the straps 20 to the stabilizer 11 and as the means for closing 23 the extremity support 10 around a patient. The straps 20 are made of a stretchable material. FIG. 5D shows that a patient's palm 26 and forearm 27 can be viewed with ease through the windows 21 without removing the arm support 10. FIG. 5E shows the arm support embodiment 10 bending to cradle the hand and forearm.

Figure 6A:
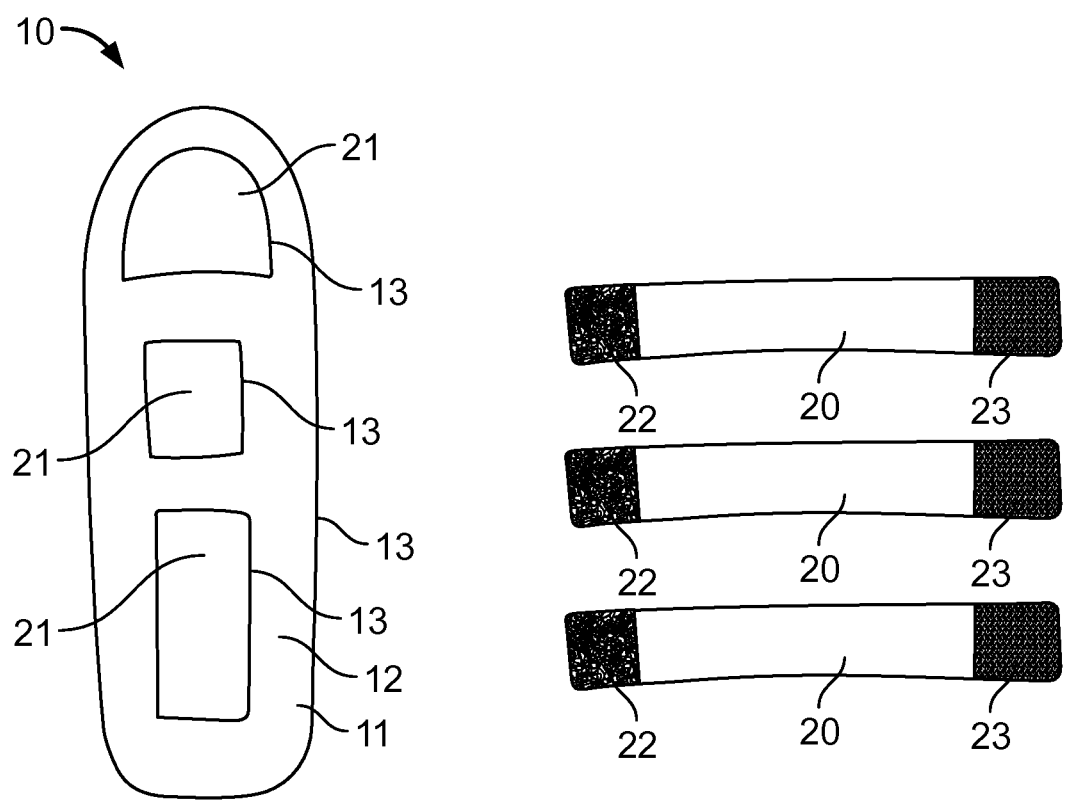
FIG. 6A is a plan view of the top of an arm support embodiment, where the straps are not permanently affixed to the stabilizer.
Figure 6B:
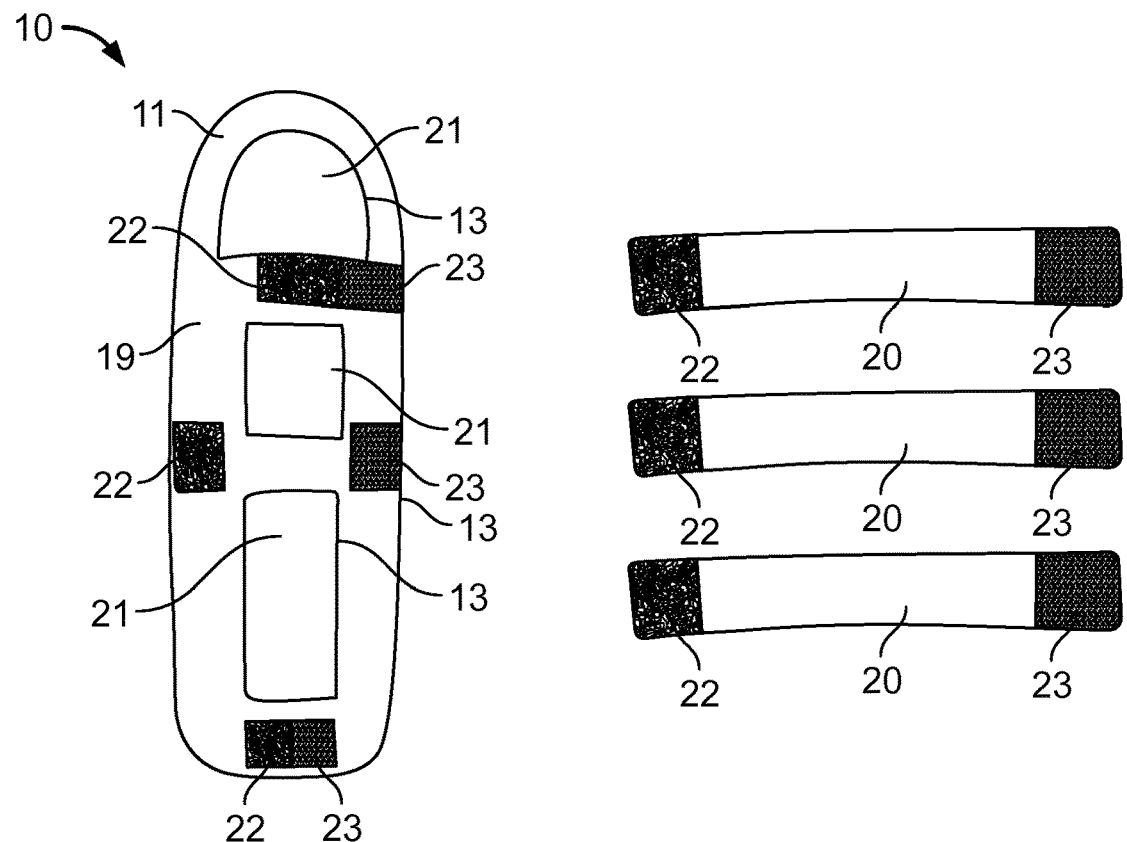
FIG. 6B is a plan view of the bottom of an arm support embodiment, where the straps are not permanently affixed to the stabilizer.
Figure 6C:
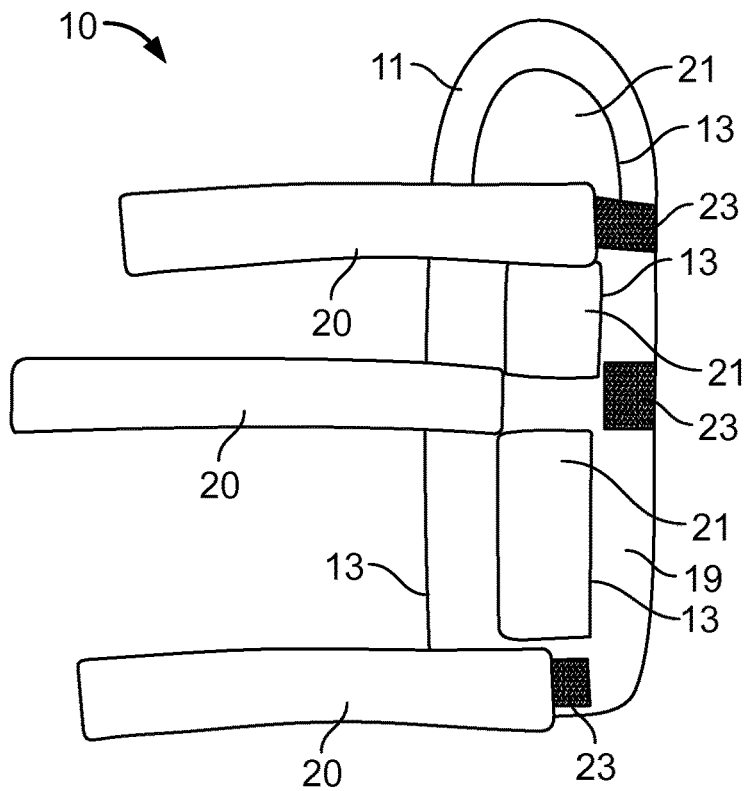
FIG. 6C is a plan view of the bottom of an arm support embodiment, where the straps are affixed to the bottom of the stabilizer.
Figure 6D:
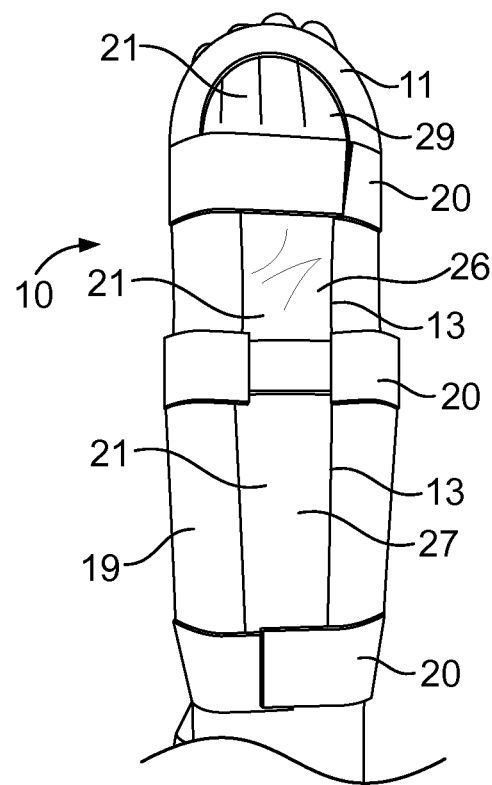
FIG. 6D is a plan view of the bottom of an arm support embodiment as shown in FIGS. 6A-6C, where the arm support is closed around a patient, and where the forearm and the palm are visible through the windows.
Figure 6E:
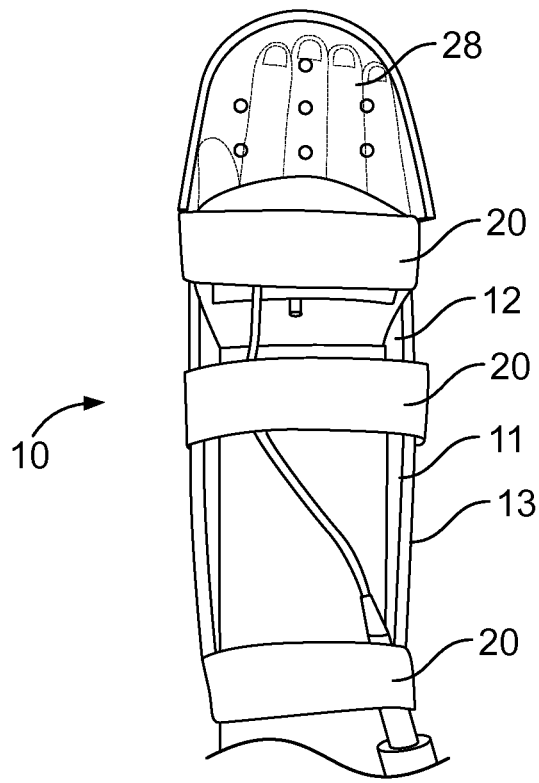
FIG. 6E is a plan view of the top of an arm support embodiment as shown in FIGS. 6A-6C, where the arm support is closed around a patient, and where the arm support is used with an I.V. site guard (e.g., I.V. House UltraDome®).

FIGS. 6A-6E disclose examples of an arm support embodiment 10, comprising a silo-shaped stabilizer 11 and three windows 21. The stabilizer 11 has an extremity support surface 12, a bottom 19, and sides 13, and the three windows 21 are openings in the stabilizer 11. Two windows 21 are rectangular, and one window 21 is shaped like a half circle. The three straps 20 are not permanently affixed to the stabilizer 11, but may be attached to the bottom 19, sides 13, or extremity support surface 12 of the stabilizer 11 with the affixing means 22 and the closure means 23. Hook-and-loop fasteners are used as the means for affixing 22 the straps 20 to the stabilizer 11 and as the means for closing 23 the extremity support 10 around a patient. The straps 20 are made of a stretchable material. FIG. 6D shows that a patient's fingers 29, palm 26, and forearm 27 can be viewed with ease through the windows 21 without removing the arm support 10. FIG. 6E illustrates the use of an I.V. House UltraDome® 28 with the arm support embodiment 10. In one embodiment, a patient's fingers can rest above or below the U-shaped top of the stabilizer. In still another embodiment, an IV site guard 28, such as a site guard sold under the trade name I.V. House UltraDome® or I.V. House Ultra-Dressing® can rest on the U-shaped top of the stabilizer.

Figure 7A:
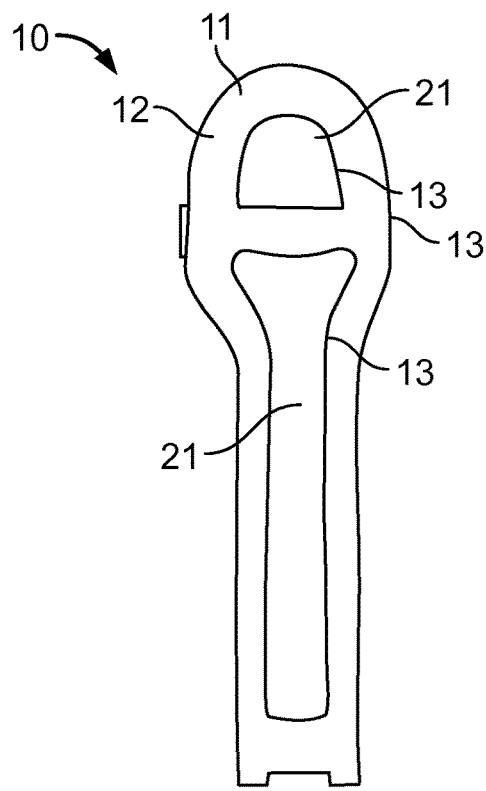
FIG. 7A is a plan view of the top of an arm support embodiment, where the straps are not permanently affixed to the stabilizer.
Figure 7A:
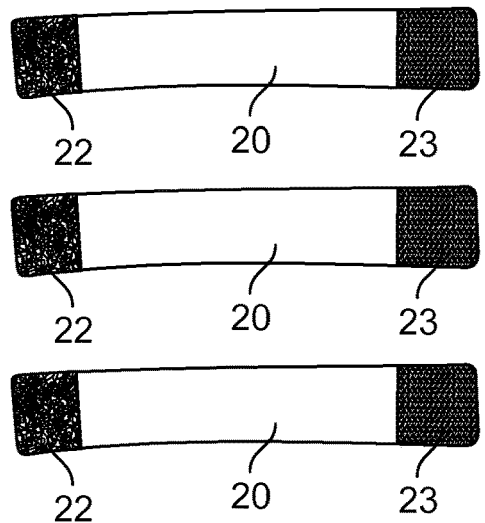
Figure 7B:
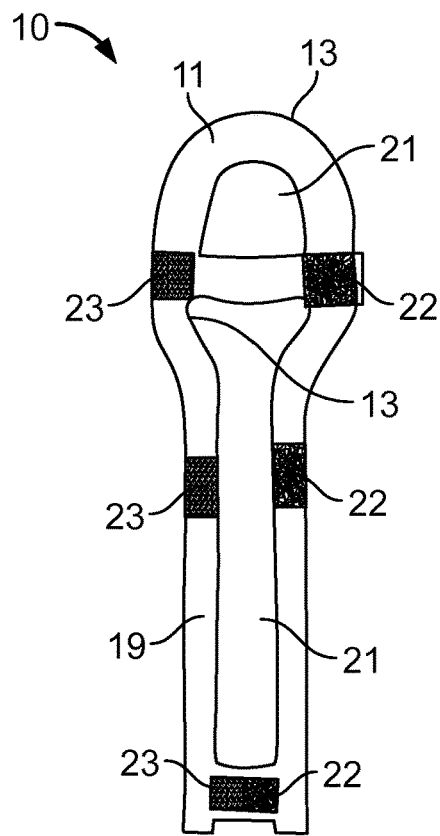
FIG. 7B is a plan view of the bottom of an arm support embodiment, where the straps are not permanently affixed to the stabilizer.
Figure 7B:
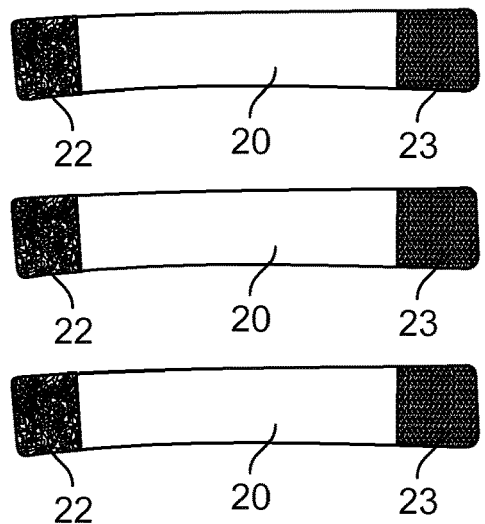
Figure 7C:
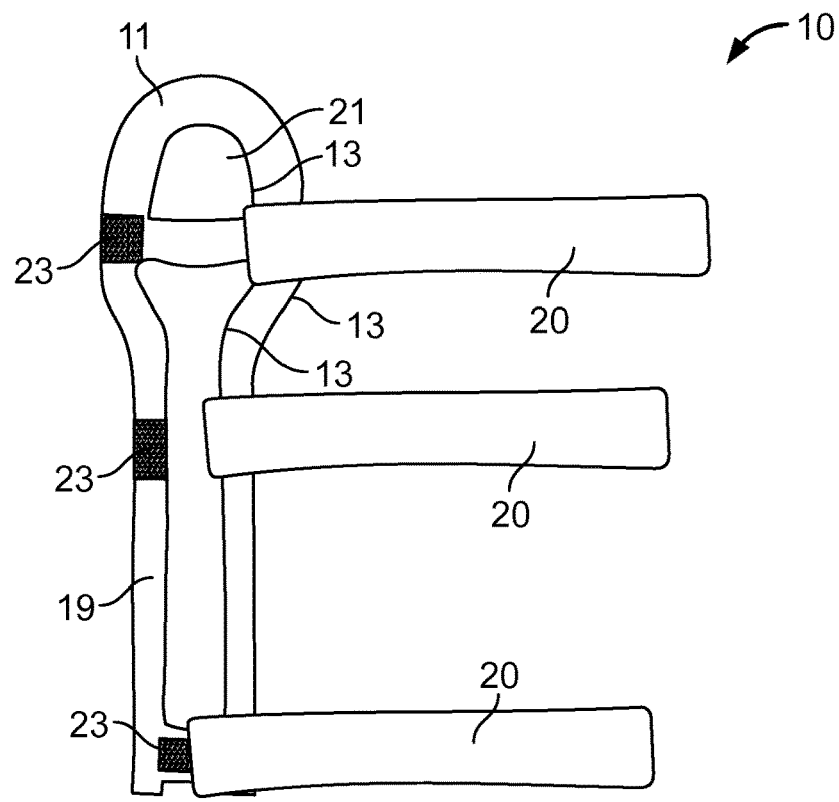
FIG. 7C is a plan view of the bottom of an arm support embodiment, where the straps are affixed to the bottom of the stabilizer.
Figure 7D:
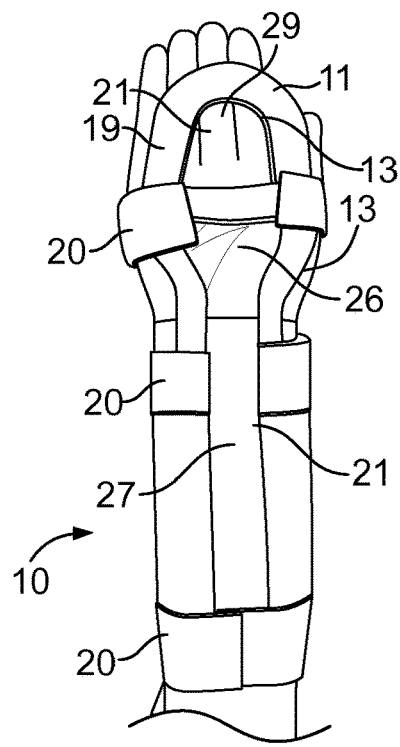
FIG. 7D is a plan view of the bottom of an arm support embodiment as shown in FIGS. 7A-7C, where the arm support is closed around a patient, and where the forearm and the palm are visible through the stabilizer.
Figure 7E:
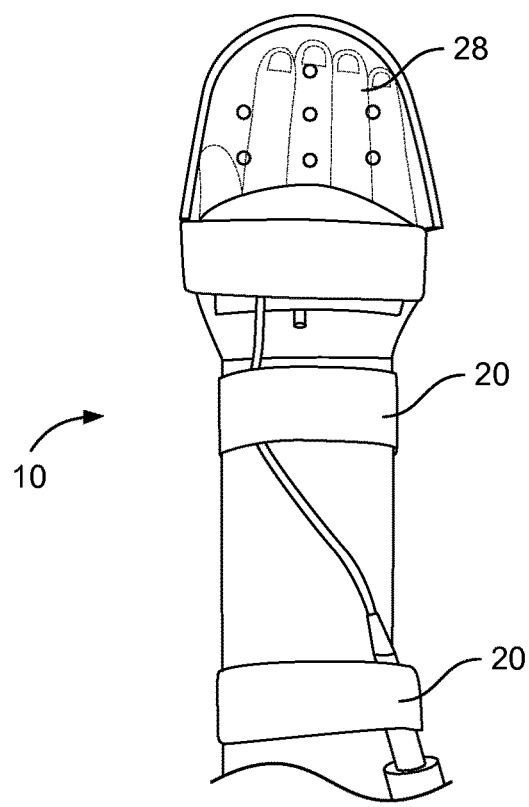
FIG. 7E is a plan view of the top of an arm support embodiment as shown in FIGS. 7A-7C, where the arm support is closed around a patient, and where the arm support is used with an IV site guard (e.g., I.V. House UltraDome®).

FIGS. 7A-7E disclose examples of an arm support embodiment 10 comprising a spoon-shaped stabilizer 11 and two windows 21. The stabilizer 11 has an extremity support surface 12, a bottom 19, and sides 13, and the two windows 21 are openings in the stabilizer 11. The three straps 20 are not permanently affixed to the stabilizer 11, but may be attached to the bottom 19, sides 13, or extremity support surface 12 of the stabilizer 11 with the affixing means 22 and the closure means 23. Hook-and-loop fasteners are used as the means for affixing 22 the straps 20 to the stabilizer 11 and as the means for closing 23 the extremity support 10 around a patient. The straps 20 are made of a stretchable material. FIG. 7D shows that a patient's fingers 29, palm 26, and forearm 27 can be viewed with ease through the windows 21 without removing the arm support 10. FIG. 7E illustrates the use of an I.V. House UltraDome® 28 with the arm support embodiment 10. In one embodiment, a patient's fingers can rest above or below the U-shaped top of the stabilizer. In still another embodiment, an IV site guard 28, such as a site guards sold under the trade name I.V. House UltraDome® or I.V. House UltraDressing® can rest on the U-shaped top of stabilizer.

Figure 8A:
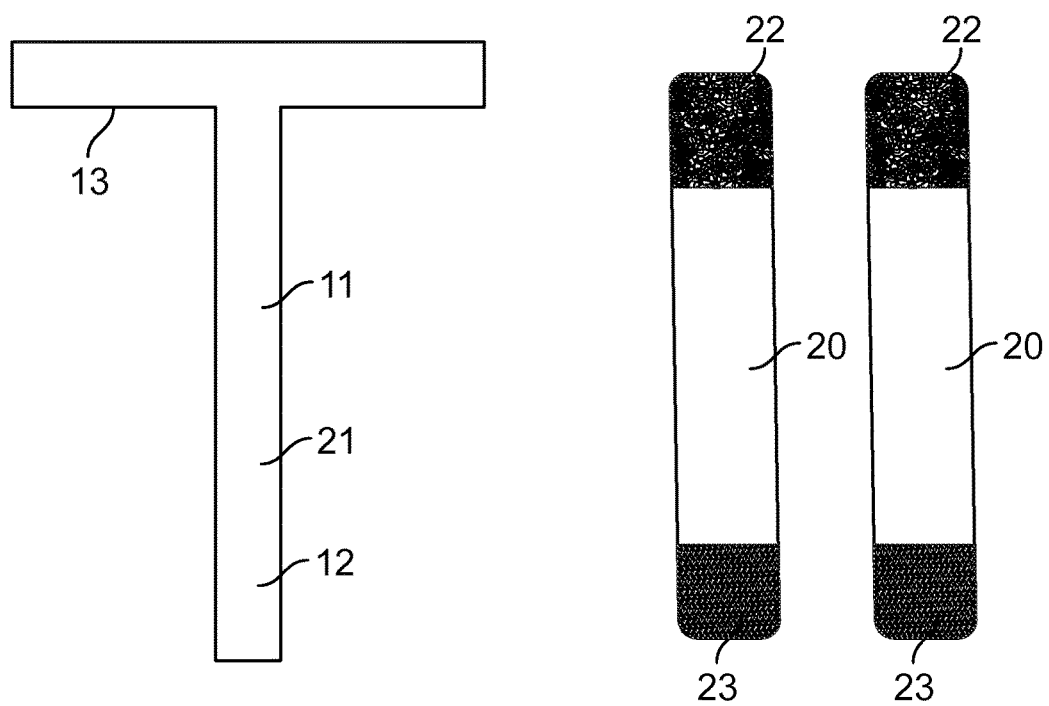
FIG. 8A is a plan view of the top of an arm support embodiment, where the straps are not permanently affixed to the stabilizer.
Figure 8B:
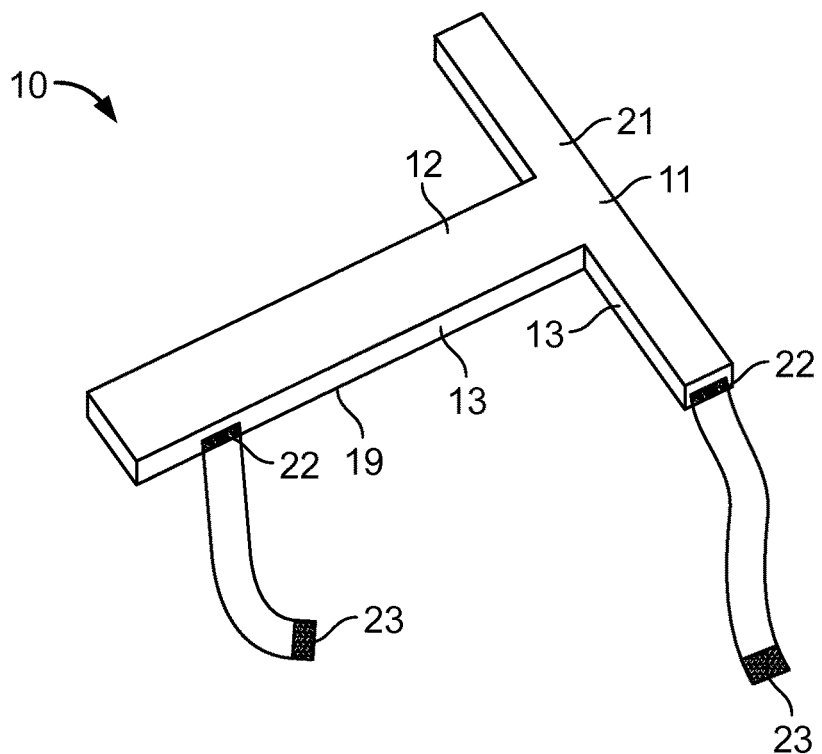
FIG. 8B is a perspective view of an arm support embodiment, where the straps are affixed to the side of the stabilizer.
Figure 8C:
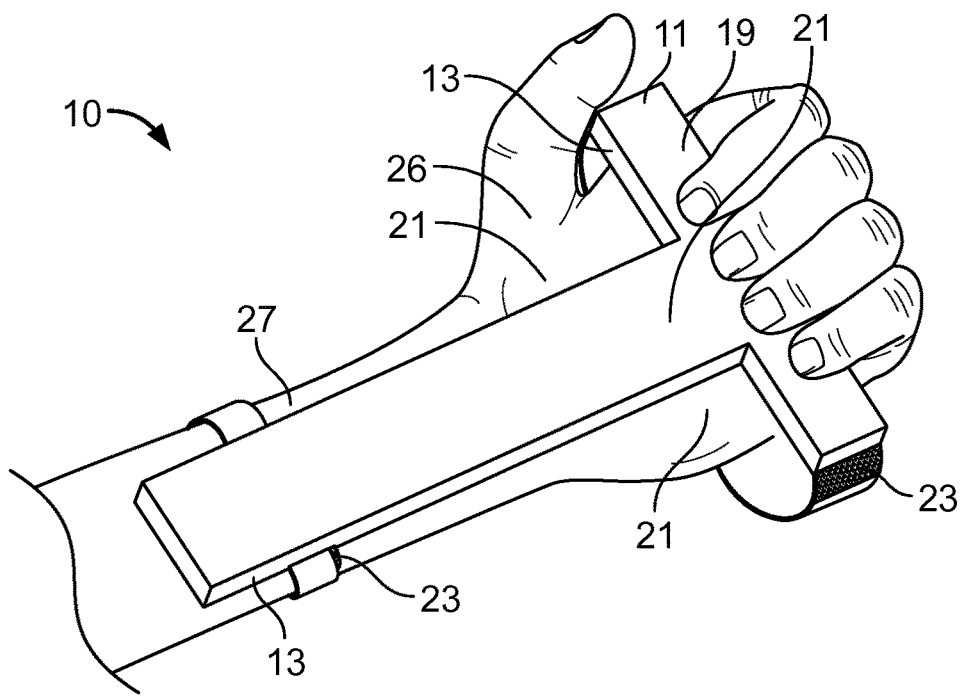
FIG. 8C is a perspective view of the arm support embodiment as shown in FIGS. 8A-8B, where the arm support is closed around a patient, and where the forearm and the palm are visible.

FIGS. 8A-8C disclose examples of an arm support embodiment 10 comprising a T-shaped stabilizer 11 and at least one window 21. The stabilizer 11 has an extremity support surface 12, a bottom 19, and sides 13. The stabilizer 11 is transparent; therefore, the entire stabilizer also acts as a window. Additional windows 21 include the area around the stabilizer where the lower portion of the hand and forearm may be viewed and/or palpated. The two straps 20 are not permanently affixed to the stabilizer 11, but may be attached to the bottom 19, sides 13, or extremity support surface 12 of the stabilizer 11 with the affixing means 22 and the closure means 23. Hook-and-loop fasteners are used as the means for affixing 22 the straps 20 to the stabilizer 11 and as the means for closing 23 the extremity support 10 around a patient. The straps 20 are made of a stretchable material. FIG. 8C shows that a patient's palm 26 and forearm 27 can be viewed with ease through the windows 21 without removing the arm support 10.

Figure 9A:
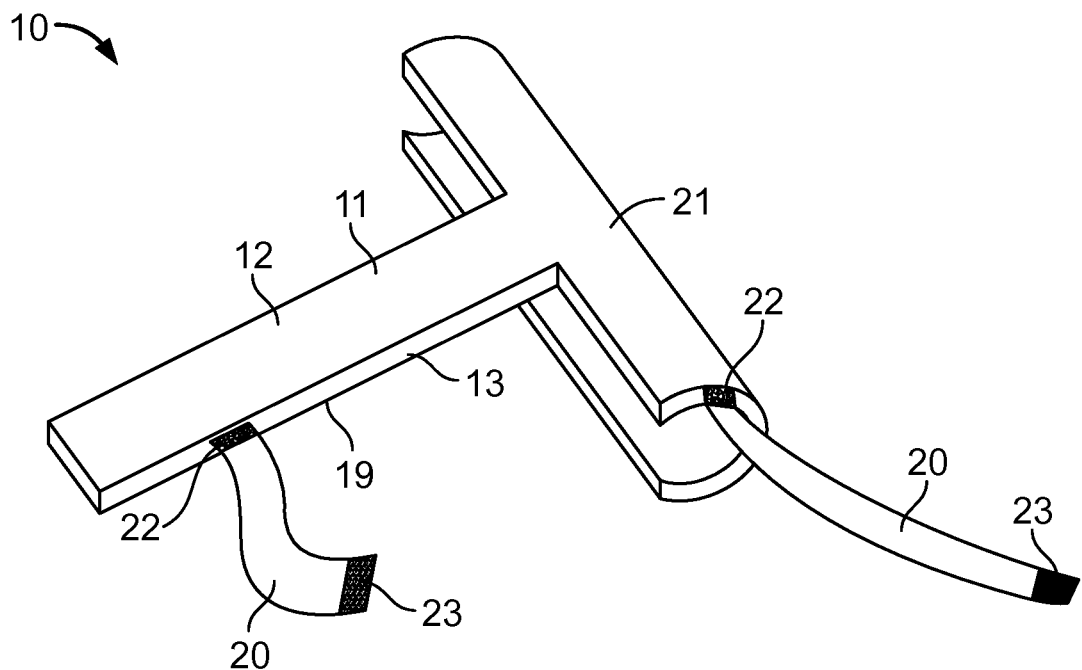
FIG. 9A is a perspective view of an arm support embodiment, where at least a portion of the stabilizer is bendable, and where the straps are affixed to the sides of the stabilizer.
Figure 9B:
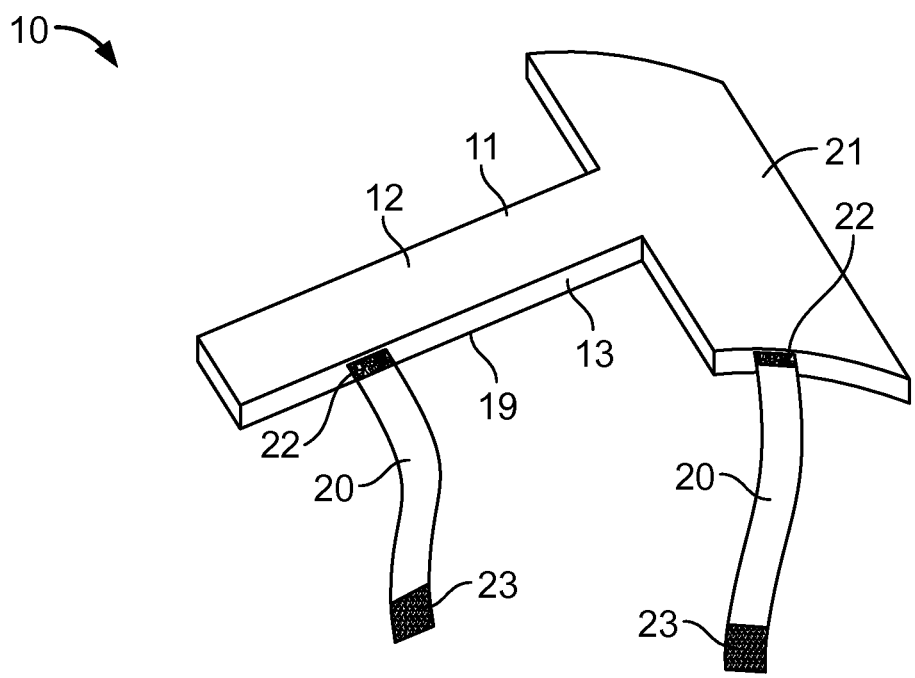
FIG. 9B is a perspective view of an arm support embodiment, where at least a portion of the stabilizer is bendable, and where the straps are affixed to the sides of the stabilizer.
Figure 9C:
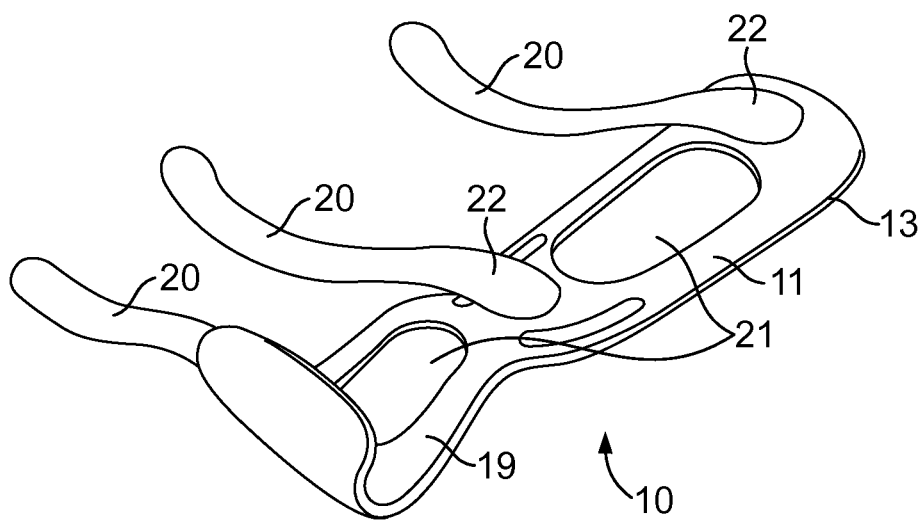
FIG. 9C is a perspective view of an arm support embodiment, where at least a portion of the stabilizer is curved, and where the straps are affixed to the bottom of the stabilizer.
Figure 9D:
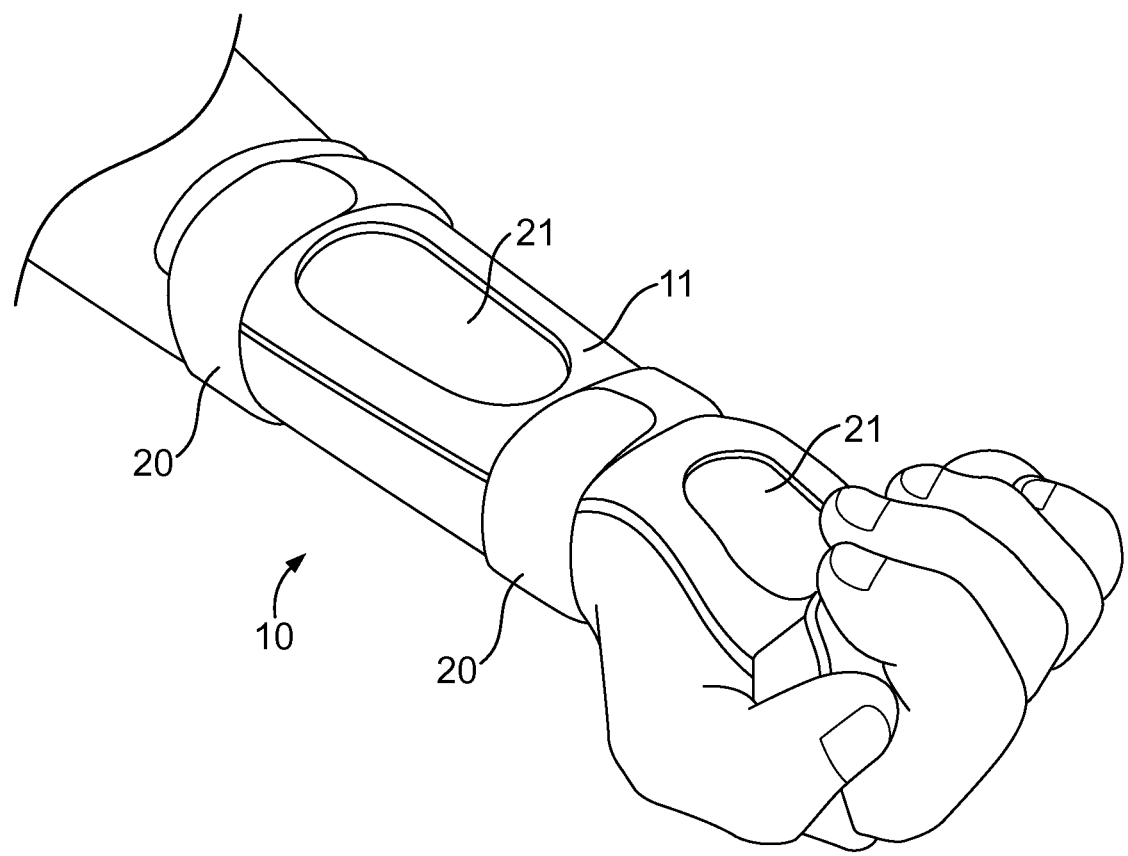
FIG. 9D is a perspective view of an arm support embodiment, where at least a portion of the stabilizer is curved, the straps are affixed to the bottom of the stabilizer, and the arm support is closed around a patient.

FIGS. 9A-9D disclose examples of an arm support embodiment 10 comprising a T-shaped and/or curved stabilizer 11 and at least one window 21. The stabilizer 11 has an extremity support surface 12, a bottom 19, and sides 13. In FIGS. 9A-9B, a portion of the stabilizer 11 is made of a flexible, transparent material. The transparent portion of the stabilizer 11 is a window 21. Additional windows include the area around the stabilizer where the lower portion of the hand and forearm may be viewed and/or palpated. The straps 20 are permanently affixed to sides 13 of the stabilizer 11 by the affixing means 22. However, in another embodiment, the straps 20 may be permanently affixed to bottom 19 or extremity support surface 12 of stabilizer 11 by affixing means 22. The closure means 23 will fasten the arm support embodiment 10 around a patient. FIG. 9D illustrates that a patient's palm 26 and forearm 27 can be viewed with ease through the window 21 without removing the arm support 10.

Figure 10A:
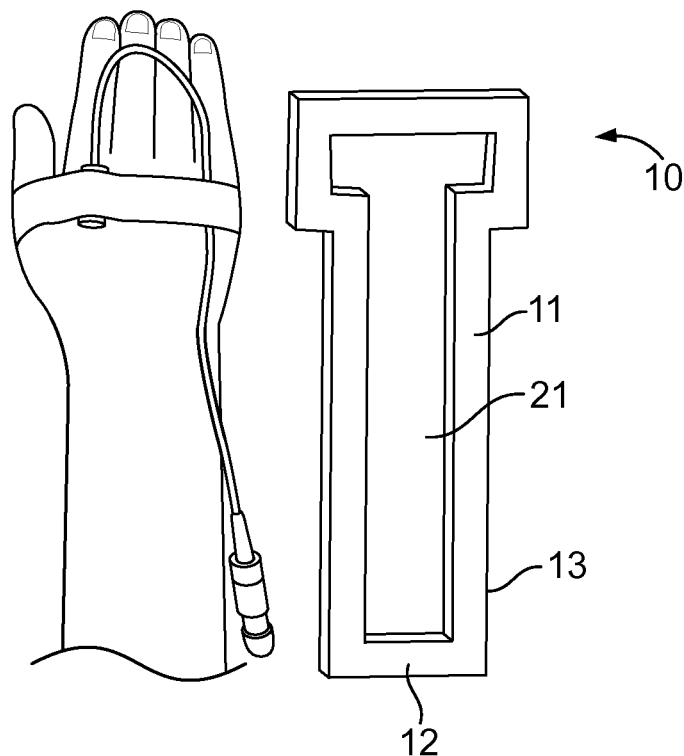
FIG. 10A is a plan view of the top of an arm support embodiment, where the straps are not permanently affixed to the stabilizer, and where the stabilizer is padded.
Figure 10B:
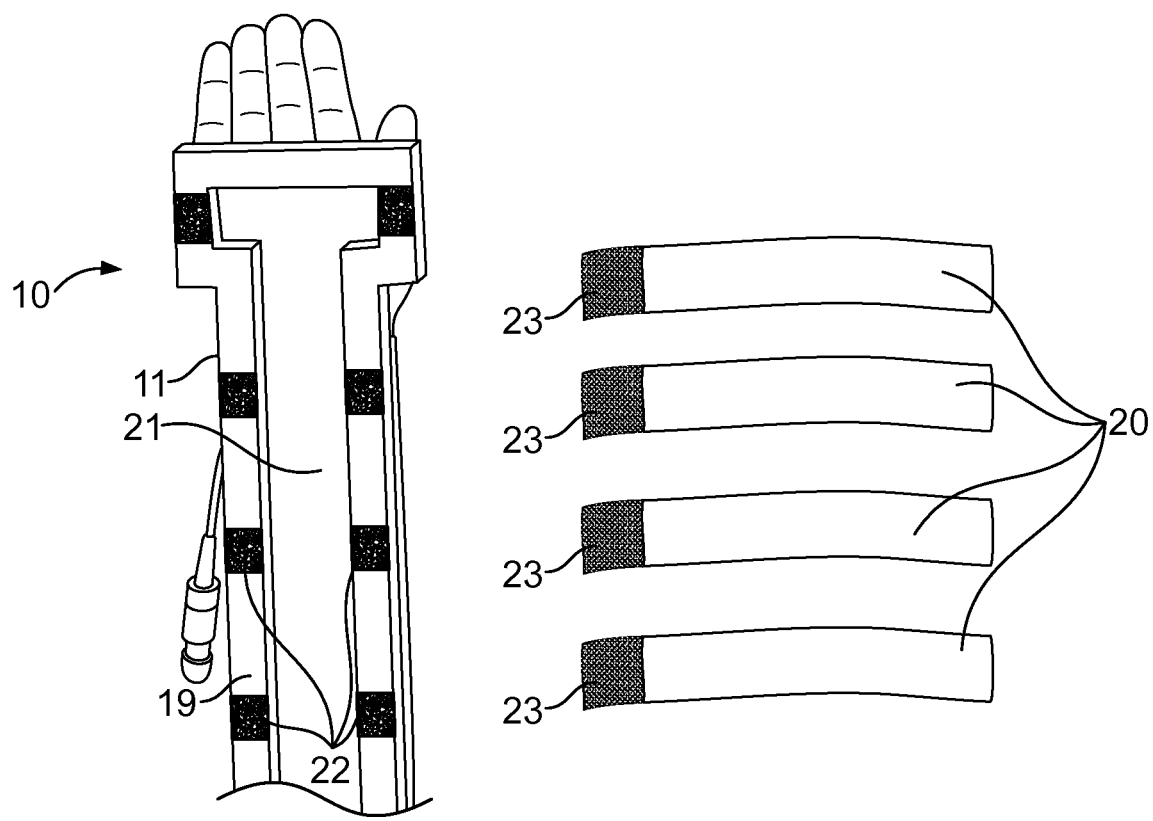
FIG. 10B is a plan view of the bottom of an arm support embodiment, where the straps are not permanently affixed to the stabilizer.
Figure 10C:
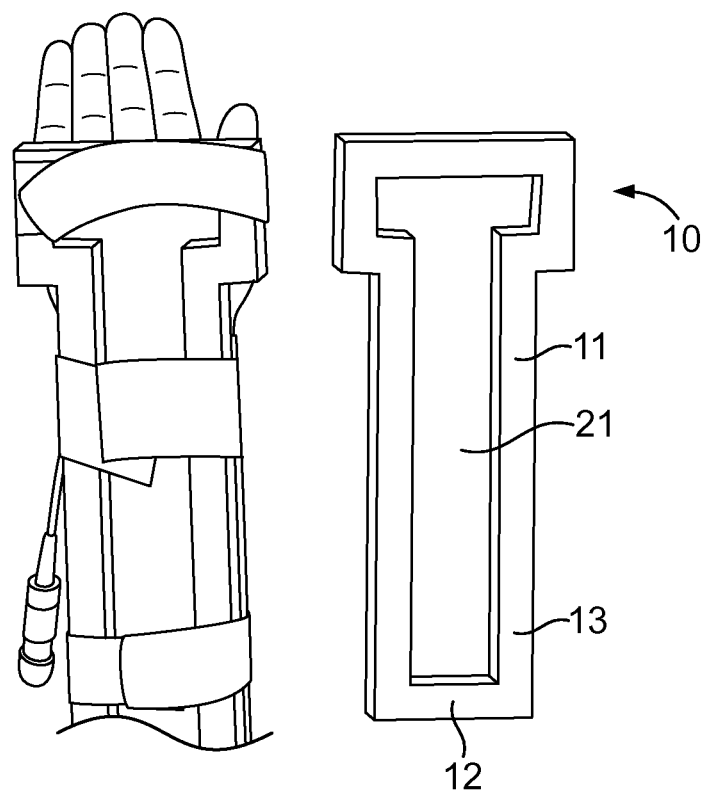
FIG. 10C is a plan view of the bottom of the arm support embodiment as shown in FIGS. 10A-10B and 10D, where the arm support is closed around a patient.
Figure 10D:
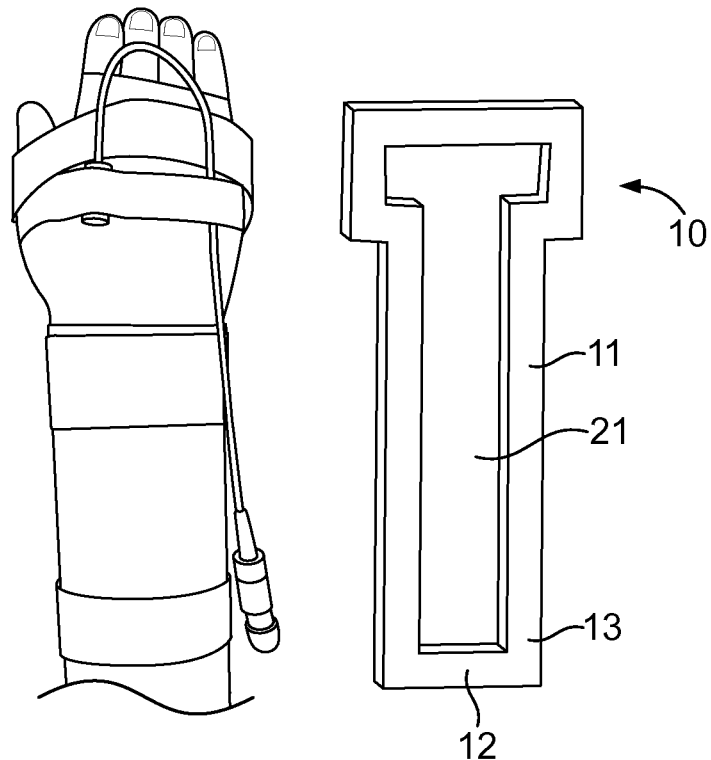
FIG. 10D is a plan view of the top of the arm support embodiment as shown in FIGS. 10A-10C, where the arm support is closed around a patient.

FIGS. 10A-10D disclose examples of an arm support embodiment 10 comprising a T-shaped stabilizer 11, and at least one window 21. In this embodiment, the window 21 is a T-shaped opening in the stabilizer. Additional windows include the area around the stabilizer where the lower portion of the hand and forearm may be viewed and/or palpated. The stabilizer 11 has an extremity support surface 12, a bottom 19, and sides 13. The straps 20 are not permanently affixed to sides 13 of the stabilizer 11 by the affixing means 22. Additionally, the straps 20 that are not permanently affixed could also be affixed to bottom 19 or extremity support surface 12 of stabilizer 11 by affixing means 22. The closure means 23 will fasten the arm support embodiment 10 around a patient. FIG. 10C illustrates that a patient's palm 26 and forearm 27 can be viewed with ease through the window 21 without removing the arm support 10.

Figure 11A:
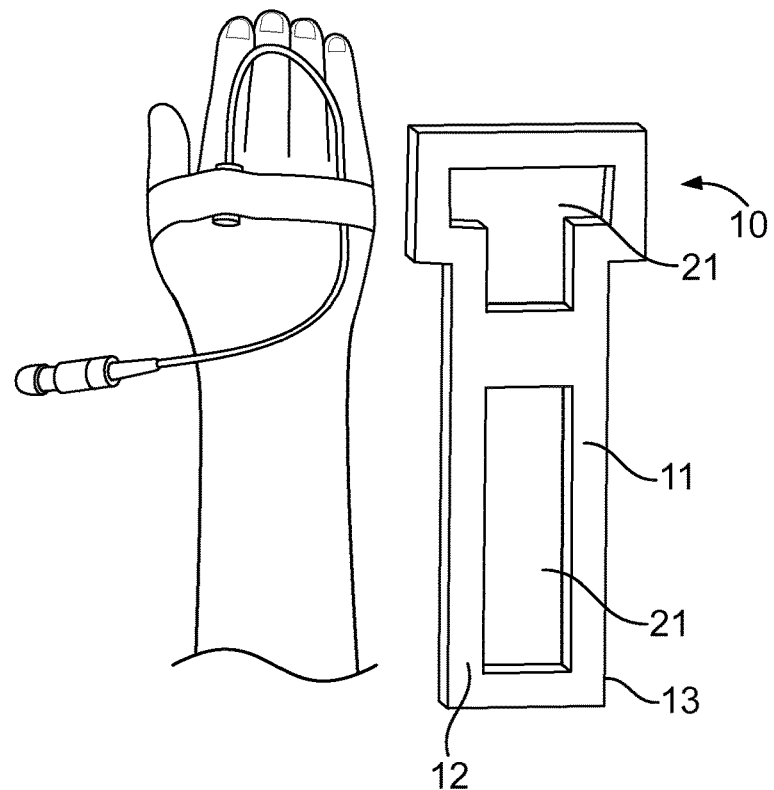
FIG. 11A is a plan view of the top of an arm support embodiment, where the stabilizer further comprises a wrist support.
Figure 11B:
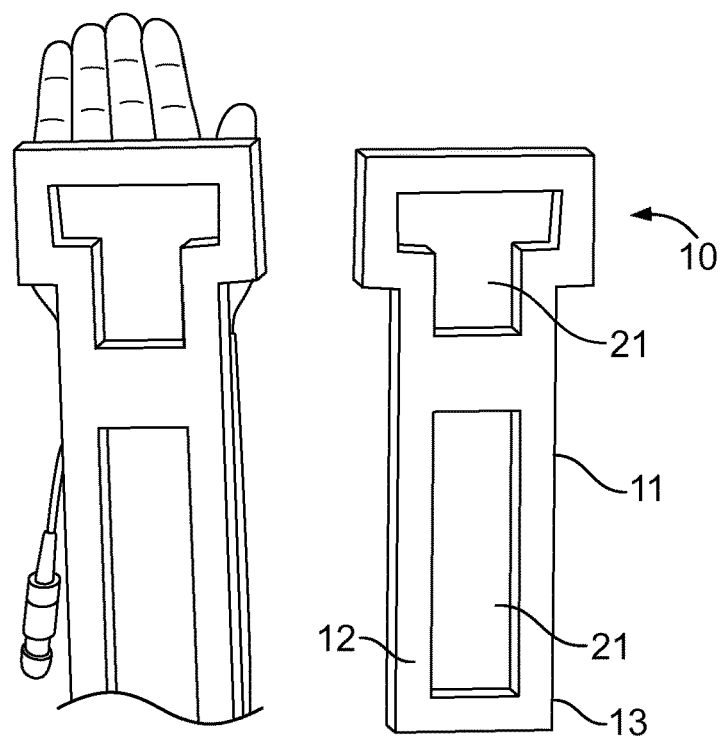
FIG. 11B is a plan view of the bottom of an arm support embodiment, where the stabilizer further comprises a wrist support.
Figure 11C:
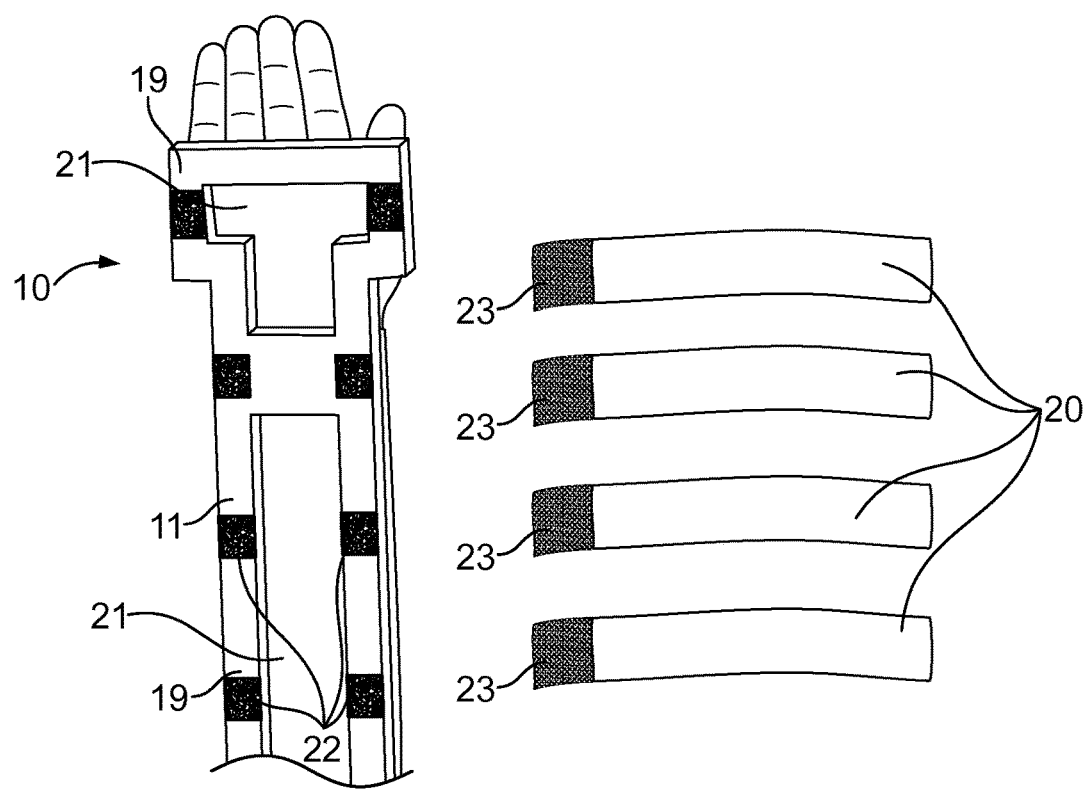
FIG. 11C is a plan view of the bottom of an arm support embodiment, where the stabilizer further comprises a wrist support and where the straps are not permanently affixed to the stabilizer.
Figure 11D:
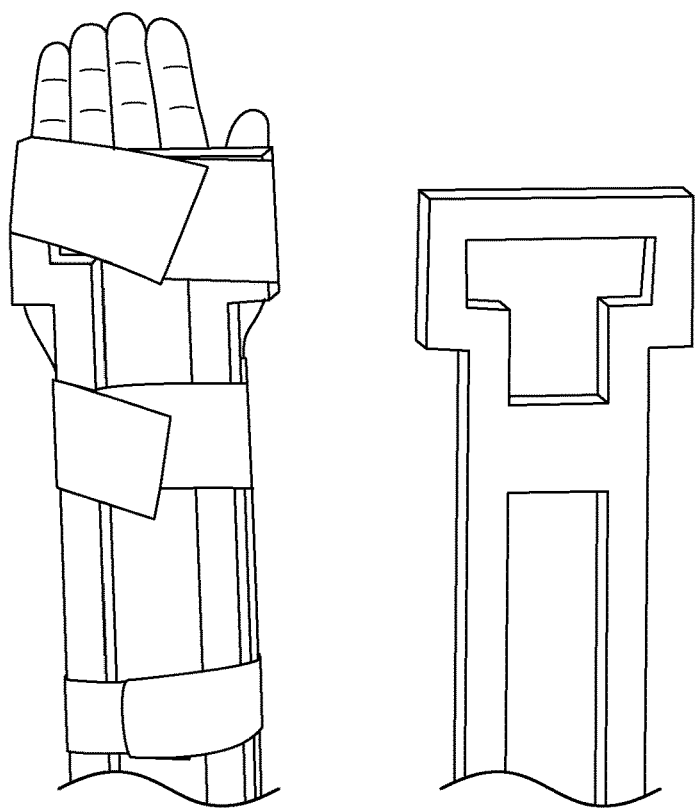
FIG. 11D is a plan view of the bottom of the arm support embodiment as shown in FIGS. 11A-11C and 11E, where the arm support is closed around a patient.
Figure 11E:
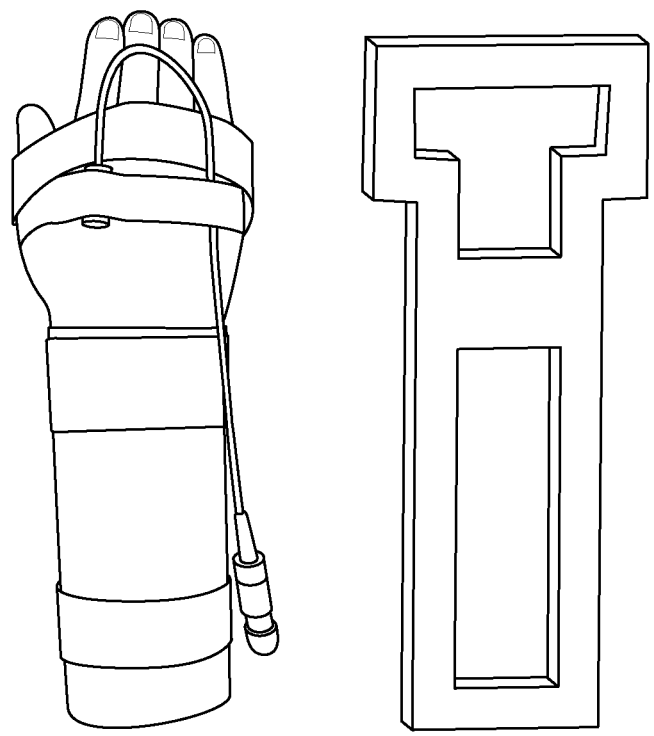
FIG. 11E is a plan view of the top of the arm support embodiment as shown in FIGS. 11A-11D, where the arm support is closed around a patient.

FIGS. 11A-11E disclose examples of an arm support embodiment 10 comprising a T-shaped stabilizer 11 and at least two windows 21. In this embodiment, the two windows 21 comprise a T-shaped opening in the stabilizer, as well as a rectangular opening in the stabilizer. Additional windows include the area around the stabilizer where the lower portion of the hand and forearm may be viewed and/or palpated. The stabilizer 11 has an extremity support surface 12, a bottom 19, and sides 13. The stabilizer also contains a wrist support. The straps 20 are not permanently affixed to sides 13 of the stabilizer 11 by the affixing means 22. The straps 20 that are not permanently affixed could also be affixed to bottom 19 or extremity support surface 12 of stabilizer 11 by affixing means 22. The closure means 23 will fasten the arm support embodiment 10 around a patient. FIG. 11D illustrates that a patient's palm 26 and forearm 27 can be viewed with ease through the window 21 without removing the arm support 10.

Figure 12A:
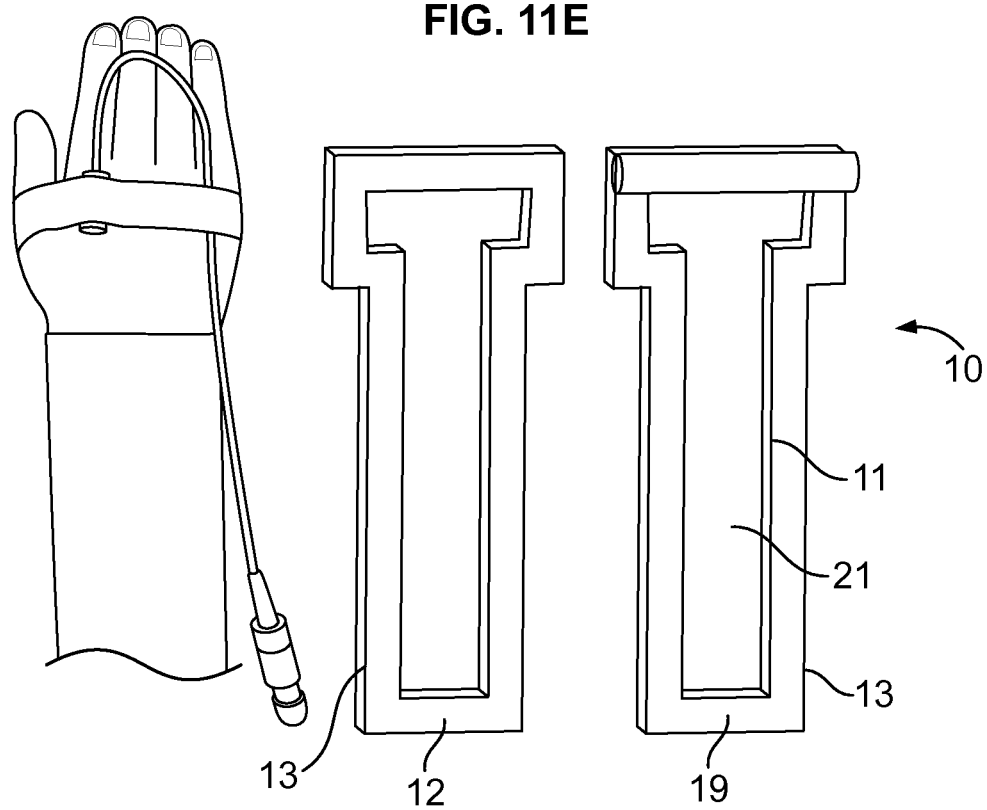
FIG. 12A is a plan view of the top of an arm support embodiment, where the stabilizer further comprises a hand roll for the patient to grasp.
Figure 12B:
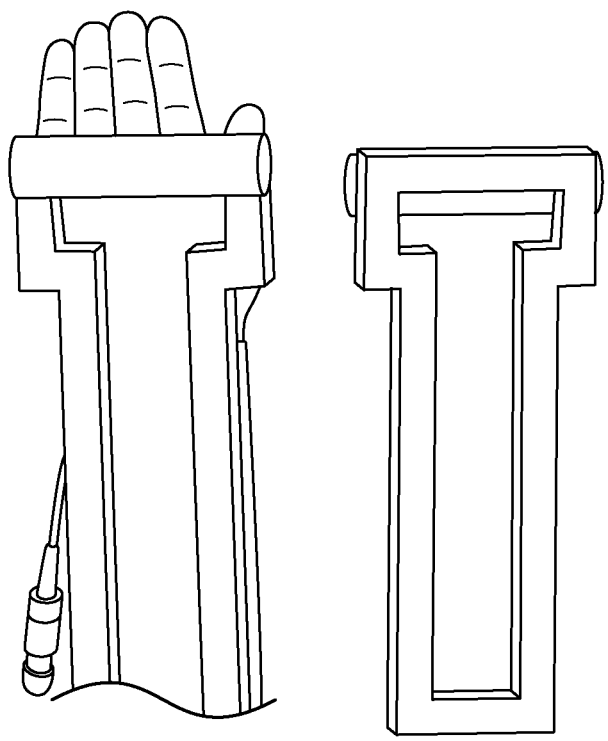
FIG. 12B is a plan view of the bottom of an arm support embodiment, where the stabilizer further comprises a hand roll for the patient to grasp.
Figure 12C:
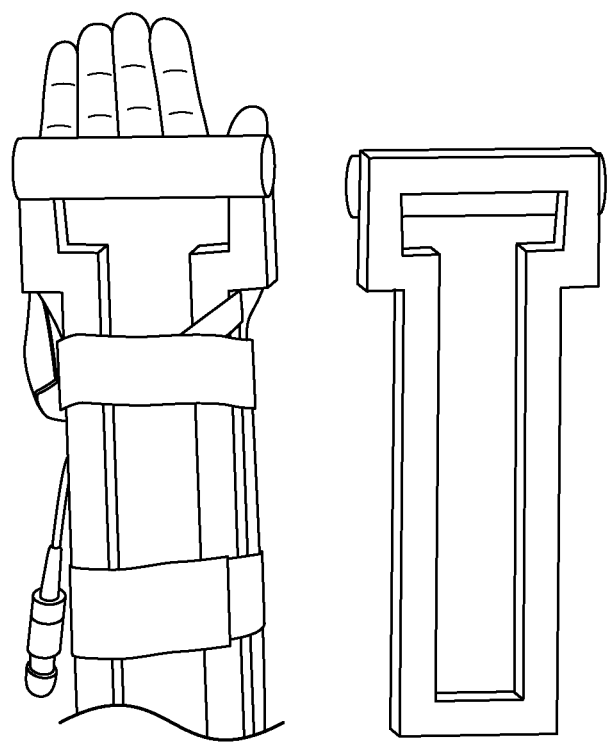
FIG. 12C is a plan view of the bottom of the arm support embodiment as shown in FIGS. 12A-12B and 12D, where the arm support is closed around a patient.
Figure 12D:
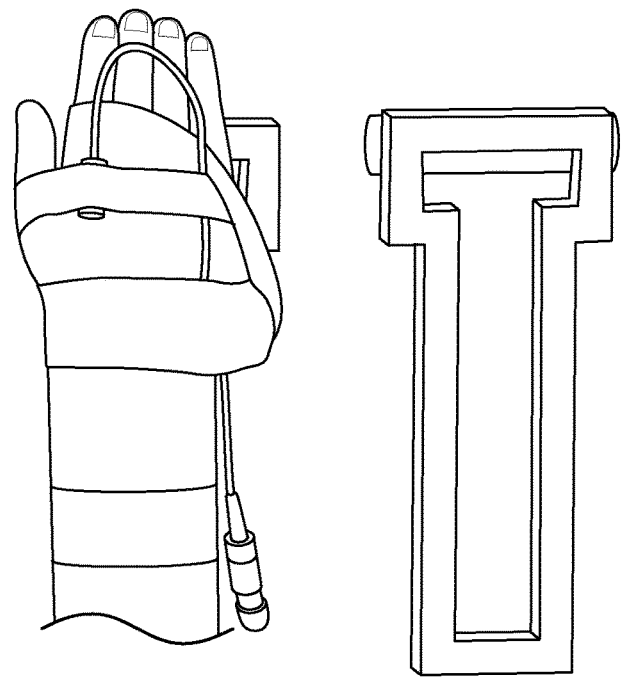
FIG. 12D is a plan view of the top of the arm support embodiment as shown in FIGS. 12A-12C, where the arm support is closed around a patient.

FIGS. 12A-12D disclose examples of an arm support embodiment 10 comprising a T-shaped stabilizer 11, at least one window 21, and a hand roll for a patient to grasp. Additional windows include the area around the stabilizer where the lower portion of the hand and forearm may be viewed and/or palpated. The stabilizer 11 has an extremity support surface 12, a bottom 19, and sides 13. Straps are not shown in FIGS. 12A-12B. However, straps could be used in these embodiments. For example, straps 20 may be affixed to sides 13, bottom 19, or extremity support surface 12 of the stabilizer 11 by an affixing means 22. Further, in FIGS. 12C and 12D, a closure means 23 may fasten the arm support embodiment 10 around a patient. FIG. 12C illustrates that a patient's palm 26 and forearm 27 can be viewed with ease through the window 21 without removing the arm support 10.

Figure 13A:
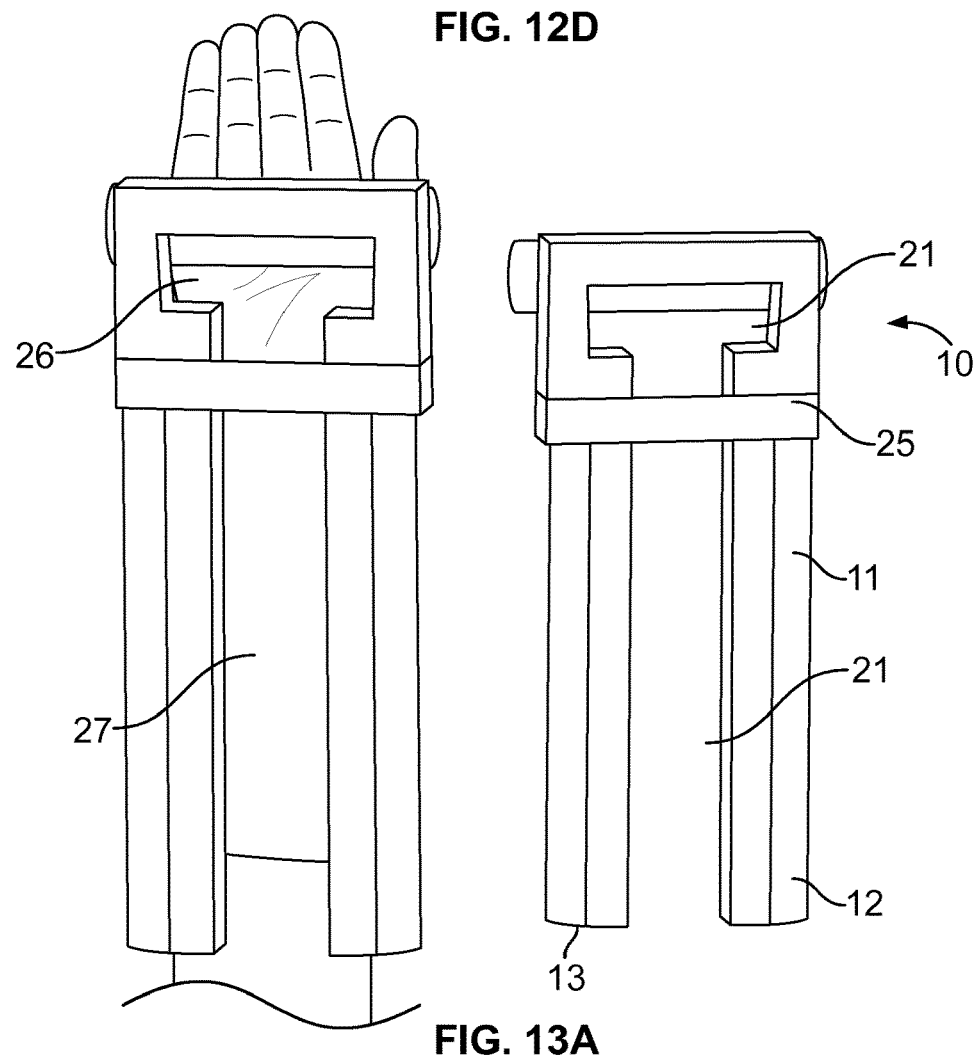
FIG. 13A is a plan view of the bottom of an arm support, where the stabilizer is contoured to fit the side of a patient's arm.
Figure 13B:
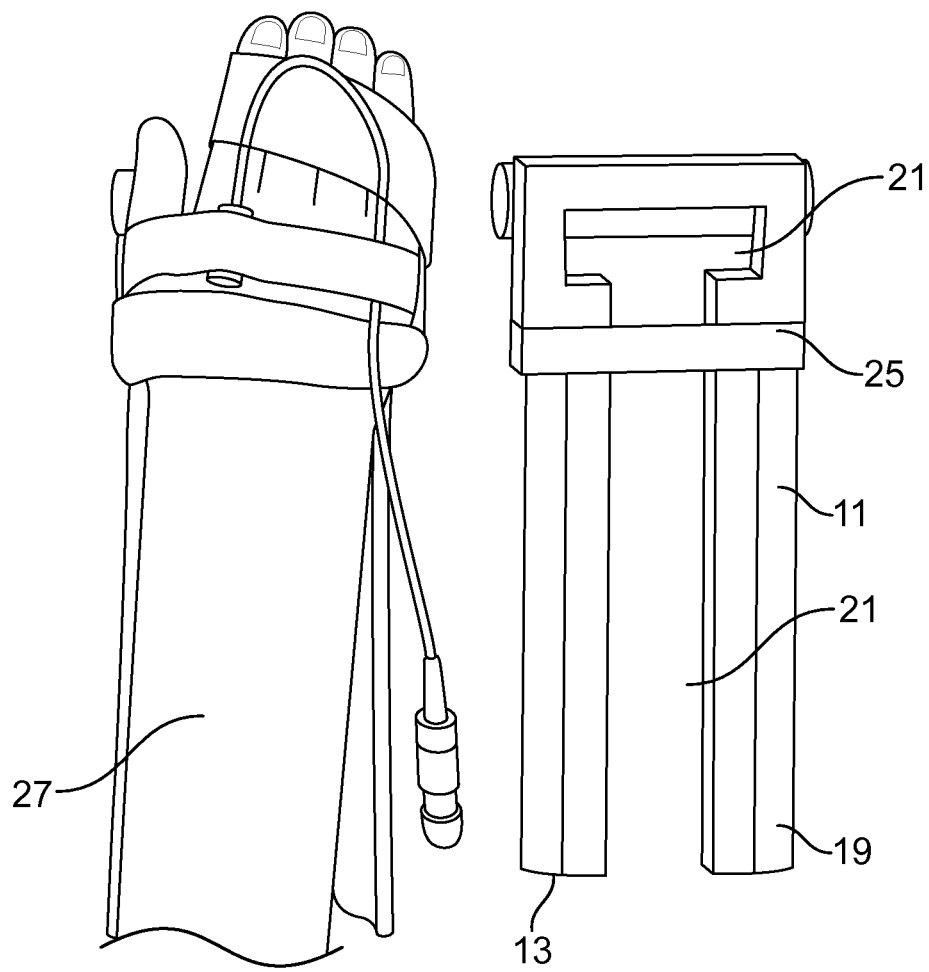
FIG. 13B is a plan view of the top of the arm support as shown in FIG. 13A, where the support is closed around a patient.

FIGS. 13A and 13B disclose examples of an arm support embodiment 10 comprising a stabilizer 11, at least two windows 21, and a hand roll for a patient to grasp. The two windows 21 comprise a T-shaped opening in the stabilizer, as well as a rectangular opening in the stabilizer. Additional windows include the area around the stabilizer where the lower portion of the hand and forearm may be viewed and/or palpated. The stabilizer 11 has an extremity support surface 12, a bottom 19, and sides 13. The stabilizer also contains a wrist support 25. The sides 13 are bent to support the side of the arm so that the support surface is actually resting on the back of the forearm and bent to wrap around the side of the arm, cradling the forearm. FIG. 13A illustrates that a patient's palm 26 and forearm 27 can be viewed with ease through the window 21 without removing the arm support 10.

Figure 14A:
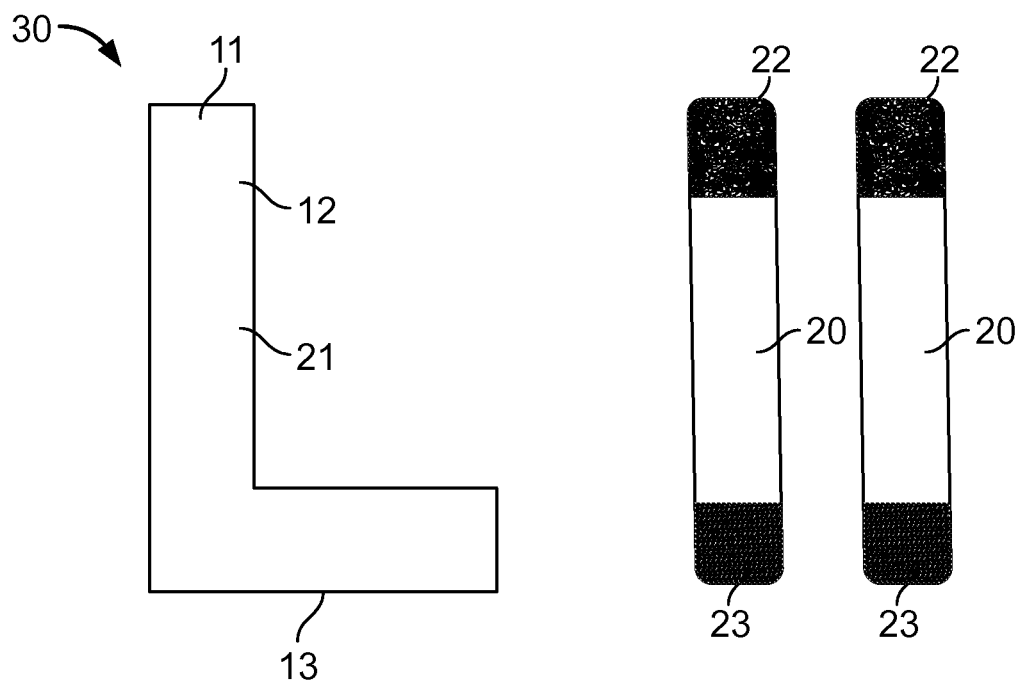
FIG. 14A is a plan view of the top of a leg support embodiment, where the straps are not permanently affixed to a transparent stabilizer.
Figure 14B:
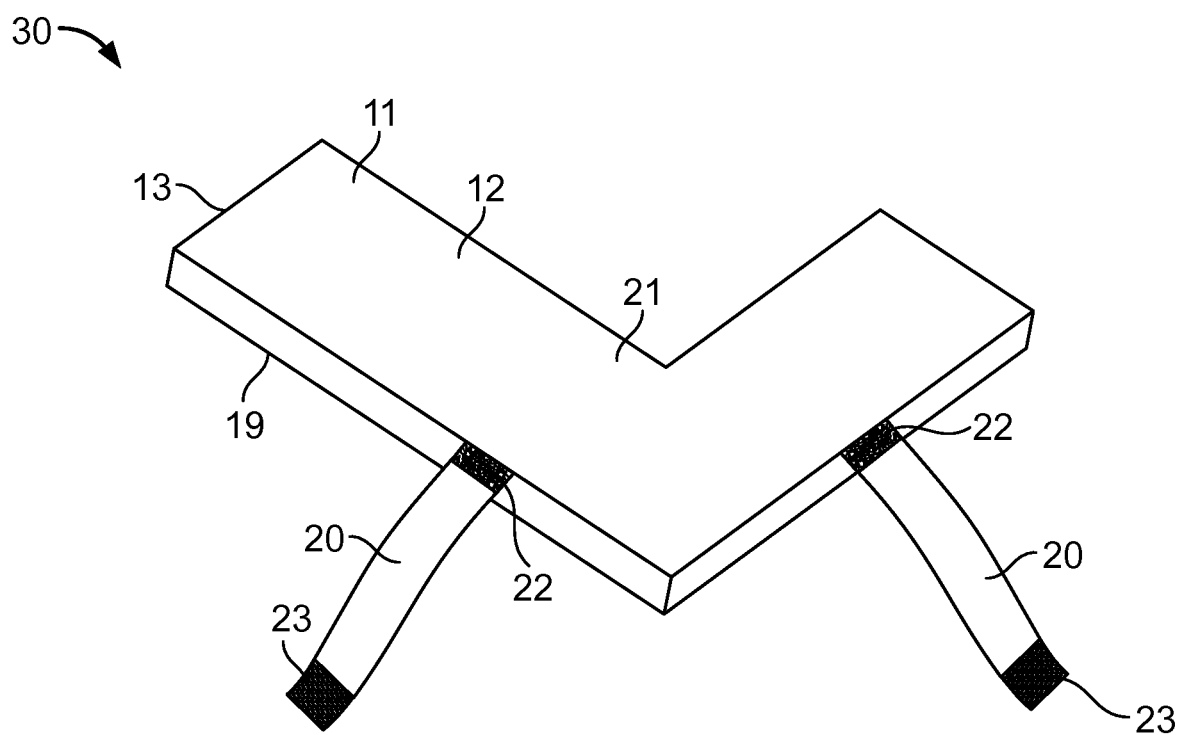
FIG. 14B is a perspective view of a leg support embodiment, where the straps are affixed to a transparent stabilizer.
Figure 14C:
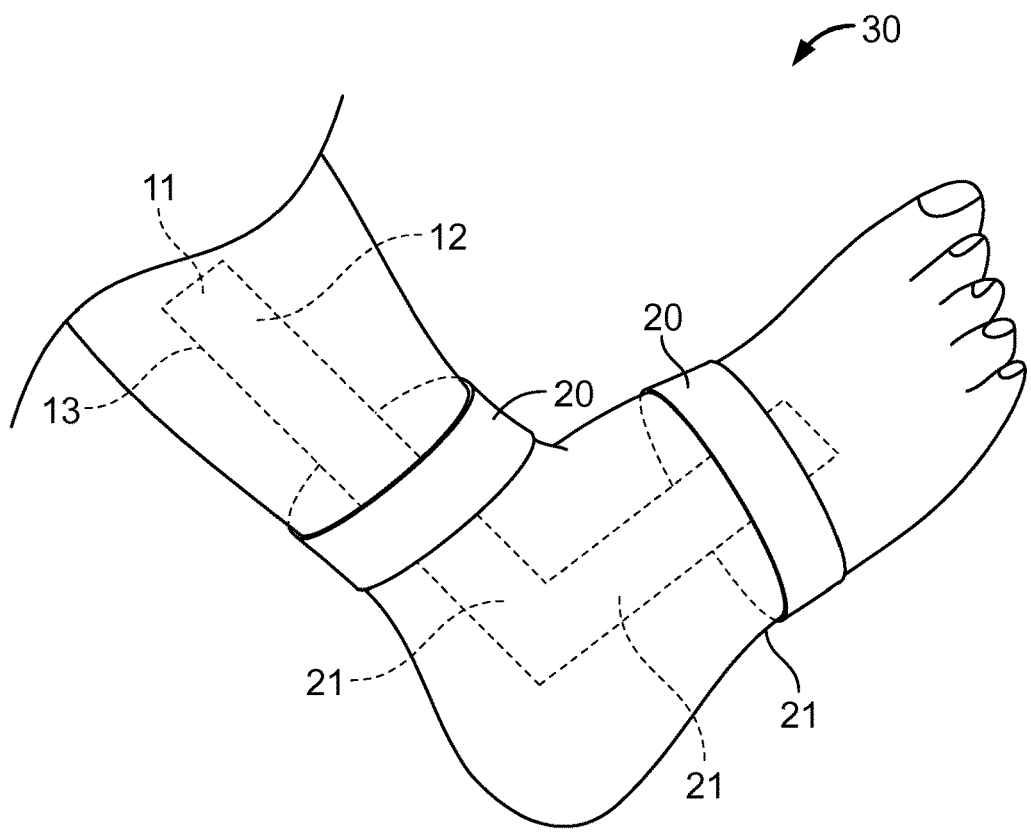
FIG. 14C is a perspective view of a leg support embodiment as shown in FIGS. 14A-B, where the leg support is closed around a patient.

FIGS. 14A-14C disclose examples of a leg support embodiment 30 comprising an L-shaped stabilizer 11 and at least one window 21. The stabilizer 11 has an extremity support surface 12, a bottom 19, and sides 13. The stabilizer 11 is made of a transparent material. The transparent portion of the stabilizer 11 is a window 21. Additional windows include the area around the stabilizer 11, where the lower portion of the leg and foot may be viewed and/or palpated. The two straps 20 are permanently affixed to the sides 13 of the stabilizer 11 by the affixing means 22. Yet, in another embodiment, the straps 20 may be permanently affixed to bottom 19 or extremity support surface 12 of stabilizer 30 by affixing means 22. The closure means 23 will fasten the leg support embodiment 30 around a patient. FIG. 14C shows that a patient's leg 31 and foot 32 can be viewed with ease through the windows 21 without removing the leg support 30. In this embodiment, the stabilizer 11 also acts as the window 11.

Figure 15A:
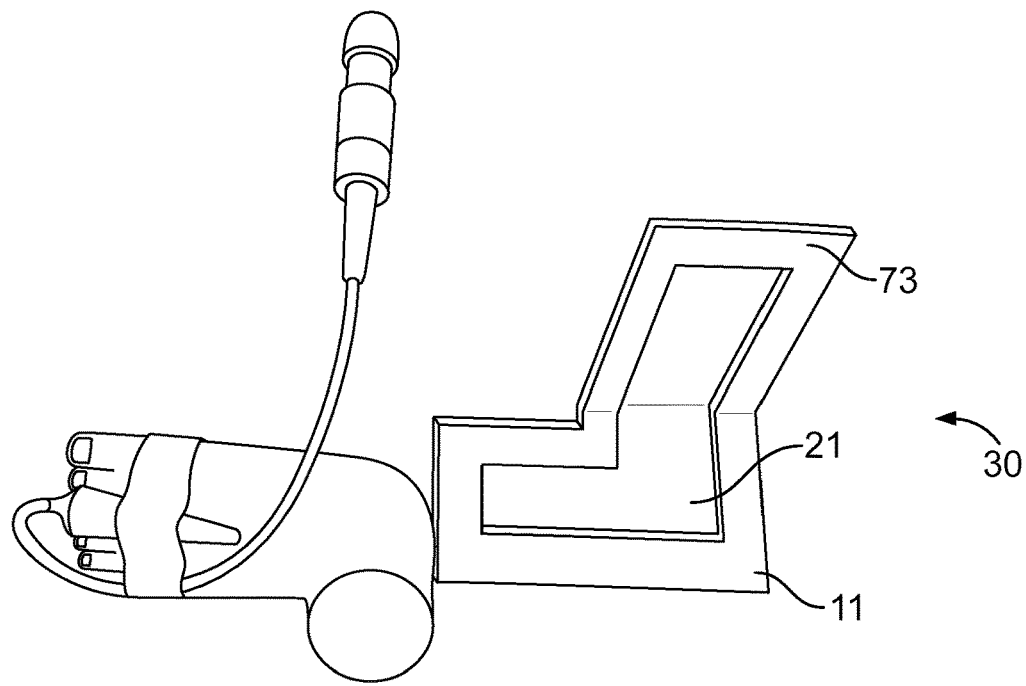
FIG. 15A is a perspective view of a foot support embodiment.
Figure 15B:
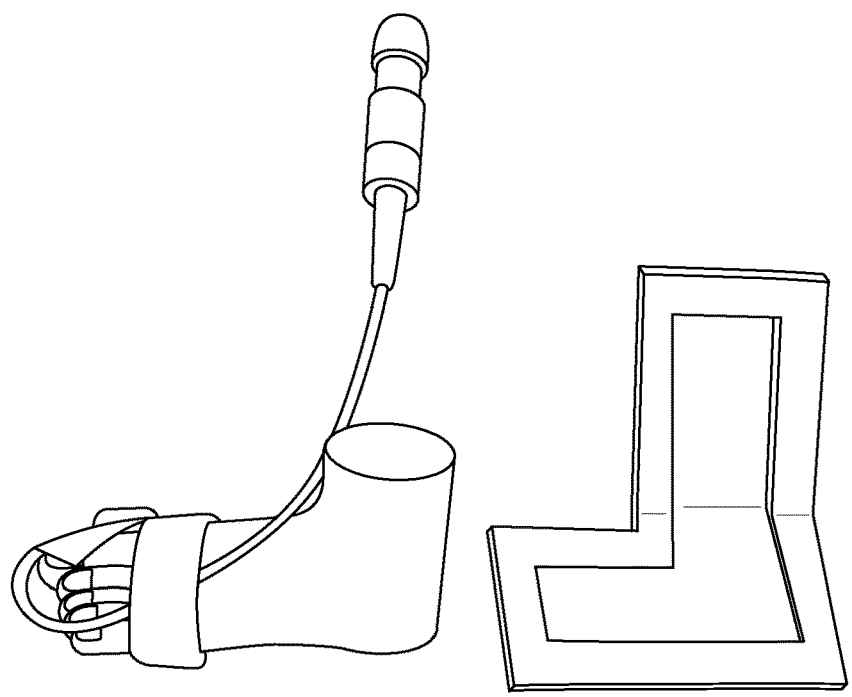
FIG. 15B is a side view of a foot support embodiment.
Figure 15C:
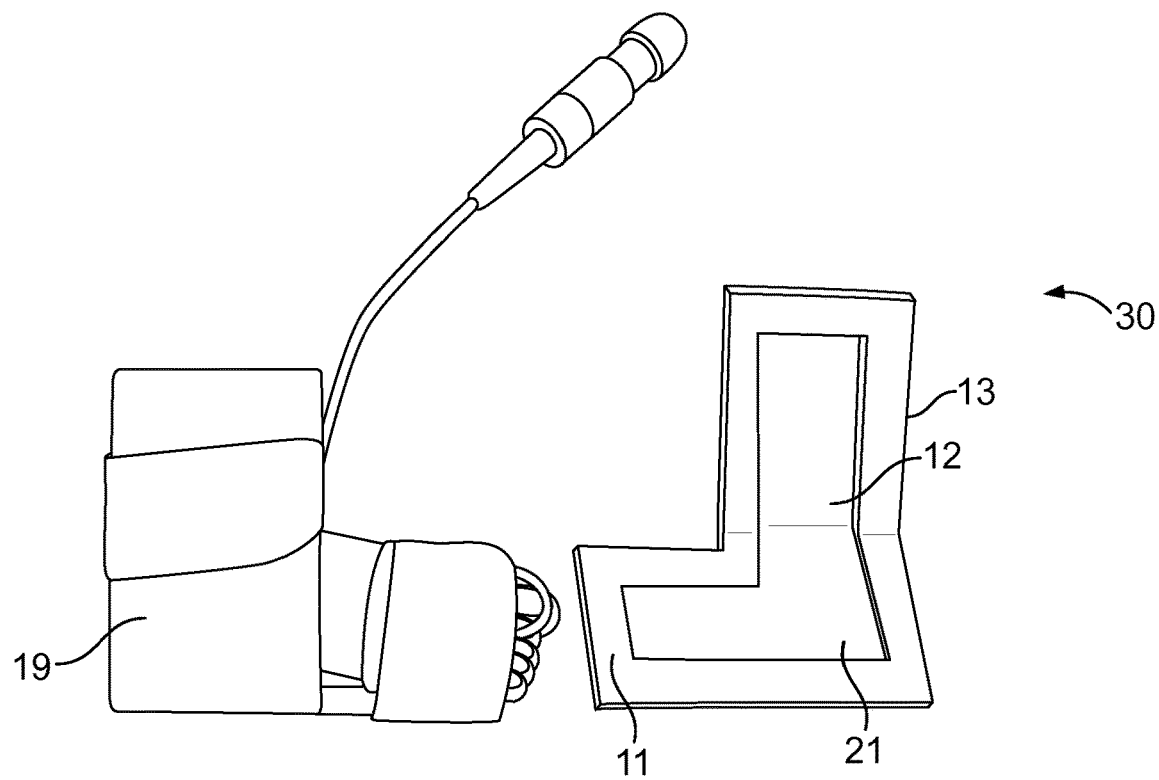
FIG. 15C is a side view of the foot support embodiment as shown in FIGS. 15A-B and 15D, where the foot support is closed around a patient.
Figure 15D:
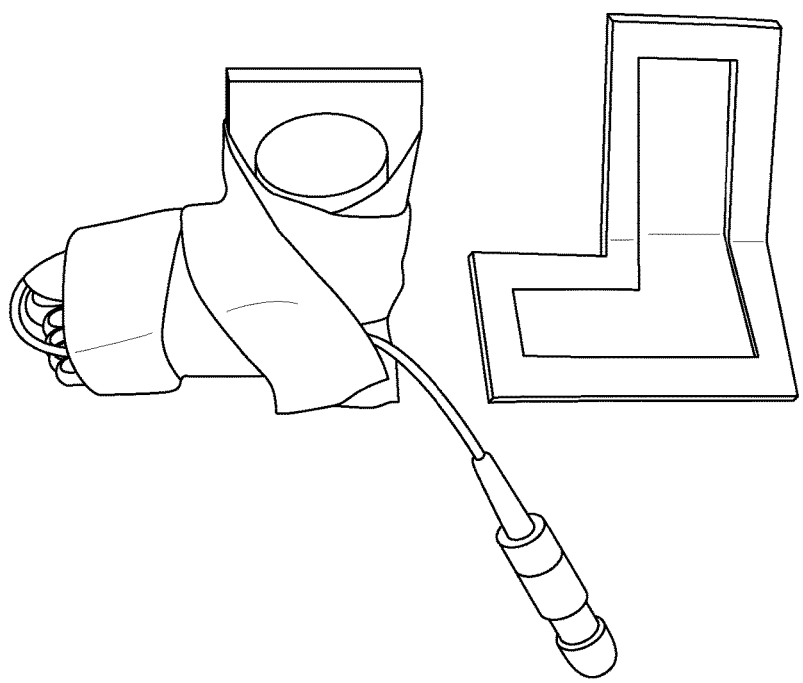
FIG. 15D is a perspective view of a foot support embodiment as shown in FIGS. 15A-15C, where the foot support is closed around a patient.

FIGS. 15A-15D disclose examples of leg support embodiments 30 comprising an L-shaped stabilizer 11 and at least one window 21. The stabilizer 11 has an extremity support surface 12, a bottom 19, and sides 13. In one embodiment, the stabilizer 11 is made of a transparent material. The transparent portion of the stabilizer 11 is a window 21. In another embodiment, the stabilizer comprises an L-shaped opening that is the window 21. Additional windows for both embodiments include the area around the stabilizer, where the lower portion of the leg and foot may be viewed and/or palpated. In FIGS. 15A-15D, the patient's foot would rest directly on the lower portion of the L-shaped stabilizer, and the top of the "L" would be perpendicular to the lower portion, providing support to the patient's ankle. The straps 20 (not shown in FIGS. 15A and 15B) are not permanently affixed to sides 13 of the stabilizer 11 by the affixing means 22. However, the straps 20 may be affixed to bottom 19, sides 13, or extremity support surface 12 of stabilizer 11 by affixing means 22. A closure means 23 can fasten the leg support embodiment 30 around a patient, as illustrated in FIGS. 15C and 15D. In one embodiment, and as illustrated in FIGS. 15A-15D, the stabilizer 11 further comprises foam padding 73. FIG. 15C also shows that a patient's ankle and lower leg can be viewed with ease through the windows 21 without removing the leg support 30.

Figure 16A:
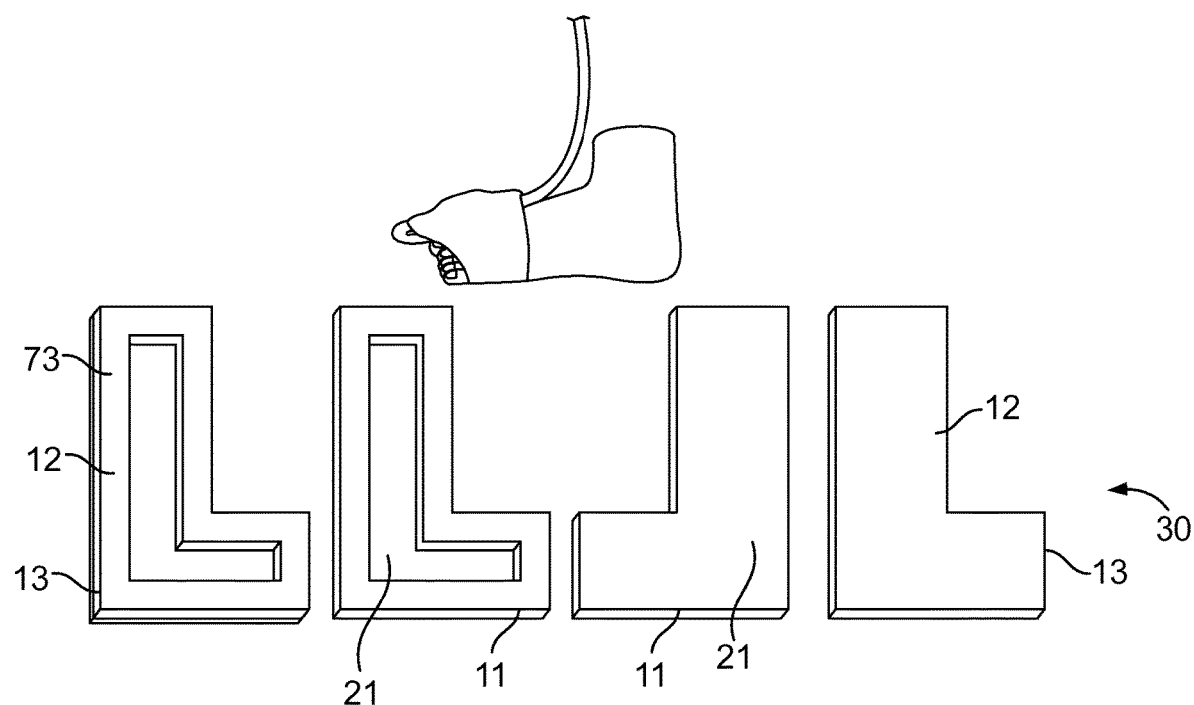
FIG. 16A is a plan view of foot support embodiments.
Figure 16B:
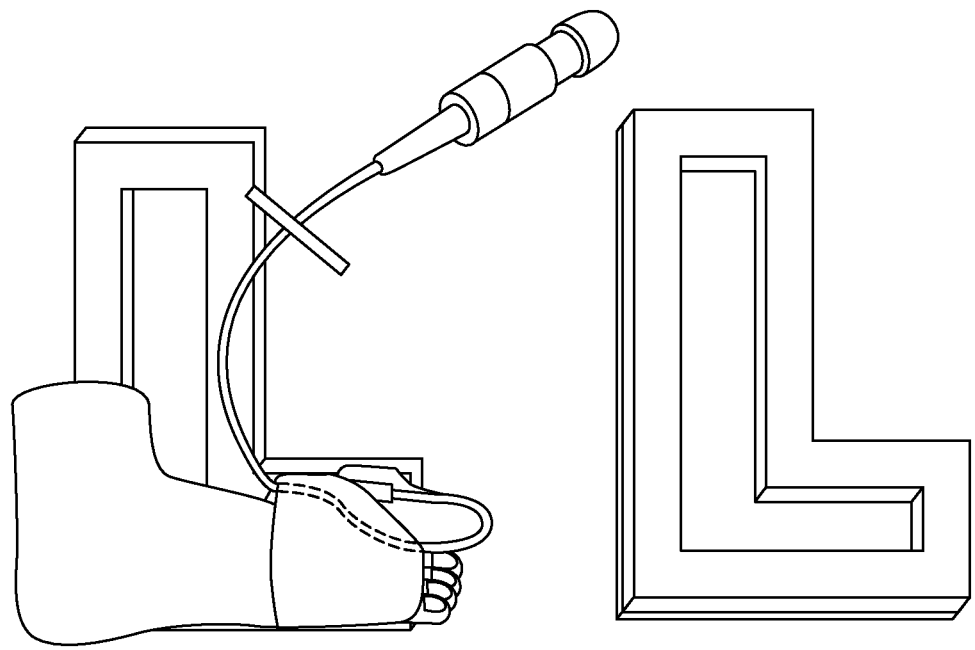
FIG. 16B is a side view of the foot support embodiment of FIG. 16A, where the foot support is on a patient.
Figure 16C:
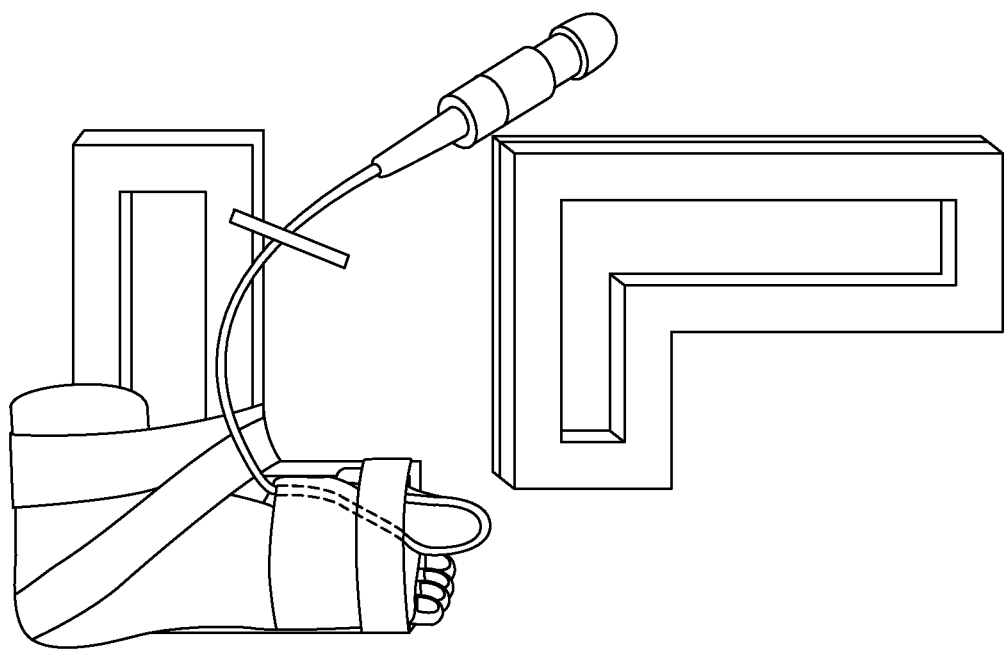
FIG. 16C is a side view of the foot support embodiments of FIGS. 16A-16B, where the foot support is closed around a patient.

FIGS. 16A-16C disclose examples of leg support embodiments 30 comprising an L-shaped stabilizer 11, and at least one window 21. The stabilizer 11 has an extremity support surface 12, a bottom 19, and sides 13. In one embodiment, the stabilizer 11 is made of a transparent material. The transparent portion of the stabilizer 11 is a window 21. In another embodiment, the stabilizer comprises an L-shaped opening that is the window 21. Additional windows for both embodiments include the area around the stabilizer, where the lower portion of the leg and foot may be viewed and/or palpated. The straps 20 (not shown in FIGS. 16A and 16B) are not permanently affixed to sides 13 of the stabilizer 11 by the affixing means 22. However, the straps 20 may be affixed to bottom 19, sides 13, or extremity support surface 12 of stabilizer 11 by affixing means 22. A closure means 23 may fasten the leg support embodiment 30 around a patient, as illustrated in FIG. 16C. Further, FIG. 16A illustrates a stabilizer 11 comprising foam padding 73 along its perimeter. However, the entire stabilizer support surface may be covered in transparent foam padding.

Figure 17:
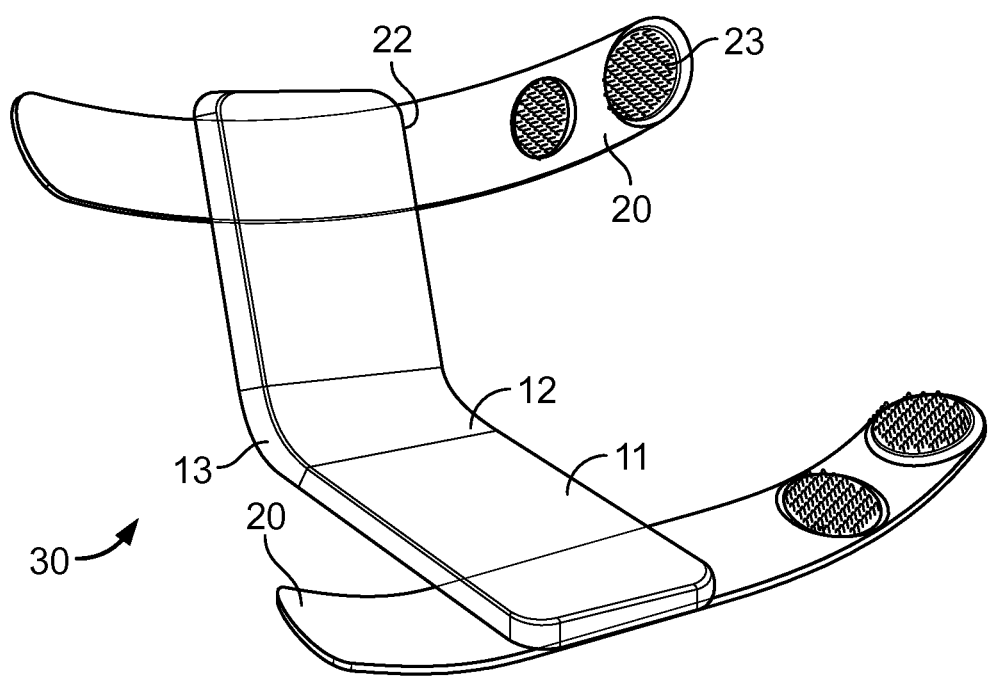
FIG. 17 is a perspective view of a leg support embodiment, where the straps are affixed to a transparent stabilizer.
Figure 18A:
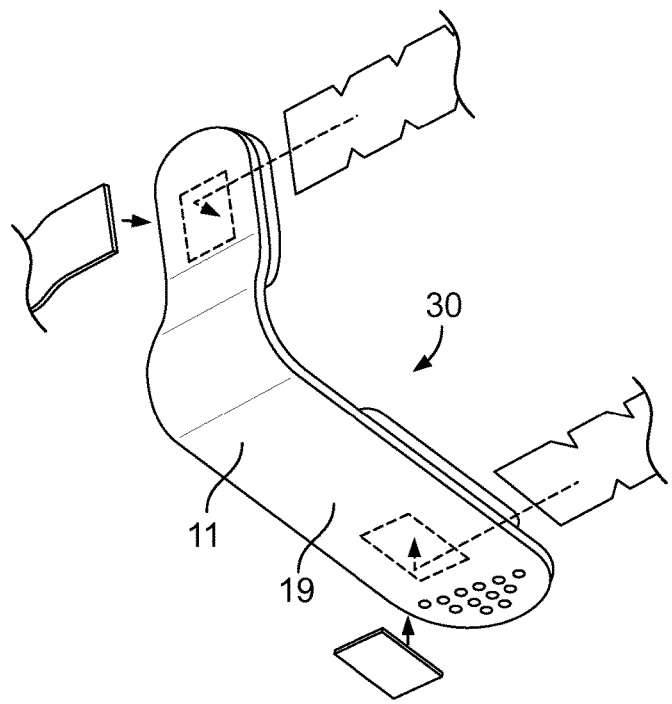
FIG. 18A is a perspective view of a leg support embodiment, where the straps are not affixed to a transparent stabilizer.
Figure 18B:
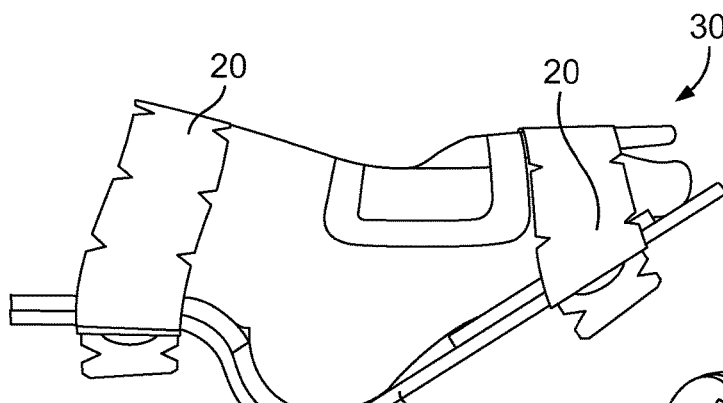
FIG. 18B is a side view of a leg support embodiment, where the straps are affixed to a transparent stabilize, and where the foot support is closed around a patient.
Figure 18C:
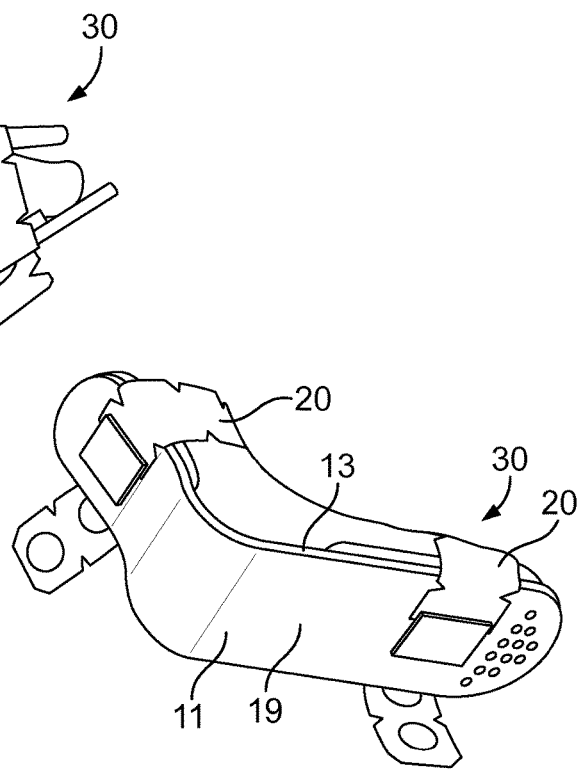
FIG. 18C is a perspective view of a leg support embodiment, where the straps are affixed to a transparent stabilizer, and where the foot support is closed around a patient.

FIGS. 17 and 18A-18C disclose examples of leg support embodiments 30, where the straps 20 are affixed to a transparent stabilizer 11. The stabilizer 11 has an extremity support surface 12, a bottom 19, and sides 13. In one embodiment, the stabilizer 11 is made of a transparent material. The transparent portion of the stabilizer 11 is a window 21. In FIG. 17, the two straps 20 are permanently affixed to the sides 13 of the stabilizer 11 by the affixing means 22. Yet, in another embodiment, the straps 20 may be permanently affixed to bottom 19, sides 13 or extremity support surface 12 of stabilizer 11 by affixing means 22. The closure means 23 will fasten the leg support embodiment 30 around a patient. FIG. 18C also shows that a patient's ankle and lower leg can be viewed with ease through the windows 21 without removing the leg support 30.

FIGS. 19A-19D disclose examples of leg support embodiments 30 comprising at least one window and at least one anchor 60. Further, in these embodiments, the straps 20 comprise slits or openings to accommodate and attach to the anchors 60. These Figures illustrate the sidewall touching the patient's foot and ankle, while the heel of the patient's foot is resting in an opening. These Figures also provide openings or holes in the stabilizer for ventilation.

Figure 19H:
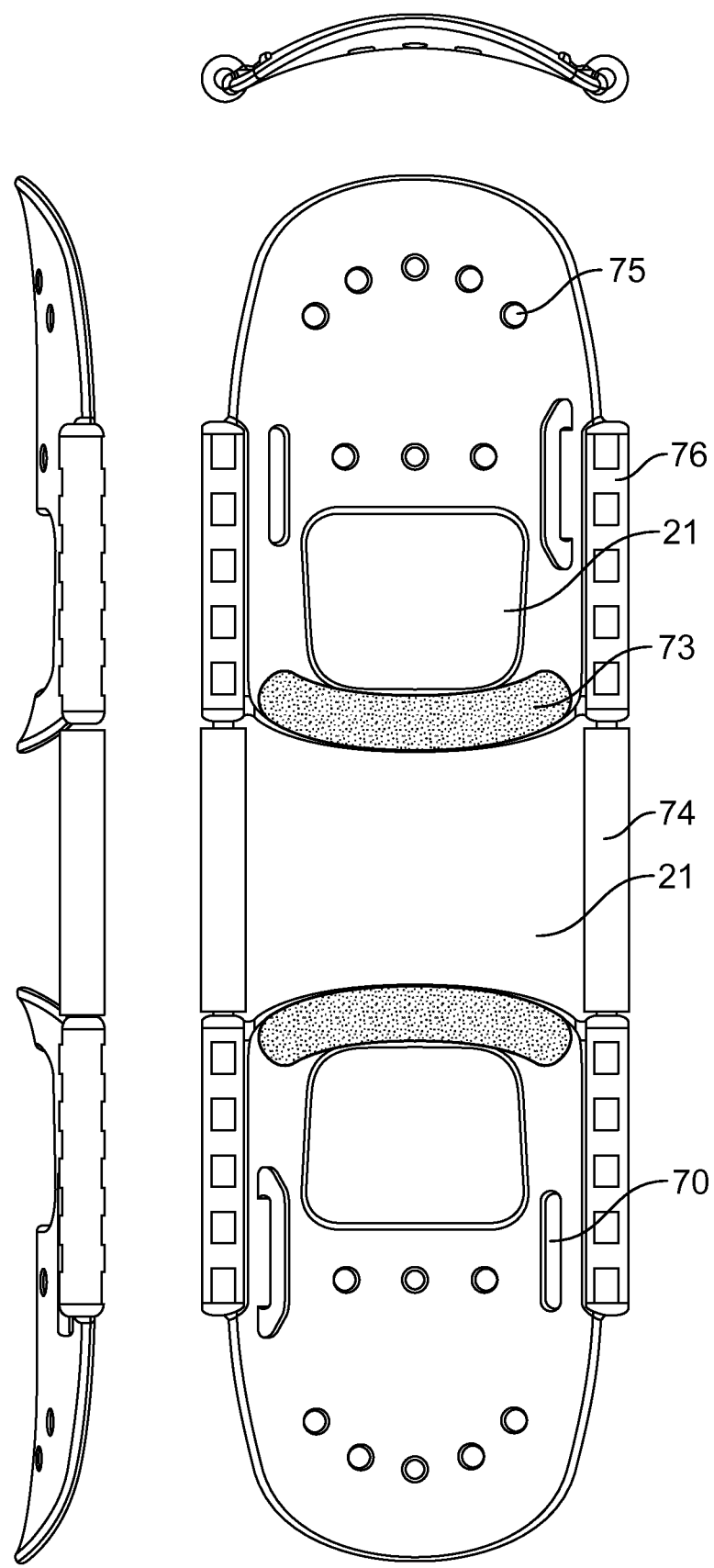
Figure 19I:
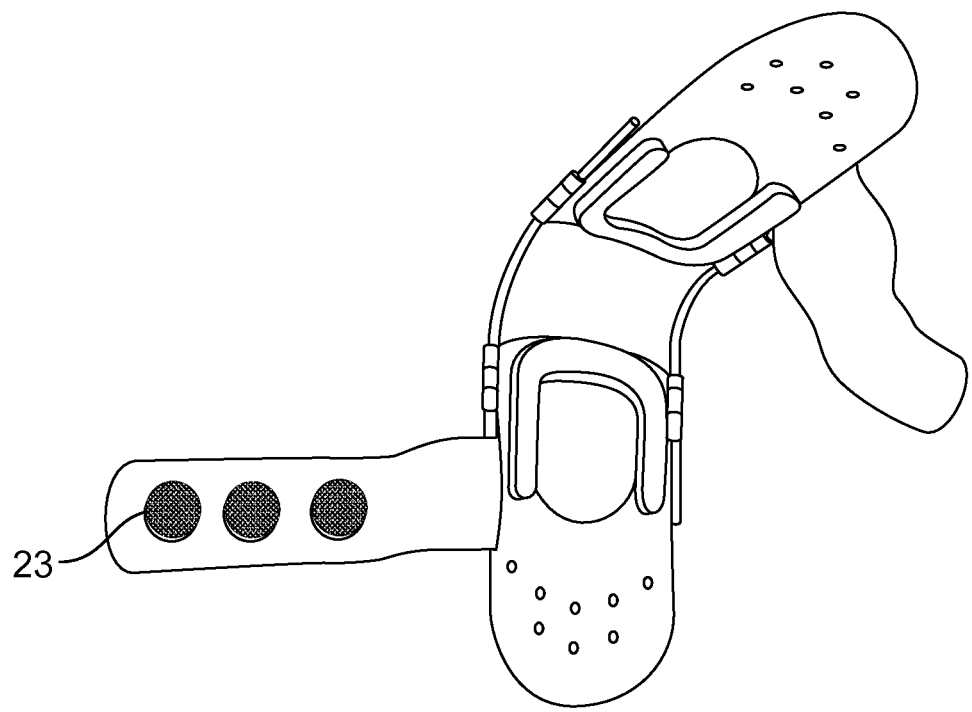
Figure 19J:
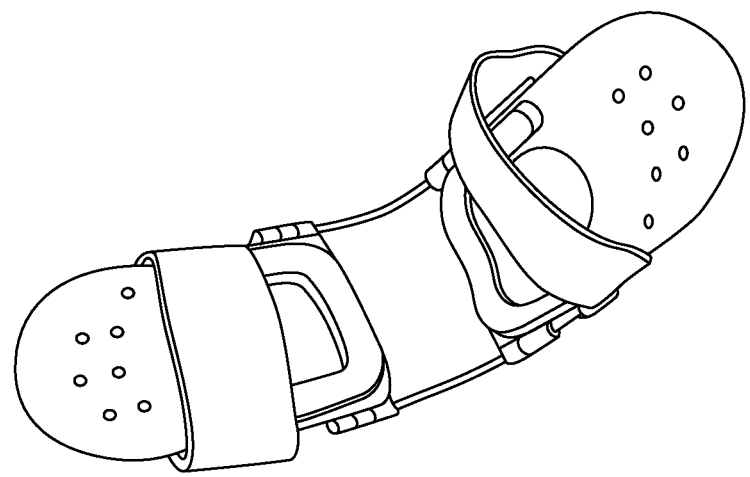
Figure 20:
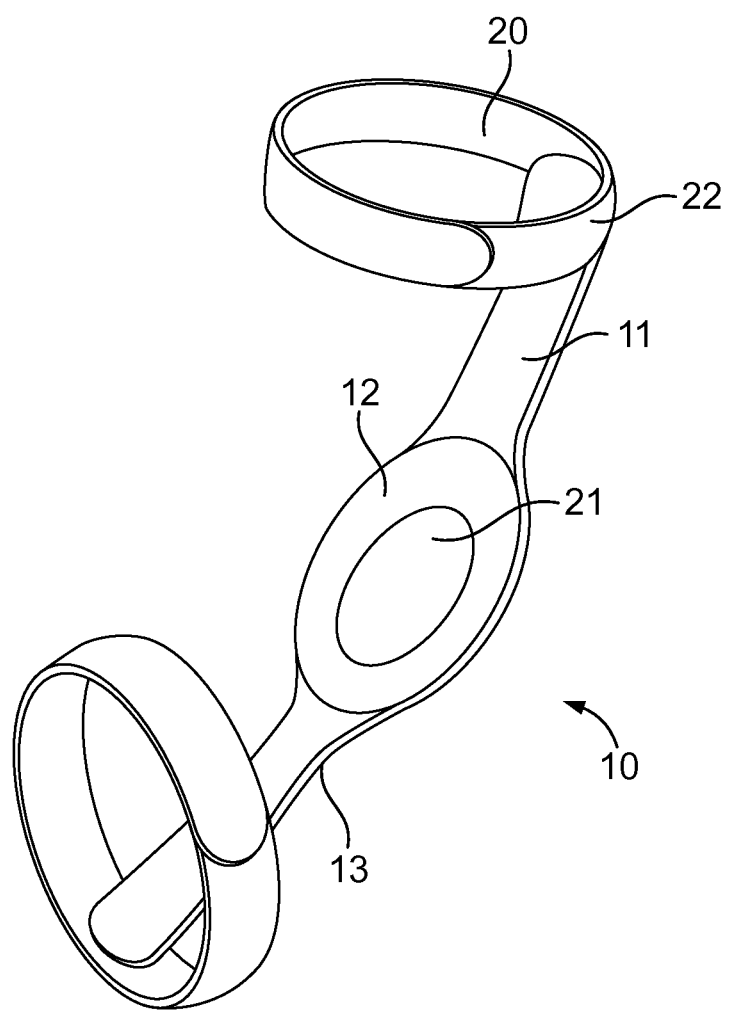
FIG. 20 is a perspective view of an arm support embodiment, where the straps are affixed to the side of the stabilizer.

FIGS. 19E-19I disclose examples of an adjustable leg support embodiment 30, where the stabilizer 11 comprises two separate pieces, at least two windows 21, at least one anchor 60 and two wires 74 which slide into the two stabilizers, making the foot support adjustable to the size of the patient. In addition, these embodiments comprise at least one channel(s) 76. This channel 76 houses the wire and are adjustable to the patient's size and lock the wire into place once the appropriate size is determined. The stabilizer 11 also comprises openings 75 for ventilation and foam padding 73. The straps 20 comprises means for closing 23. Further, FIG. 19H illustrates a slit 70 in the stabilizer to accommodate the strap 20.

Figure 21A:
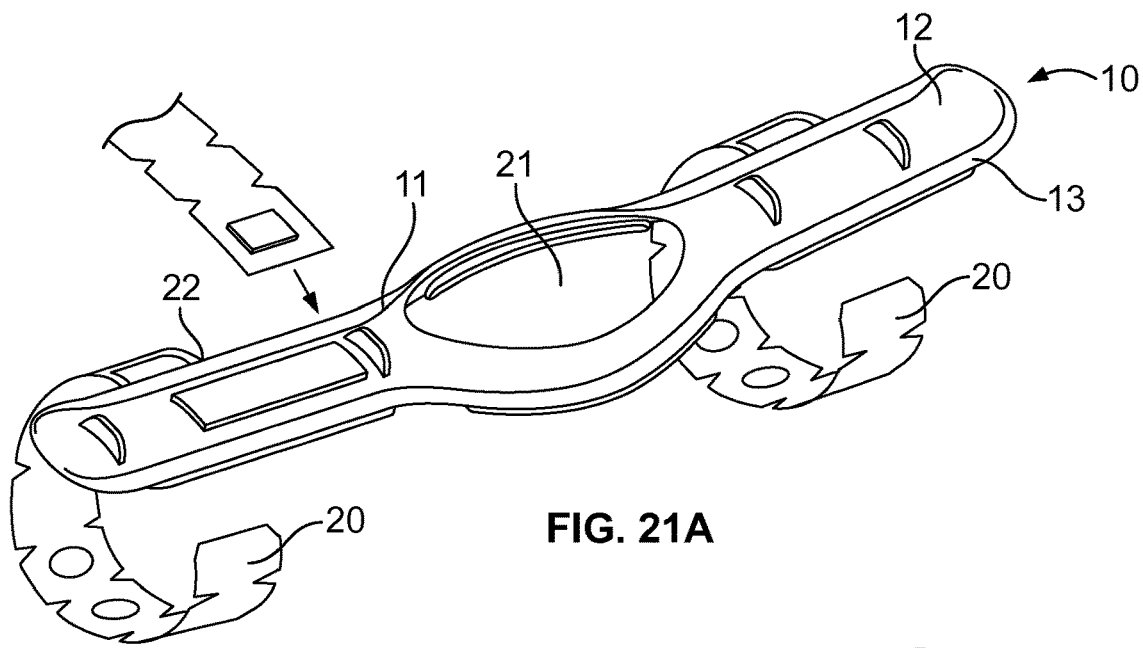
FIGS. 21A-21C are embodiments to an arm support embodiment, where the stabilizer comprises at least one guide or opening to accommodate a strap.
Figure 21B:
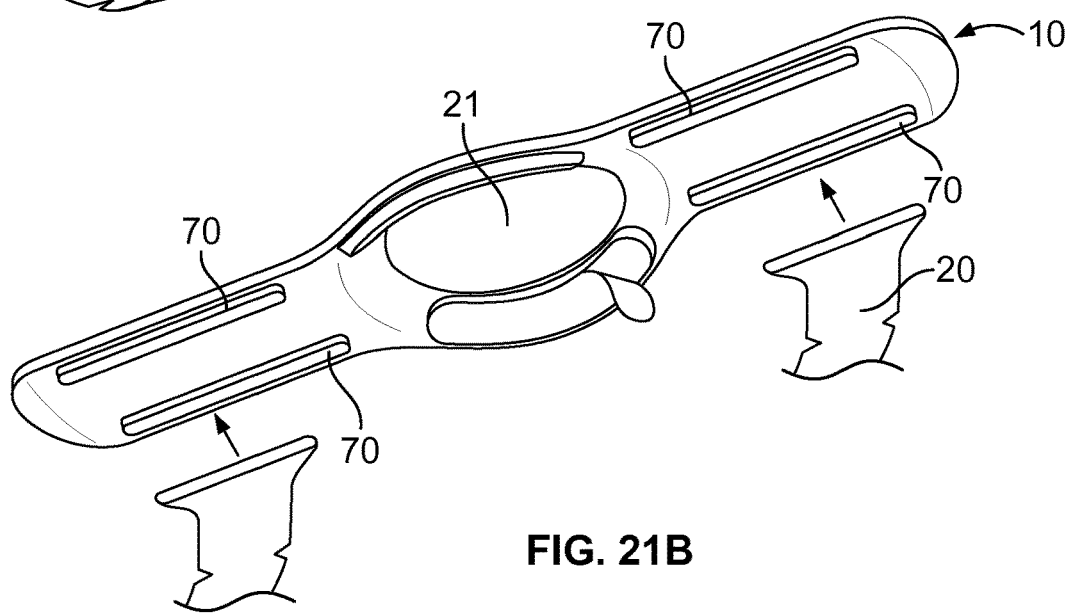
Figure 21C:
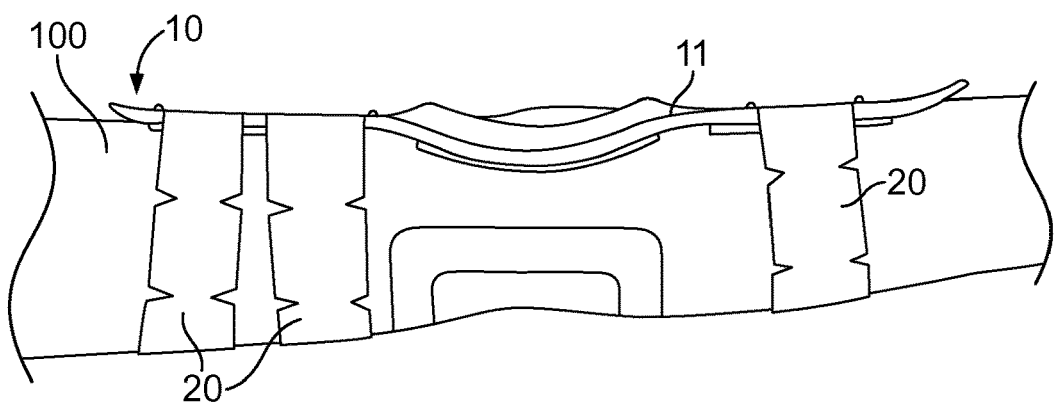

FIG. 20 and FIGS. 21A-21C disclose examples of arm support embodiments 10 comprising a stabilizer 11 and one circular window 21. The stabilizer 11 further comprises slits 70 or openings 70 to accommodate the straps 20. In a further embodiment, the stabilizer comprises a slit 70 or other opening 70 through which the strap(s) 20 could be placed to help hold the strap(s) 20 in place on the anchor. Additional windows include the area around the stabilizer where the forearm 27 and upper arm 100 may be viewed and/or palpated. In some embodiments, these stabilizers 11 are made of a transparent material. In these embodiments, the transparent portion of the stabilizer 11 is a window 21. The oval window 21 in the middle of the stabilizer is for the patient's elbow to rest. Further, FIG. 21A-21B illustrate stabilizers 11 comprising foam padding 73 along some of the stabilizer's perimeter. However, the entire surface of the stabilizer may be covered in transparent foam padding.

Figure 22:
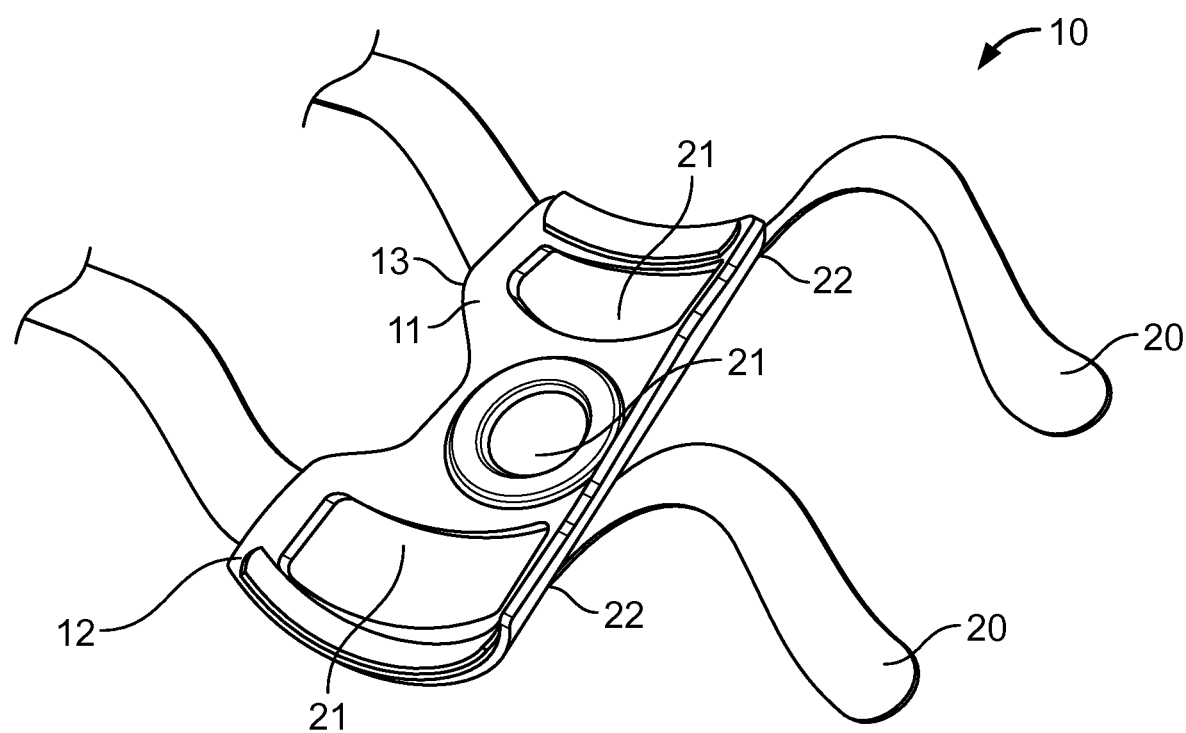
FIG. 22 is a perspective view of an arm support embodiment, where the straps are affixed to the side of the stabilizer.

FIG. 22 discloses an example of an arm support embodiment 10 comprising a stabilizer 11, one circular window 21, two rectangular windows 21, and straps 20. The straps 20 are permanently affixed to the sides 13 of the stabilizer 11 by the affixing means 22. Yet, in another embodiment, the straps 20 may be permanently affixed to bottom, sides 13 or extremity support surface 12 of stabilizer 11 by affixing means 22. In FIG. 22, the stabilizer 11 is made of a transparent material. The transparent portion of the stabilizer 11 is a window 21. The oval window 21 in the middle of the stabilizer is for the elbow to rest. Further, FIG. 22 illustrates a stabilizer 11 comprising foam padding 73 along some of its perimeter. However, the entire stabilizer support surface may be covered in transparent foam padding.

Figure 23A:
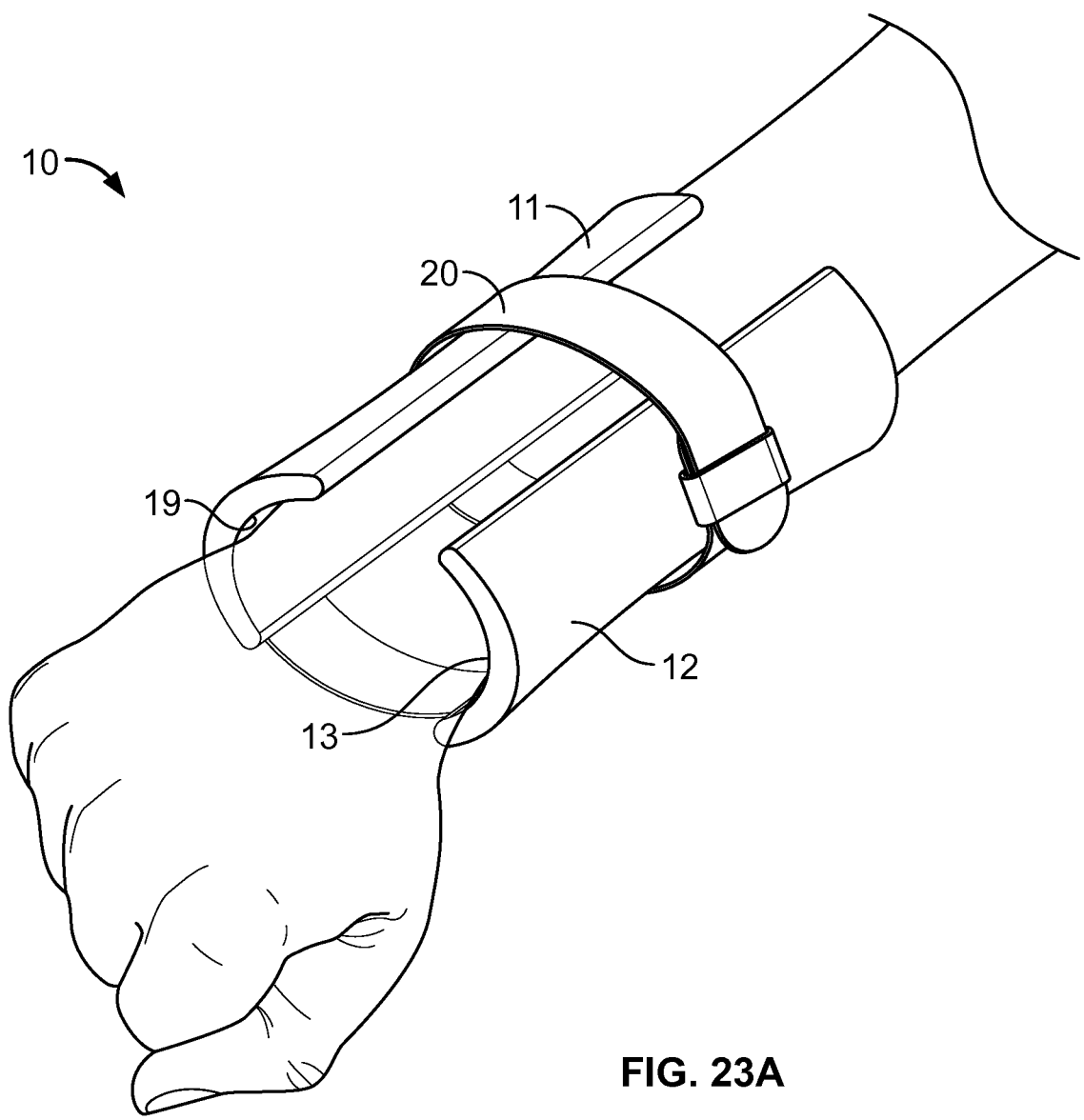
FIG. 23A is a perspective view of an arm support embodiment, where the straps are affixed to the side of the stabilizer, and where the arm support is closed around a patient.

FIG. 23A disclose an example of an arm support embodiment 10. The stabilizer 11 has two extremity support surfaces 12, a bottom 19, sides 13 and straps 20. The extremity support surfaces 12 comprise contoured sides that cling to or hug the arm. They are made from stiff foam material, are held together with an elastic band which is attached to the side of the foam and are held in place with a latching strap. In another embodiment, the arm support 10 can be used on the antecubital fossa area as well.

Figure 23B:
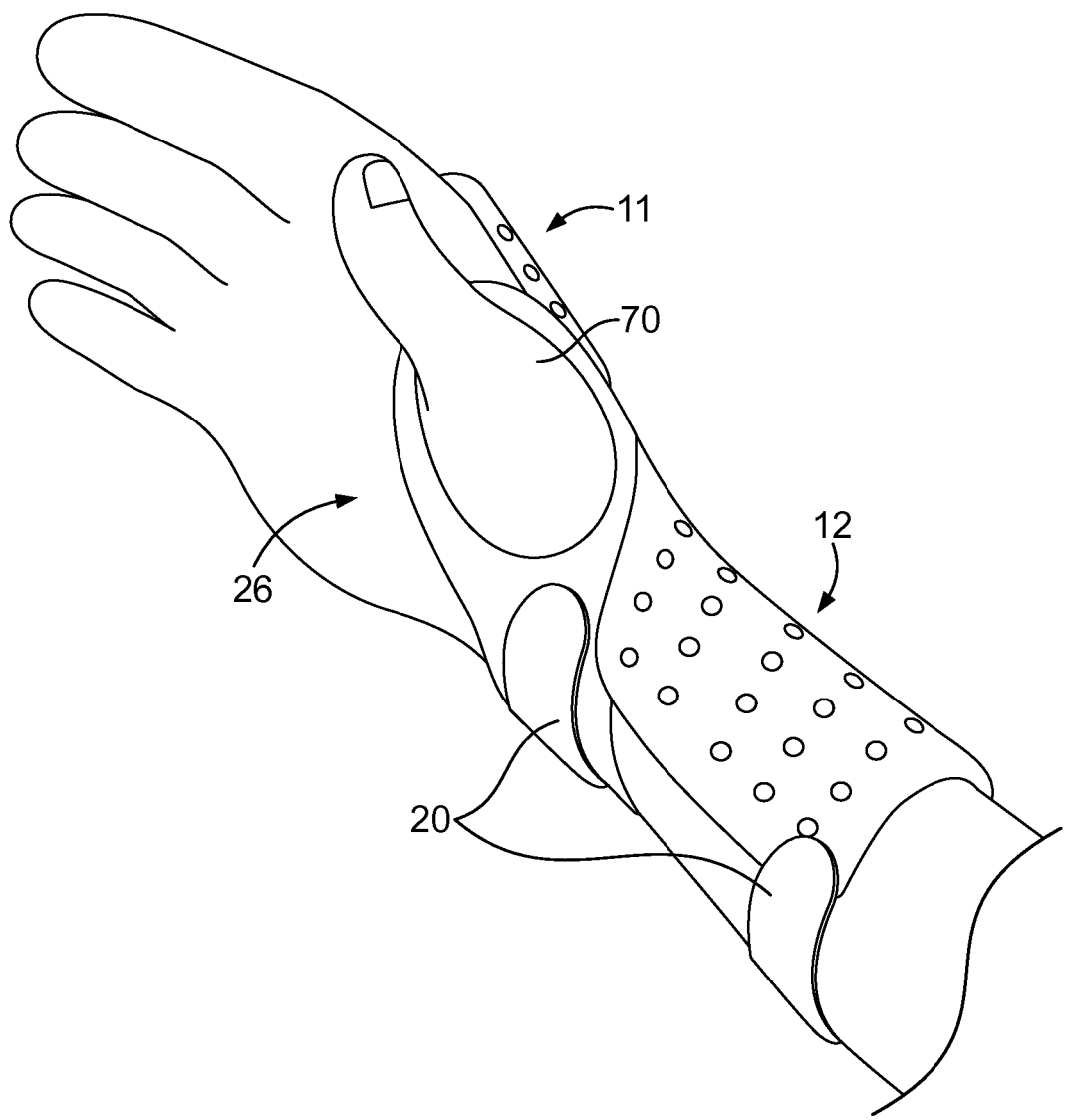
FIG. 23B is a perspective view of an arm support embodiment, where the arm support comprises contoured sides that cling to or hug the arm and also an opening to accommodate the thumb of the patient.

FIG. 23B discloses an example of an arm support embodiment 10. The stabilizer 11 has an extremity support surface 12 and straps 20. The extremity support surface 12 comprises contoured sides that cling to or hug the arm and an opening 70 to accommodate the thumb of the patient. The extremity support surface is made from stiff foam material. Further, the stabilizer 11 comprises openings 75 for ventilation.

Figure 24A:
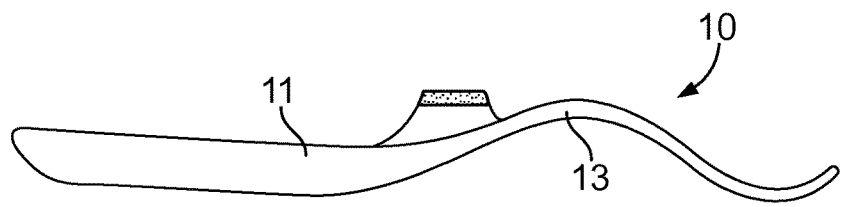
FIG. 24A is a side-view of an arm support embodiment, where the straps are not affixed to the side of the stabilizer.
Figure 24B:
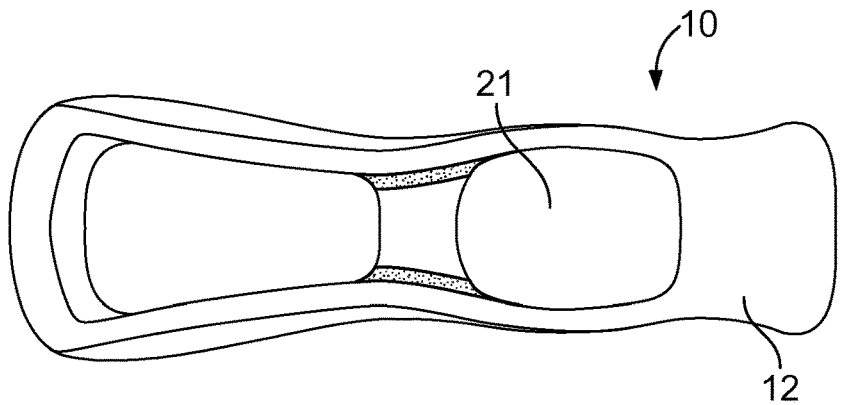
FIG. 24B is a top view of an arm support embodiment, where the straps are not affixed to the side of the stabilizer.

FIGS. 24A-24B disclose examples of arm support embodiments 10. The stabilizer 11 comprises two rectangular windows 21, sides 13, and an extremity support surface 12.

Figure 24C:
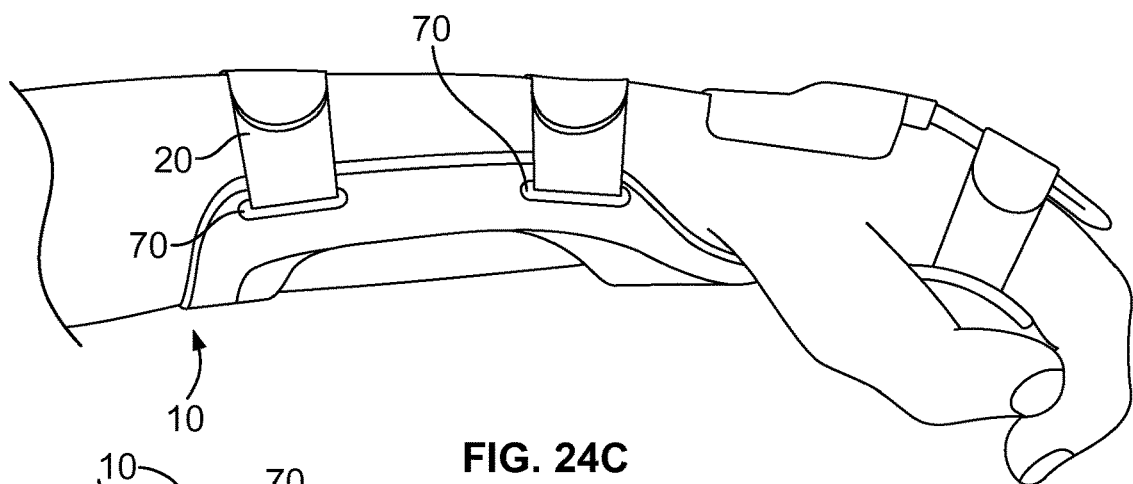
FIG. 24C is a side-view of an arm support embodiment, where the stabilizer comprises at least one opening to accommodate a strap which are affixed to the side of the stabilizer, and the arm support is closed around a patient.
Figure 24D:
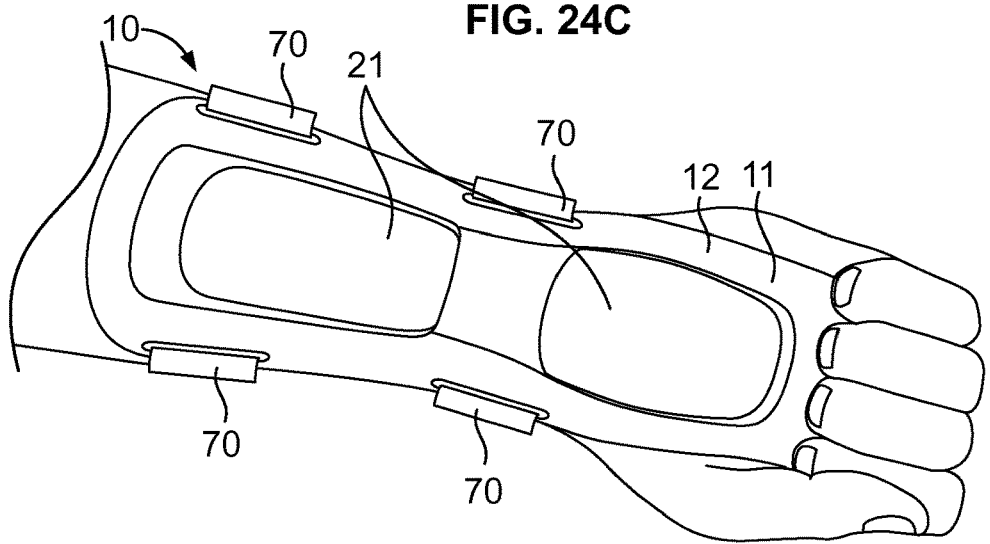
FIG. 24D is a bottom-view of an arm support embodiment, where the stabilizer comprises at least one opening to accommodate a strap which are affixed to the side of the stabilizer, and the arm support is closed around a patient.
Figure 25A:
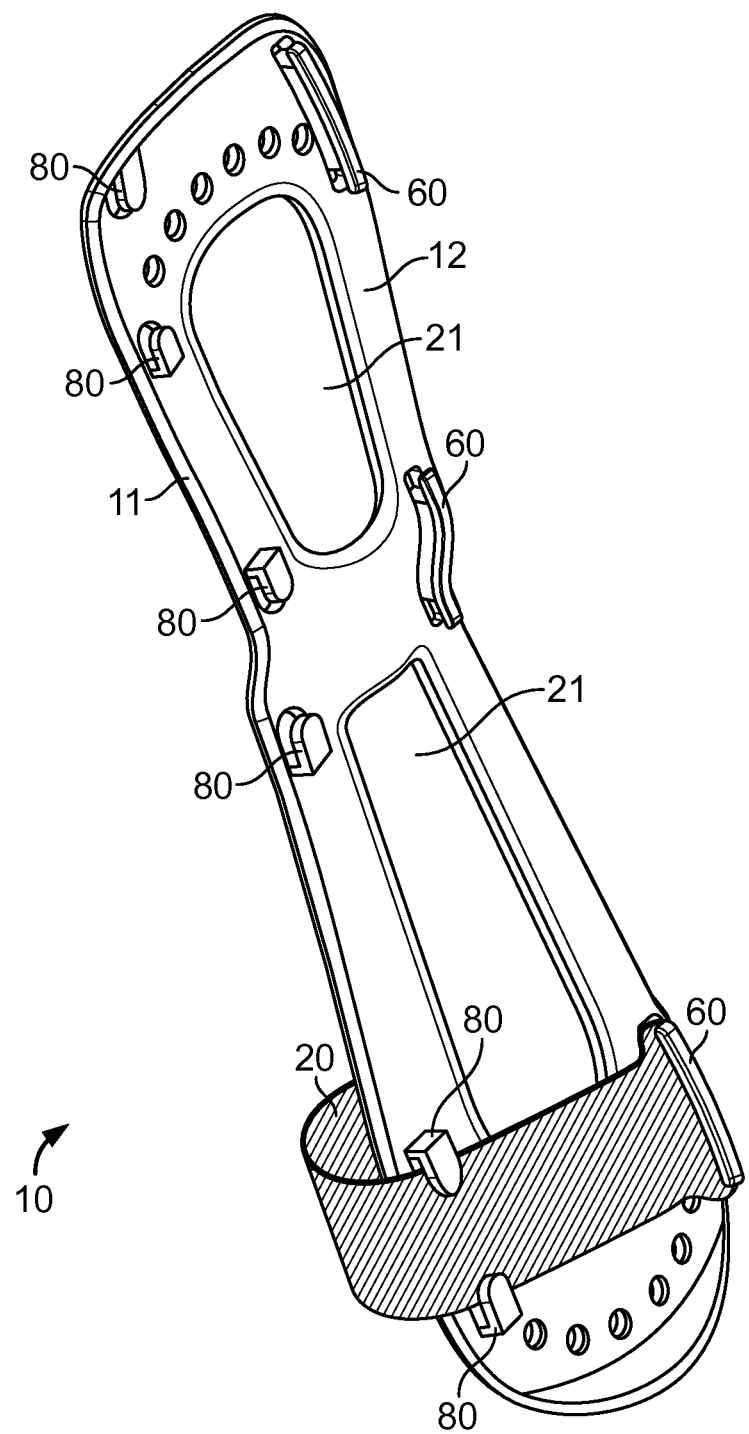
FIGS. 25A-25D are embodiments to an arm support embodiment, where the stabilizer comprises at least one anchor to assist in securing the strap to the stabilizer and at least one guide or opening.
Figure 25B:
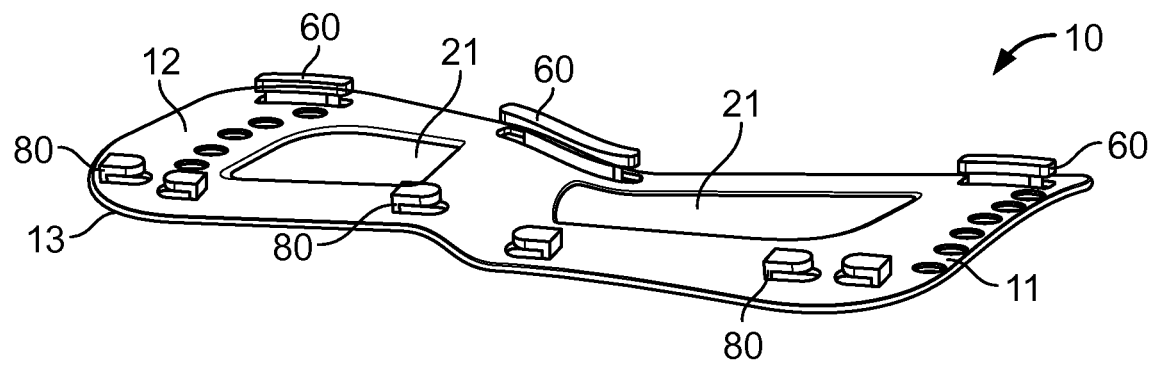
Figure 25C:
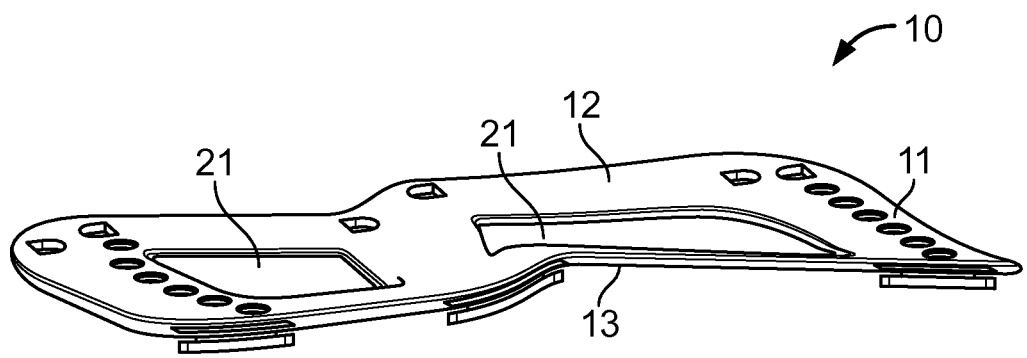
Figure 25D:
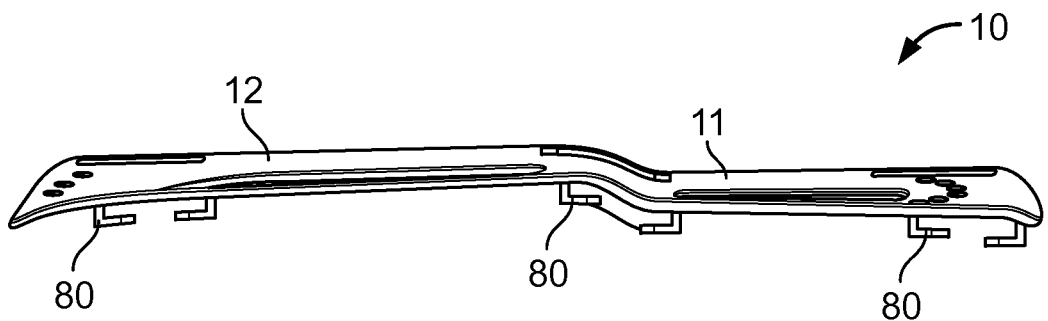
Figure 26A:
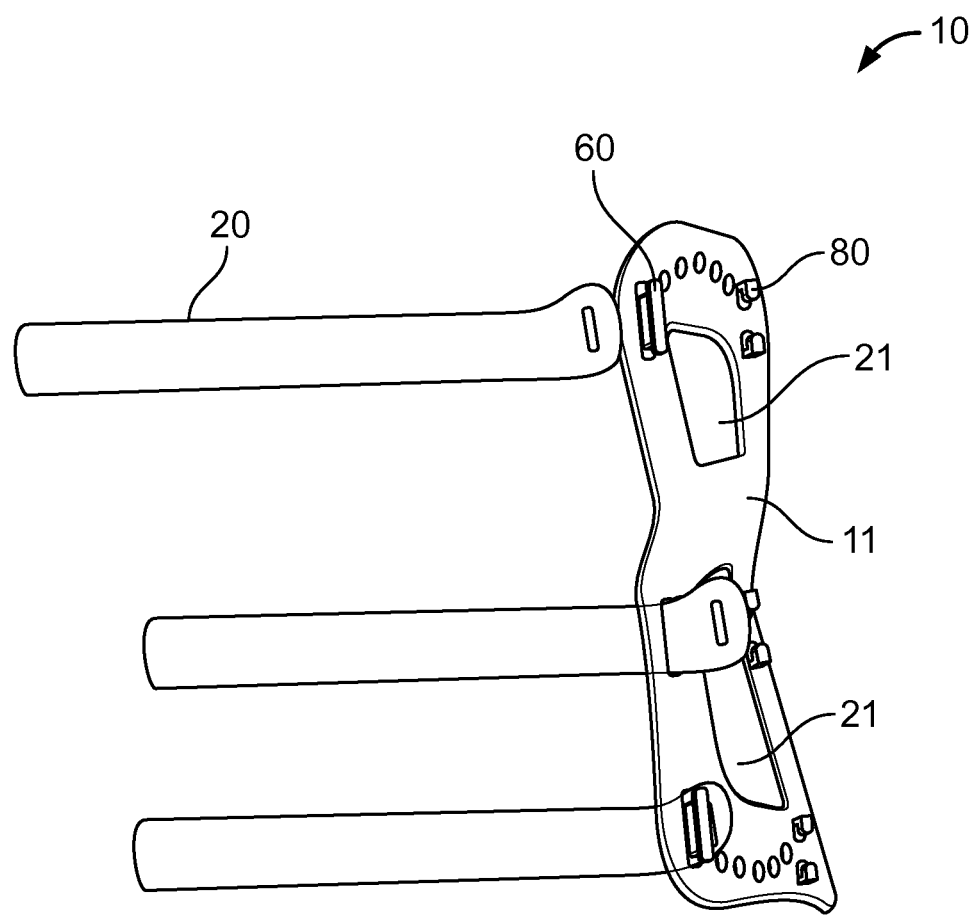
FIGS. 26A-26F are embodiments to an arm support embodiment, where the stabilizer comprises at least one anchor to assist in securing the strap to the stabilizer, and where at least one strap is attached to the anchor.
Figure 26B:
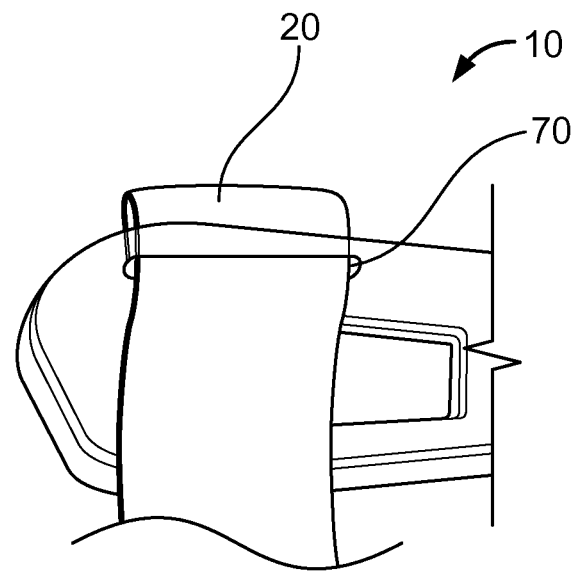
Figure 26C:
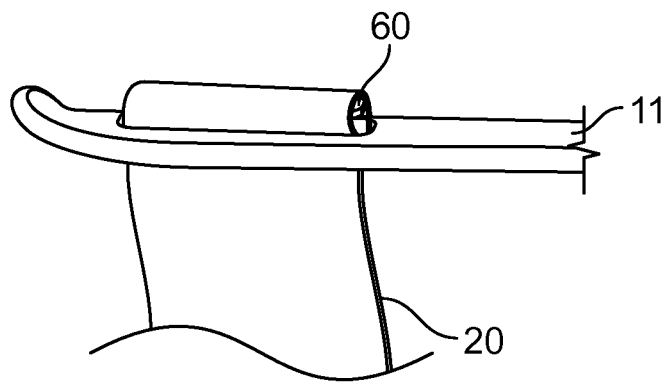
Figure 26D:
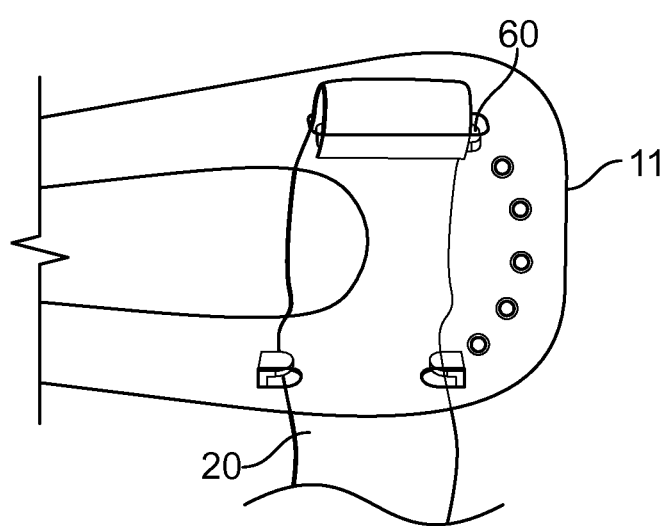
Figure 26E:
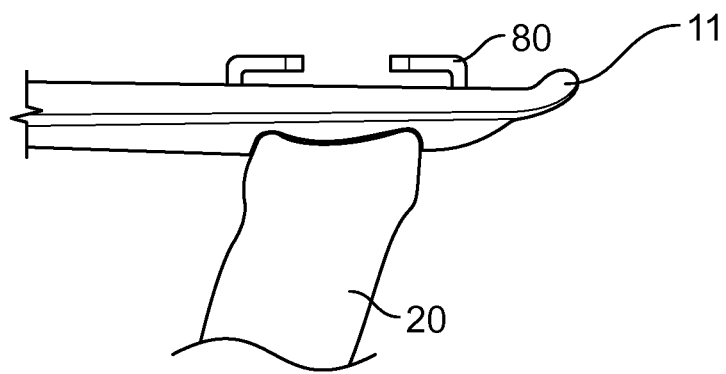
Figure 26F:
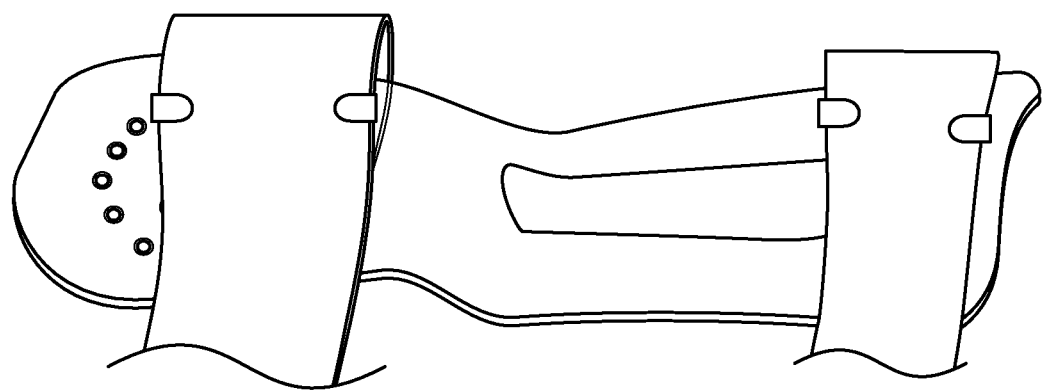

FIGS. 24C-24D disclose examples of arm support embodiments 10. The stabilizer 11 comprises two rectangular windows 21 and an extremity support surface 12. The stabilizer 11 further comprises slits 70 or openings 70 to accommodate the straps 20.

FIGS. 25A-25D disclose examples of arm support embodiments 10 comprising a stabilizer 11, three extremity support surfaces 12 and two rectangular windows 21. The stabilizer 11 further comprises anchors 60, as well as notches 80 or guides 80, to accommodate the straps 20.

FIGS. 26A-26F disclose examples of arm support embodiments 10 comprising a stabilizer 11 and two rectangular windows 21. The stabilizer 11 further comprises anchors 60 as well as notches 80 or guides 80 to accommodate the straps 20. The stabilizer 11 further comprises slits 70 or openings 70 to accommodate the straps 20.

Figure 27C:
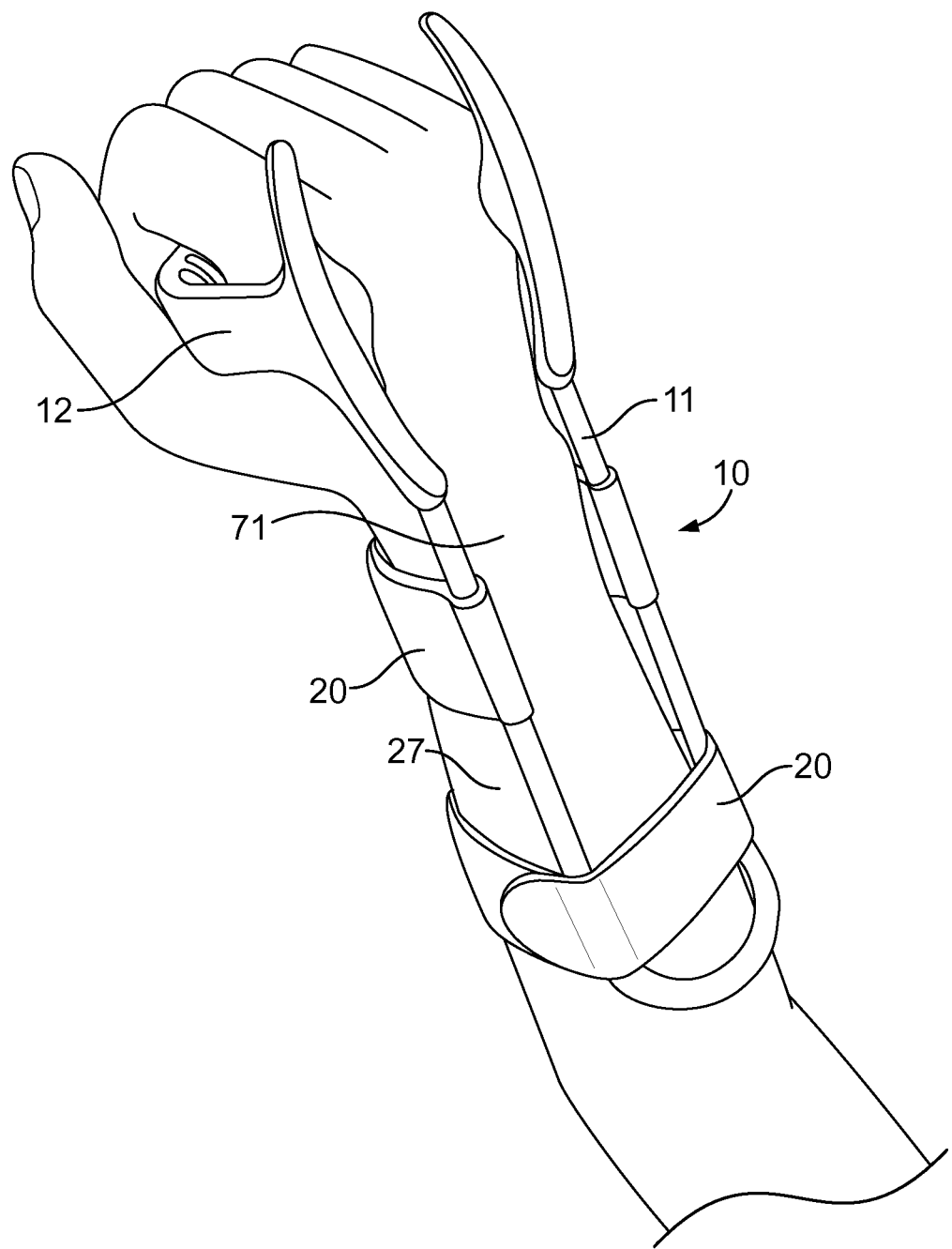
FIG. 27C is a perspective view of the top of the arm support, where the support is closed around a patient.
Figure 27D:
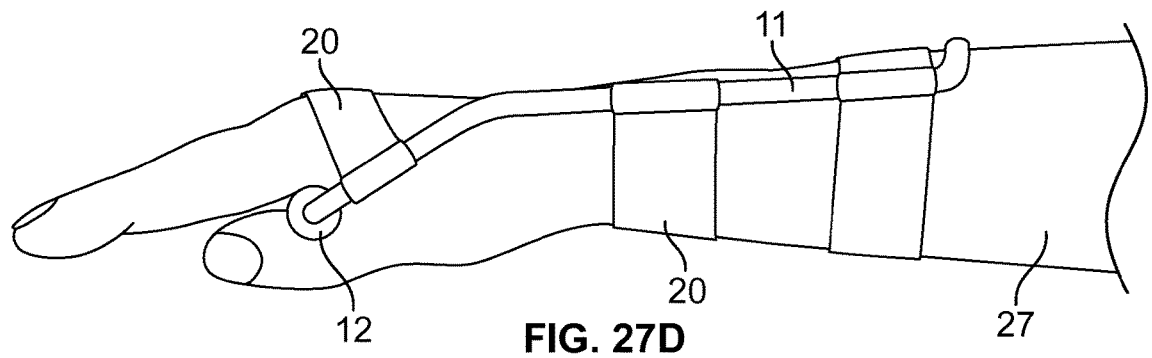
FIG. 27D is a side view of the side of an arm support, where the support is closed around a patient.
Figure 27E:
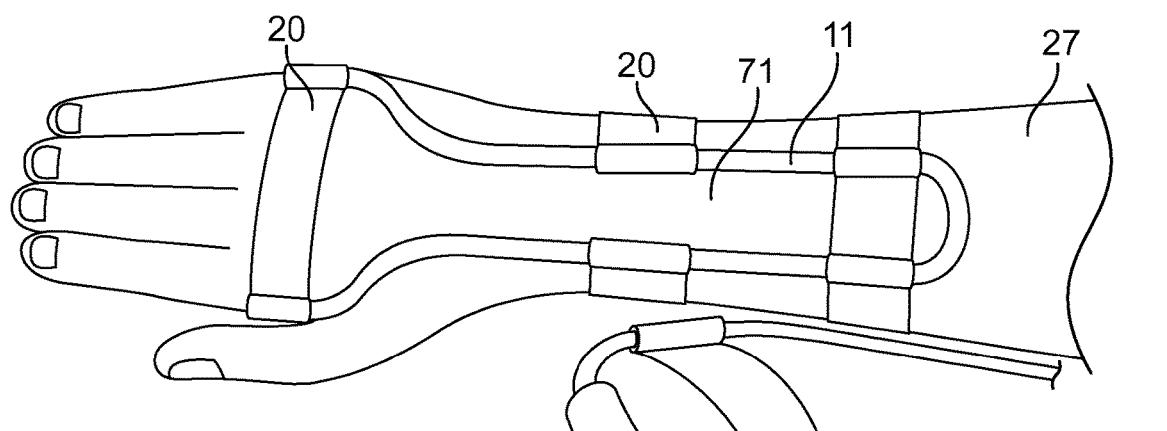
FIG. 27E is a top view of the top of the arm support, where the support is closed around a patient.
Figure 27F:
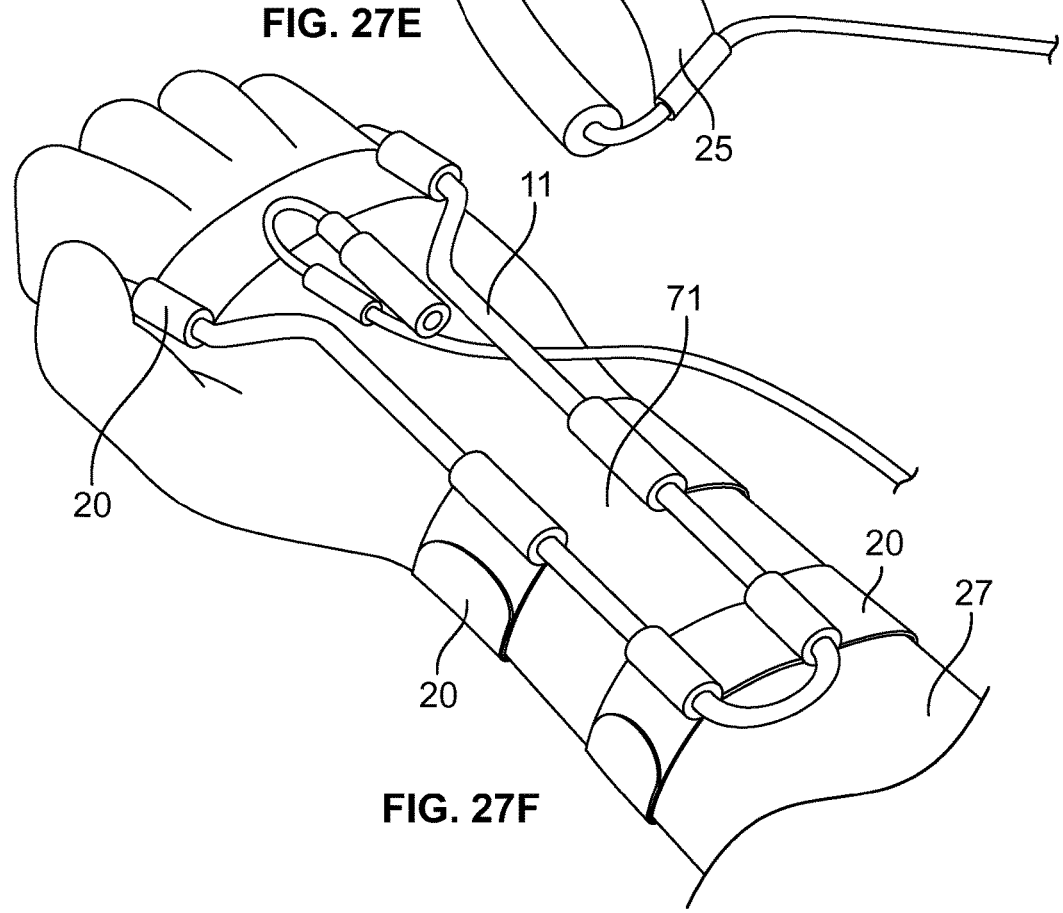
FIG. 27F is a top view of the top of the arm support, where the support is closed around a patient and where the arm support may be used with an IV site guard (e.g., I.V. House UltraDome®).

FIGS. 27A-27F disclose examples of arm support embodiments 10 comprising a wire stabilizer 11. The wire stabilizer 11 has an extremity support surface 12. The stabilizer 11 is made of wire, however, the stabilizer could be made of other materials that can achieve the same design. The U-shaped stabilizer 11 forms an open channel 71 for visibility of a patient's palm and forearm 27 with ease. The straps 20 are permanently affixed to the stabilizer 11 by the affixing means. The closure means will fasten the arm support embodiment 10 around a patient. In FIGS. 27D-27F, a stretch fabric strap 20 may be permanently affixed to stabilizer 11 by affixing means and the extremity support surface 12 comprises a padded grip. The stabilizer also contains a wrist support 25.

Although specific embodiments have been described, it should be appreciated that other embodiments utilizing the concept of the present embodiments are possible. All embodiments, for example, are not intended to be limited to the specific materials discussed and exemplified and disclosed herein; rather, the embodiments are defined by the claims and the equivalents thereof.

We claim:

1. A method for assessing a patient's extremity for signs of infiltration and extravasation during peripheral intravenous (IV) therapy comprising:
    (a) locating a venipuncture site on the extremity of the patient;
    (b) affixing to the patient an extremity support at the venipuncture site on the extremity of the patient, wherein the extremity support comprises a stabilizer having (i) an upper portion, a middle portion and a lower portion, (ii) at least one window, and (iii) a first strap that is attached to the upper portion of the stabilizer and a second strap that is attached to the lower portion of the stabilizer; wherein the upper portion and the lower portion of the stabilizer are wider than the middle portion of the stabilizer; and wherein the stabilizer inhibits movement of the extremity and does not surround the extremity;
    (c) wrapping the first strap and the second strap around the extremity of the patient to secure the extremity support to the patient; and
    (d) palpating the extremity for signs of infiltration and extravasation during IV therapy without removing the extremity support.

2. The method of claim 1, wherein the extremity support comprises three straps.

3. The method of claim 1, wherein the stabilizer further comprises at least one slit to accommodate the first strap.

4. The method of claim 1, wherein the stabilizer further comprises at least one anchor; and wherein the first strap is affixed to the anchor.

5. The method of claim 1, wherein the extremity support is an arm support.

6. The method of claim 1, wherein the extremity support is a leg support.

7. The method of claim 1, wherein the stabilizer is transparent.

8. The method of claim 1, wherein the stabilizer is plastic.

9. The method of claim 1, wherein the stabilizer comprises at least two windows.

10. The method of claim 1, wherein the stabilizer further comprises ventilation holes.

11. The method of claim 1, wherein the stabilizer is contoured to fit a patient's extremity.

12. The method of claim 1, wherein the stabilizer further comprises padding.

13. The method of claim 1, wherein the first strap is mesh, cloth, stretch wrap, burn net, gauze, cotton cloth, or nylon.

14. The method of claim 1, wherein the first strap comprises elastic or silicon.

15. The method of claim 1, wherein the stabilizer further comprises at least one slit to accommodate the second strap.

16. The method of claim 1, wherein the stabilizer further comprises at least one anchor; and wherein the second strap is affixed to the anchor.

17. The method of claim 1, wherein the second strap is mesh, cloth, stretch wrap, burn net, gauze, cotton cloth, or nylon.

18. The method of claim 1, wherein the second strap comprises elastic or silicon.

19. The method of claim 1, wherein the stabilizer is in the shape of an hourglass.

\* \* \* \* \*